(12) United States Patent
Ye et al.

(10) Patent No.: US 7,732,609 B2
(45) Date of Patent: Jun. 8, 2010

(54) 5-(ARYLSULFONYL)- PYRAZOLOPIPERI-DINES

(75) Inventors: Xiaocong Michael Ye, Palo Alto, CA (US); Albert W. Garofalo, South San Francisco, CA (US); Jacek J. Jagodinski, Redwood City, CA (US); Andrei W. Konradi, Burlingame, CA (US); Christopher M. Semko, Fremont, CA (US); Jenifer L. Smith, South San Francisco, CA (US); Ying-zi Xu, Palo Alto, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/566,070

(22) Filed: Dec. 1, 2006

(65) Prior Publication Data

US 2007/0155753 A1    Jul. 5, 2007

Related U.S. Application Data

(60) Provisional application No. 60/741,366, filed on Dec. 1, 2005.

(51) Int. Cl.
*C07D 471/04* (2006.01)
*A61K 31/437* (2006.01)
(52) U.S. Cl. .................. 546/119; 514/303
(58) Field of Classification Search .......... 514/303; 546/119
See application file for complete search history.

(56) References Cited

FOREIGN PATENT DOCUMENTS

| WO | 96/12720 | 5/1996 |
|---|---|---|
| WO | 02/12242 | 2/2002 |
| WO | 2004/060892 | 7/2004 |
| WO | 2006/049880 | 5/2006 |
| WO | 2007/022502 | 2/2007 |

*Primary Examiner*—Rita J Desai
*Assistant Examiner*—David K O'Dell
(74) *Attorney, Agent, or Firm*—McDonnell Boehnen Hulbert & Berghoff LLP

(57) ABSTRACT

The invention provides N-cyclic sulfonamido compounds of Formula I

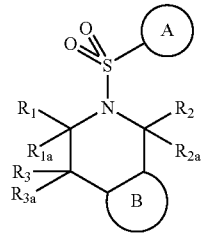

(I)

wherein A, B, $R_1$, $R_{1a}$, $R_2$, $R_{2a}$, $R_3$ and $R_{3a}$ are as described in the specification. Compounds of Formula I are useful in treating or preventing cognitive disorders, such as Alzheimer's disease. The invention also encompasses pharmaceutical compositions comprising compounds of Formula I, methods of preparing compounds of formula I, and methods of treating cognitive disorders, such as Alzheimer's disease.

20 Claims, No Drawings

5-(ARYLSULFONYL)- PYRAZOLOPIPERIDINES

This application claims priority from U.S. Provisional Patent Application No. 60/741,366, filed on Dec. 1, 2005, the disclosure of which is incorporated by reference in its entirety, for all purposes.

BACKGROUND OF THE INVENTION

1. Field of the Invention

The invention relates to 5-(arylsulfonyl)-pyrazolopiperidine compounds, which inhibit gamma secretase and β-amyloid peptide release and/or its synthesis. Therefore, the N-cyclic sulfonamido compounds are useful in the prevention of cognitive disorders in patients susceptible to cognitive disorders and/or in the treatment of patients with cognitive disorders in order to inhibit further deterioration in their condition.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner et al., Biochem. Biophys. Res. Commun., 120:885-890 (1984) The isolation procedure and the sequence data for the first 28 amino acids are described in U.S. Pat. No. 4,666,829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). Sequential processing of the precursor protein by the enzymes referred to generically as beta- and gamma-secretases, give rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, for example, Selkoe, Neuron, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate et al., Nature, 349:704-706 (1990); Chartier Harlan et al., Nature, 353:844-846 (1989); and Murrell et al., Science, 254:97-99 (1991.) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan et al., Nature Genet., 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of β-amyloid peptide fragments of 40 or 42 residues in length. The immediate substrates for gamma secretase are β-cleaved, as well as α-cleaved carboxy-terminal fragments (CTF) of APP. The gamma-secretase cleavage site on β- and β-CTF fragments occurs in the predicted transmembrane domain of APP. Inhibitors of gamma-secretase have been demonstrated to effect amyloid pathology in transgenic mouse models (Dovey, H. F., V. John, J. P. Anderson, L. Z. Chen, P. de Saint Andrieu, L. Y. Fang, S. B. Freedman, B. Folmer, E. Goldbach, E. J. Holsztynska et al. (2001). "Functional gamma-secretase inhibitors reduce beta-amyloid peptide levels in brain." J Neurochem 76(1): 173-81.)

Gamma secretase is recognized to be a multi-subunit complex comprised of the presenilins (PS1 or PS2), Nicastrin, Aph-1, and Pen 2 (De Strooper, B. (2003). "Aph-1, Pen-2, and Nicastrin with Presenilin generate an active gamma-Secretase complex." Neuron 38(1): 9-12; Edbauer, D., E. Winkler, J. T. Regula, B. Pesold, H. Steiner and C. Haass (2003). "Reconstitution of gamma-secretase activity." Nat Cell Biol 5(5): 486-8; Kimberly, W. T., M. J. LaVoie, B. L. Ostaszewski, W. Ye, M. S. Wolfe and D. J. Selkoe (2003). "Gamma-secretase is a membrane protein complex comprised of presenilin, nicastrin, Aph-1, and Pen-2." Proc Natl Acad Sci USA 100(11): 6382-7). Much evidence indicates that PS comprises the catalytic moiety of the complex, while the other identified subunits are necessary for proper maturation and sub-cellular localization of the active enzyme complex (reviewed in De Strooper, B. (2003). "Aph-1, Pen-2, and Nicastrin with Presenilin generate an active gamma-Secretase complex." Neuron 38(1): 9-12.) Consistent with this hypothesis: PS knock-out mice exhibit significant reductions in β-amyloid production (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; Haass, C. and D. J. Selkoe (1998). "Alzheimer's disease. A technical KO of amyloid-beta peptide." Nature 391(6665): 339-40; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2); point mutations of putative active site aspartate residues in PS trans-membrane domains inhibit β-amyloid production in cells in a dominant negative fashion (Wolfe, M. S., W. Xia, B. L. Ostaszewski, T. S. Diehl, W. T. Kimberly and D. J, Selkoe (1999). "Two transmembrane aspartates in presenilin-1 required for presenilin endoproteolysis and gamma-secretase activity." Nature 398(6727): 513-7; Kimberly, W. T., W. Xia, T. Rahmati, M. S. Wolfe and D. J. Selkoe (2000). "The transmembrane aspartates in presenilin 1 and 2 are obligatory for gamma-secretase activity and amyloid beta-protein generation." J Biol Chem 275(5): 3173-8); active site directed substrate-based transition state isosteres designed to inhibit gamma secretase directly conjugate to PS (Esler, W. P., W. T. Kimberly, B. L. Ostaszewski, T. S. Diehl, C. L. Moore, J. Y. Tsai, T. Rahmati, W. Xia, D. J. Selkoe and M. S. Wolfe (2000). "Transition-state analogue inhibitors of gamma-secretase bind directly to presenilin-1." Nat Cell Biol 2(7): 428-34; Li, Y. M., M. Xu, M. T. Lai, Q. Huang, J. L. Castro, J. DiMuzio-Mower, T. Harrison, C. Lellis, A. Nadin, J. G. Neduvelil et al. (2000). "Photoactivated gamma-secretase inhibitors directed to the active site covalently label presenilin 1." Nature 405(6787): 689-94); finally, allosteric gamma secretase inhibitors have likewise been demonstrated to bind directly to PS (Seiffert, D., J. D. Bradley, C. M. Rominger, D. H. Rominger, F. Yang, J. E. Meredith, Jr., Q. Wang, A. H. Roach, L. A. Thompson, S. M. Spitz et al. (2000). "Presenilin-1 and -2 are molecular targets for gamma-secretase inhibitors." J Biol Chem 275(44): 34086-91.)

Current evidence indicates that in addition to APP processing leading to β-amyloid synthesis, gamma-secretase also mediates the intra-membrane cleavage of other type I trans-membrane proteins (reviewed in Fortini, M. E. (2002). "Gamma-secretase-mediated proteolysis in cell-surface-receptor signaling." Nat Rev Mol Cell Biol 3(9): 673-84, see also Struhl, G. and A. Adachi (2000). "Requirements for presenilin-dependent cleavage of notch and other transmembrane proteins." Mol Cell 6(3): 625-36.) Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J., C. E. Lindsell, F. F. del Amo, G. Weinmaster and T. Gridley (1994). "Notch1 is essential for postimplantation development in mice." Genes Dev 8(6): 707-19; Conlon, R. A., A. G. Reaume and J. Rossant (1995). "Notch1 is required for the coordinate segmentation of somites." Development 121(5): 1533-45.) The Notch KO phenotype is very similar to the phenotype observed PS1 KO mice, and precisely reproduced by PS1/PS2 double KO mice (De Strooper et al. (1998). "Deficiency of presenilin-1 inhibits the normal cleavage of amyloid precursor protein." Nature 391(6665): 387-90; Donoviel, D. B., A. K. Hadjantonakis, M. Ikeda, H. Zheng, P. S. Hyslop and A. Bernstein (1999). "Mice lacking both presenilin genes exhibit early embryonic patterning defects." Genes Dev 13(21): 2801-10; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2.) This convergence of phenotypes observed in knock-out mice of either the substrate (Notch) or the enzyme (PS) suggests that inhibitors of gamma secretase that also inhibit Notch function may be limited as therapeutic agents owing to the importance of Notch function in adult tissues (Fortini, M. E. (2002). "Gamma-secretase-mediated proteolysis in cell-surface-receptor signaling." Nat Rev Mol Cell Biol 3(9): 673-84.) As APP knock-out mice develop normally and without an overt phenotype Zheng, H., M. Jiang, M. E. Trumbauer, R. Hopkins, D. J. Sirinathsinghji, K. A. Stevens, M. W. Conner, H. H. Slunt, S. S. Sisodia, H. Y. Chen et al. (1996). "Mice deficient for the amyloid precursor protein gene," Ann N Y Acad Sci 777: 421-6; Zheng, H., M. Jiang, M. E. Trumbauer, D. J, Sirinathsinghji, R. Hopkins, D. W. Smith, R. P. Heavens, G. R. Dawson, S. Boyce, M. W. Conner et al. (1995). "beta-Amyloid precursor protein-deficient mice show reactive gliosis and decreased locomotor activity." Cell 81(4): 525-31, the cumulative evidence, therefore, suggests that preferred gamma secretase inhibitors would have selectivity for inhibiting gamma secretase processing of APP over gamma secretase processing of Notch.

SUMMARY OF THE INVENTION

In a broad aspect, the invention provides compounds of Formula I:

Compounds of the formula:

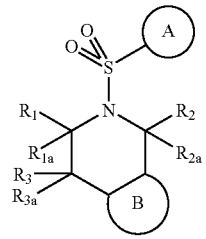

(Formula I)

stereoisomers, tautomers, mixtures of stereoisomers and/or tautomers or pharmaceutically acceptable salts thereof, wherein the A-ring is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxyl, hydroxyalkyl, CN, aryloxy, arylalkyloxy, —$SO_2$—($C_1$-$C_6$ alkyl), —NR'R", $C_1$-$C_6$ alkanoyl, $C_0$-$C_3$alkyl-C(O)OR', heteroaryl, heterocycloalkyl, aryl, arylalkyl, or —$SO_2$—NR'R", where each R' and R" is independently H or $C_1$-$C_6$ alkyl or R' and R" with the atom to which they are attached may form a 3-8 membered ring optionally including an additional heteroatom such as N, O or S;

the B-ring is a heteroaryl or heterocycloalkyl ring, each of which is optionally substituted at a substitutable position with a group that is independently $C_1$-$C_6$ alkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$—R', hydroxyl, hydroxyalkyl, halo, $C_1$-$C_2$ haloalkyl, $C_1$-$C_2$ haloalkoxy, —NR'C(O)R", —NR'SO$_2$R", —C(O)R', —CO$_2$R', —C(O)alkylOC(O)R', —C(O)NR'R", oxo, CN, or $C_0$-$C_1$alkylaryl, where the aryl is optionally substituted with 1-5 groups independently selected from halogen, $C_1$-$C_6$ alkyl, —C(O)OR', $C_1$-$C_6$ alkoxy, haloalkyl, haloalkoxy, hydroxyl, CN, NO$_2$, aryloxy, —S(O)$_{0-2}$—($C_1$-$C_6$ alkyl), —C(O)NR'R", —NR'R", $C_1$-$C_6$ alkanoyl, pyridyl, phenyl, and —SO$_2$NR'R"; and $R_1$, $R_{1a}$, $R_2$, and $R_{2a}$ are independently hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, aryl, aryl$C_1$-$C_6$ alkyl, heteroaryl, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, or —$C_0$-$C_6$ alkyl-OC(O)-heterocycloalkyl, wherein each aryl, heteroaryl, and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl;

$R_3$, and $R_{3a}$ are independently hydrogen, halogen, $C_1$-$C_6$ alkyl, OH, or NR'R";

$R_1$, and $R_{1a}$, or $R_2$ and $R_{2a}$ or $R_3$ and $R_{3a}$ combined form =O or =N—OR, where R is hydrogen, $C_1$-$C_6$ alkyl, aryl (such as phenyl) or arylalkyl (such as benzyl or phenethyl); or $R_1$, and $R_{1a}$, or $R_2$ and $R_{2a}$ or $R_3$ and $R_{3a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_3$ form a double bond The compounds of Formula I inhibit β-amyloid peptide release and/or its synthesis and, therefore, are useful in the prevention of Alzheimer's Disease (AD) in patients susceptible to AD and/or in the treatment of patients with AD in order to inhibit further deterioration in their condition. The invention also, encompasses pharmaceutical compositions containing the compounds of Formula I, and methods employing such compounds or compositions in the treatment of cognitive diseases, including Alzheimer's disease.

The invention also provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimer's disease and who is in need of such treatment which comprises administration of a therapeutically effective amount of a compound of formula (I).

In another aspect, the invention provides methods of preparing the compounds of interest, as well as intermediates useful in preparing the compounds of interest.

DETAILED DESCRIPTION OF THE INVENTION

As described above, the invention provides compounds of Formula I.

In another aspect, the invention provides compounds of formula 2, i.e., compounds of Formula I wherein the A-ring is phenyl or naphthyl, which is optionally substituted at a substitutable position with halogen, $C_1$-$C_6$ alkyl, $C_1$-$C_6$ alkoxy, $C_1$-$C_6$ haloalkyl, $C_1$-$C_6$ haloalkoxy, hydroxyl, hydroxyalkyl, CN, phenyloxy, benzyloxy, —$SO_2$—($C_1$-$C_6$ alkyl), —NR'R", $C_1$-$C_6$ alkanoyl, pyridyl, phenyl, benzyl, or —$SO_2$—NR'R", where each R' and R" is independently H or $C_1$-$C_6$ alkyl.

In still another aspect, the invention provides compounds of formula 3, i.e., compounds of Formula I wherein the B-ring is pyrazolyl, imidazolyl, pyrrolyl, triazolyl, pyrrolidinyl, pyrazolidinyl, imidazolidinyl, isoxazolyl, indolyl, pyrimidyl, or pyridyl, each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, or $C_0$-$C_1$alkyl phenyl, are optionally substituted with 1 to 5 groups that are independently halogen, hydroxyl, $C_1$-$C_6$ alkyl, $C_1$-$C_6$ alkoxy, $C_1$-$C_4$ haloalkyl, $C_1$-$C_4$haloalkoxy, $C_1$-$C_6$ alkanoyl, —NR'R", —CO$_2$R', —CONR'R", CN or NO$_2$.

In yet another aspect, the invention provides compounds of formula 4, i.e., compounds of Formula I wherein $R_1$ is $C_1$-$C_6$ alkyl, $C_3$-$C_6$cycloalkyl, $C_3$-$C_6$cycloalkyl $C_1$-$C_6$ alkyl, phenyl, biphenyl, phenyl$C_1$-$C_6$ alkyl, pyridyl, benzofuranyl, benzothienyl, benzimidazolyl, quinolinyl, isoquinolinyl, quinoxalinyl, quinazolinyl, tetrazolyl, oxazolyl, thiazolyl, imidazolyl, oxadiazolyl, thiazolyl, pyrimidyl, —CO$_2$R', —CONR'R', $C_1$-$C_6$ haloalkyl, hydroxy $C_1$-$C_6$ alkyl, $C_1$-$C_6$ alkoxy, phenyloxy$C_1$-$C_6$ alkyl, naphthyloxy$C_1$-$C_6$ alkyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —$C_0$-$C_6$ alkyl-OC(O)NR'R", —$C_0$-$C_6$ alkyl-NR'R", hydroxyl, —$C_1$-$C_6$ alkyl-OC(O)-piperidinyl, —$C_1$-$C_6$ alkyl-OC(O)-pyrrolidinyl, —$C_1$-$C_6$ alkyl-OC (O)-morpholinyl, wherein each aryl, heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, $C_1$-$C_6$ alkanoyl, —C(O)NR'R", —NR'R", —O—$(CH_2)_{1-2}$—O—, —$CO_2R'$, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 4a, i.e., compounds of Formula I wherein $R_2$ and $R_{2a}$, are independently hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$ cycloalkyl, $C_3$-$C_6$ cycloalkyl$C_1$-$C_6$ alkyl, phenyl, naphthyl, phenyl$C_1$-$C_6$ alkyl, naphthyl$C_1$-$C_6$ alkyl, pyridyl, thiazolyl, pyrimidyl, pyrazolyl, —$CO_2R'$, CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, thiazolyloxy $C_1$-$C_6$ alkyl, —$C_0$-$C_6$ alkyl-OC(O)NR'R", —$C_0$-$C_6$ alkyl-NR'R", hydroxyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each aryl, heteroaryl, and heterocycloalkyl group is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In another aspect, the invention provides compounds of formula 5, i.e., compounds of formula 4 where the A-ring is phenyl or naphthyl, each of which is optionally substituted at a substitutable position with halogen, $C_1$-$C_6$ alkyl, $C_1$-$C_6$ alkoxy, $C_1$-$C_6$ haloalkyl, $C_1$-$C_6$ haloalkoxy, hydroxyl, CN, phenyloxy, benzyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl; and the B-ring is pyrazolyl, imidazolyl, pyrrolyl, triazolyl, pyrrolidinyl, pyrazolidinyl, imidazolidinyl, triazolopyrimidyl, imidazopyrimidyl, pyrazolopyrimidyl, isoxazolyl, indolyl, pyrimidyl, or pyridyl, each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, benzyl or phenyl, where the cyclic portions of the benzyl or phenyl groups are optionally substituted with 1 to 5 groups that are independently halogen, hydroxyl, $C_1$-$C_6$ alkyl, $C_1$-$C_6$ alkoxy, $C_1$-$C_4$ haloalkyl, $C_1$-$C_4$ haloalkoxy, $C_1$-$C_6$ alkanoyl, —NR'R", —$CO_2R'$, —CONR'R", CN or $NO_2$.

In another aspect, the invention provides compounds of formula 6, i.e., compounds of formula 5 having the formula:

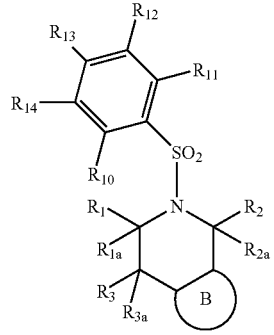

Formula 6 wherein, $R_{12}$ is H, halogen, $C_1$-$C_6$ alkyl, $C_1$-$C_6$ alkoxy, $C_1$-$C_6$ haloalkyl, or CN;

$R_{13}$ is H, halogen, $C_1$-$C_6$ alkyl optionally substituted with —$CO_2$—($C_1$-$C_6$ alkyl), $C_1$-$C_6$ alkoxy, $C_1$-$C_6$ haloalkyl, $C_1$-$C_6$ haloalkoxy, CN, aryloxy, isocyanato, —$SO_2$—($C_1$-$C_6$ alkyl), —NR'R", $C_1$-$C_6$ alkanoyl, pyridyl, or phenyl; or $R_{14}$ is H, $C_1$-$C_4$ alkyl, —$SO_2$—NR'R", or halogen;

where R' and R" are independently H or $C_1$-$C_6$ alkyl; or $R_{13}$ and $R_{14}$ and the carbons to which they are attached form a benzo ring; or $R_{10}$ and $R_{11}$ at each occurrence are independently H, halogen, or $C_1$-$C_6$ alkyl, where the alkyl is optionally substituted with a phenyl, where the phenyl is optionally substituted with 1 to 5 groups that are independently halogen, hydroxyl, $C_1$-$C_6$ alkyl, $C_1$-$C_6$ alkoxy, $C_1$-$C_4$ haloalkyl, $C_1$-$C_4$ haloalkoxy, CN or $NO_2$; or $R_{10}$, $R_{14}$, and the carbons to which they are attached form a benzo ring.

In still another aspect, the invention provides compounds of formula 6-1, i.e., compounds of formula 6 wherein the B-ring is pyrazolyl, imidazolyl, pyrrolyl, triazolyl, pyrrolidinyl, pyrazolidinyl, imidazolidinyl, isoxazolyl, pyrimidyl, or pyridyl, each of which is unsubstituted.

In still another aspect, the invention provides compounds of formula 6-2, i.e., compounds of formula 6 wherein the B-ring has the formula:

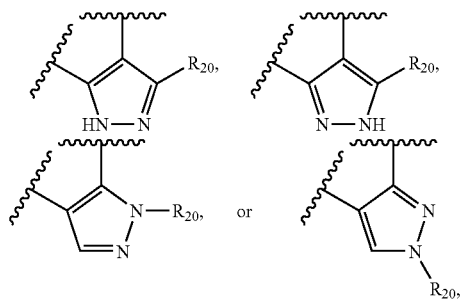

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, $C_1$-$C_6$ alkythio, halo, $CF_3$, or phenyl.

In yet another aspect, the invention provides compounds of formula 6-3, i.e., compounds of formula 6 wherein the B-ring has the formula:

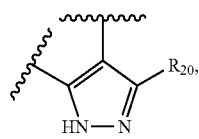

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In yet another aspect, the invention provides compounds of formula 6-4, i.e., compounds of formula 6 wherein the B-ring has the formula:

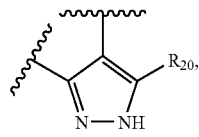

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In yet another aspect, the invention provides compounds of formula 6-5, i.e., compounds of formula 6 wherein the B-ring has the formula:

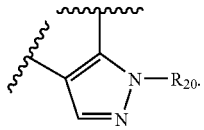

In yet another aspect, the invention provides compounds of formula 6-6, i.e., compounds of formula 6 wherein the B-ring has the formula:

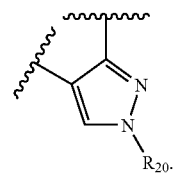

In still another aspect, the invention provides compounds of formula 6-6a, i.e., compounds according to any one of formulas 6-3, 6-4, 6-5, or 6-6, where $R_{20}$ is H, or $C_1$-$C_6$ alkyl. In another embodiment, $R_{20}$ is phenyl. In still another embodiment, when the $R_{20}$ group is attached to a carbon, $R_{20}$ is $C_1$-$C_4$ alkoxy, $C_1$-$C_4$ alkythio, halo, $CF_3$, or phenyl. In yet another embodiment, $R_{20}$ is H.

In yet another aspect, the invention provides compounds of formula 6-7, i.e., compounds of formula 6 wherein the B-ring has the formula:

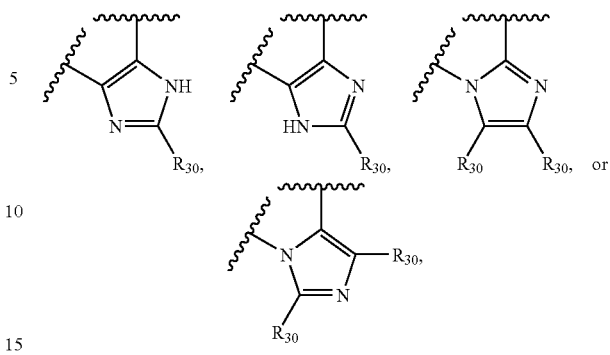

wherein $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still yet another aspect, the invention provides compounds of formula 6-8, i.e., compounds of formula 6 wherein the B-ring has the formula:

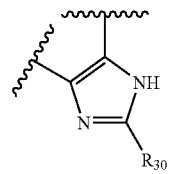

wherein $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In yet another aspect, the invention provides compounds of formula 6-9, i.e., compounds of formula 6 wherein the B-ring has the formula:

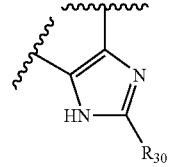

wherein $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In yet another aspect, the invention provides compounds of formula 6-10, i.e., compounds of formula 6 wherein the B-ring has the formula:

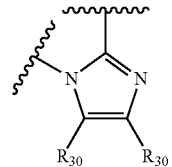

wherein R$_{30}$ is H, C$_1$-C$_4$ alkyl, C$_1$-C$_4$ alkoxy, amino, C$_1$-C$_4$ alkylamino, C$_1$-C$_4$ dialkylamino, C$_1$-C$_4$ alkythio, halo, CF$_3$, or phenyl.

In yet another aspect, the invention provides compounds of formula 6-11, i.e., compounds of formula 6 wherein the B-ring has the formula:

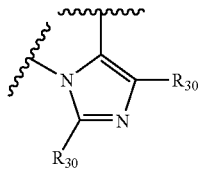

wherein R$_{30}$ is H, C$_1$-C$_4$ alkyl, C$_1$-C$_4$ alkoxy, amino, C$_1$-C$_4$ alkylamino, C$_1$-C$_4$ dialkylamino, C$_1$-C$_4$ alkythio, halo, CF$_3$, or phenyl.

In still another aspect, the invention provides compounds of formula 6-11a, i.e., compounds according to any one of formulas 6-8, 6-9, or 6-10, where R$_{30}$ is H, or C$_1$-C$_6$ alkyl. In another embodiment, R$_{30}$ is phenyl. In still another embodiment, when the R$_{30}$ group is attached to a carbon, R$_{30}$ is C$_1$-C$_4$ alkoxy, C$_1$-C$_4$ alkylthio, halo, CF$_3$, or phenyl. In yet another embodiment, R$_{30}$ is H.

In another aspect, the invention provides compounds of formula 6-11b, i.e., compounds according to any one of formulas 6-8, 6-9, or 6-10, where R$_{30}$ is amino, C$_1$-C$_4$ alkylamino, C$_1$-C$_4$ dialkylamino.

In yet still another aspect, the invention provides compounds of formula 6-12, i.e., compounds of formula 6 wherein the B-ring has the formula:

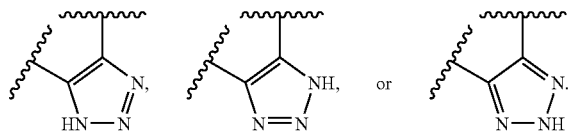

In yet another aspect, the invention provides compounds of formula 6-13, i.e., compounds of formula 6 wherein the B-ring has the formula:

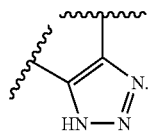

In yet another aspect, the invention provides compounds of formula 6-14, i.e., compounds of formula 6 wherein the B-ring has the formula:

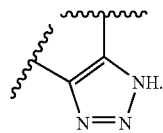

In yet another aspect, the invention provides compounds of formula 6-15, i.e., compounds of formula 6 wherein the B-ring has the formula:

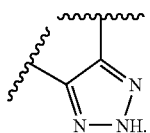

In still another aspect, the invention provides compounds of formula 7, i.e., compounds of formula 6 or any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15 wherein R$_1$ is C$_1$-C$_6$alkyl, C$_3$-C$_6$cycloalkyl, C$_3$-C$_6$cycloalkylalkyl, phenyl, biphenyl, phenylC$_1$-C$_6$ alkyl (such as benzyl or phenethyl), phenyloxyC$_1$-C$_6$ alkyl, or naphthyloxyC$_1$-C$_6$ alkyl, wherein each aryl group is optionally substituted with 1, 2, 3, 4, or 5 groups that are independently halogen, C$_1$-C$_6$ alkyl, C$_1$-C$_6$ alkoxy, halo C$_1$-C$_4$ alkyl, halo C$_1$-C$_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and R$_{1a}$ and R$_{2a}$ are both H.

In yet another aspect, the invention provides compounds of formula 7a, i.e., compounds of formula 7, wherein R$_2$ is hydrogen, halogen, C$_1$-C$_6$ alkyl, C$_2$-C$_6$ alkenyl, where the alkenyl group is optionally substituted with one or more halogens; C$_2$-C$_6$ alkynyl, C$_3$-C$_6$cycloalkyl, C$_3$-C$_6$cycloalkylC$_1$-C$_6$ alkyl, phenyl, naphthyl, phenylC$_1$-C$_6$ alkyl, naphthylC$_1$-C$_6$ alkyl, wherein each aryl group is optionally substituted with 1, 2, 3, 4, or 5 groups that are independently halogen, C$_1$-C$_6$ alkyl, C$_1$-C$_6$ alkoxy, C$_1$-C$_6$alkanoyl, halo C$_1$-C$_4$ alkyl, halo C$_1$-C$_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 7b, i.e., compounds of formula 7, wherein R$_2$ is hydrogen, pyridyl, thiazolyl, pyrimidyl, pyrazolyl, pyridyloxy C$_0$-C$_6$ alkyl, pyrimidyloxy C$_1$-C$_6$ alkyl, thienyloxy C$_1$-C$_6$ alkyl, pyrrolyloxy C$_1$-C$_6$ alkyl, or thiazolyloxy C$_1$-C$_6$ alkyl, or —C$_0$-C$_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, C$_1$-C$_6$ alkyl, C$_1$-C$_6$ alkoxy, C$_1$-C$_6$alkanoyl, halo C$_1$-C$_4$ alkyl, halo C$_1$-C$_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 7c, i.e., compounds of formula 7, wherein R$_2$ is hydrogen, —CO$_2$R', CONR'R", C$_1$-C$_6$ haloalkyl, where the haloalkyl group is optionally substituted with C$_1$-C$_4$ alkoxy; C$_1$-C$_4$ haloalkoxyalkyl, hydroxy C$_1$-C$_6$ alkyl, C$_2$-C$_6$ alkanoyl, phenyloxyC$_1$-C$_6$ alkyl, naphthyloxyC$_1$-C$_6$ alkyl, —C$_0$-C$_6$ alkyl-OC(O)NR'R", or —C$_0$-C$_6$ alkyl-NR'R", wherein each aryl group is optionally substituted with 1, 2, 3, 4, or 5 groups that are independently halogen, C$_1$-C$_6$ alkyl, C$_0$-C$_6$ alkoxy, C$_1$-C$_6$alkanoyl, halo C$_1$-C$_4$ alkyl, halo C$_1$-C$_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 7d, i.e., compounds of formula 7, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In another aspect, the invention provides compounds of formula 7-1, i.e., compounds of formula 6 or any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is pyridyl, thiazolyl, imidazolyl, benzofuranyl, benzothienyl, benzimidazolyl, quinolinyl, isoquinolinyl, quinoxalinyl, quinazolinyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —$C_1$-$C_6$ alkyl-OC(O)NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 7-1a, i.e., compounds of formula 7-1, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkylC$_1$-$C_6$ alkyl, phenyl, naphthyl, phenylC$_1$-$C_6$ alkyl, naphthylC$_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 7-1b, i.e., compounds of formula 7-1, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 7-1c, i.e., compounds of formula 7-1, wherein $R_2$ is hydrogen, —$CO_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxyC$_1$-$C_6$ alkyl, naphthyloxyC$_1$-$C_6$ alkyl, —$C_0$-$C_6$ alkyl-OC(O)NR'R", or —$C_0$-$C_6$ alkyl-NR'R" wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 7-1d, i.e., compounds of formula 7-1, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In another aspect, the invention provides compounds of formula 7-2, i.e., compounds of formula 7-1, 7-1a, 7-1b, 7-1c, or 7-1d, wherein $R_1$ is pyridyl, thiazolyl, imidazolyl, benzofuranyl, benzothienyl, benzimidazolyl, quinolinyl, isoquinolinyl, quinoxalinyl, or quinazolinyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 7-3, i.e., compounds of formula 7-1, 7-1a, 7-1b, 7-1c, or 7-1d, wherein $R_1$ is pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, or quinazolinyloxy $C_1$-$C_6$ alkyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In another aspect, the invention provides compounds of formula 7-4, i.e., compounds of formula 7-1, 7-1a, 7-1b, 7-1c, or 7-1d, wherein $R_1$ is —$C_0$-$C_6$ alkyl-OC(O)NR'R", —$C_0$-$C_6$ alkyl-NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In another aspect, the invention provides compounds of formula 7-5, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is —$CO_2R'$, —$CONR'R''$, $C_1$-$C_4$ haloalkyl, or $C_1$-$C_4$ hydroxyalkyl; and $R_{1a}$ and $R_{2a}$ are both H. In one embodiment, $R_1$ is as defined above and $R_2$ is H. In another embodiment, $R_1$ is as defined above and $R_2$ is methyl, ethyl, or cyclopropyl. In still another embodiment, $R_1$ is as defined above and $R_2$ is $C_1$-$C_4$ hydroxyalkyl. In a further embodiment, $R_1$ and $R_2$ are independently —$CO_2$—$C_1$-$C_4$ alkyl. In another embodiment, $R_1$ and $R_2$ are independently $C_1$-$C_2$ hydroxyalkyl. In yet another embodiment, $R_1$ is $C_1$-$C_2$ hydroxyalkyl and $R_2$ is methyl or ethyl.

In a further aspect, the invention provides compounds of formula 7-6, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is H or $C_1$-$C_6$ alkoxy, $R_2$ is H or $C_1$-$C_6$ alkoxy, and $R_{1a}$ and $R_{2a}$ are both H. In one embodiment, $R_1$ is $C_1$-$C_6$ alkoxy and $R_2$ is H or $C_1$-$C_6$ alkoxy. In another embodiment $R_1$ and $R_2$ are independently $C_{1-16}$ alkoxy. In yet another embodiment $R_1$ and $R_2$ are both H.

In another aspect, the invention provides compounds of formula 7-7, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_2$ are both $C_2$-$C_4$ alkenyl optionally substituted with one or more halogens (such as F or Cl), and $R_{1a}$ and $R_{2a}$ are both H. In one embodiment, $R_1$ and $R_2$ are the same. In a further embodiment, $R_1$ and $R_2$ are both $C_2$ alkenyl substituted with two halogens (such as F). $R_1$ and $R_2$ may be cis or trans relative to each other.

In another aspect, the invention provides compounds of formula 7-8, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are the same and are —$CH_2F$, —$CH_2CF_3$, —$CH_2CHF_2$, $CF_3$, or —$CF_2CH_3$.

In another aspect, the invention provides compounds of formula 7-9, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_2$ are both benzyl or phenethyl, and $R_{1a}$ and $R_{2a}$ are both H. $R_1$ and $R_2$ may be cis or trans relative to each other. In one embodiment, $R_1$ and $R_2$ are both benzyl.

In another aspect, the invention provides compounds of formula 7-10, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_2$ are both H or $C_1$-$C_4$ alkyl and $R_{1a}$ and $R_{2a}$ are both H. $R_1$ and $R_2$ may be cis or trans relative to each other. In one embodiment, $R_1$ and $R_2$ are both methyl. In another embodiment, both $R_1$ and $R_2$ are both isopropyl. In still another embodiment, one or $R_1$ and $R_2$ is methyl while the other is isopropyl. In yet another embodiment, both of $R_1$ and $R_2$ are ethyl.

In another aspect, the invention provides compounds of formula 7-11, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is H, $C_1$-$C_4$ alkyl, benzyl, phenethyl, or phenyl, where the phenyl portions of $R_1$ are optionally substituted with 1, 2, or 3 groups that are independently halogen, $C_1$-$C_4$ alkyl, or $C_1$-$C_4$ alkoxy and $R_2$ is H or $C_1$-$C_4$ alkyl, and $R_{1a}$ and $R_{2a}$ are both H. $R_1$ and $R_2$ may be cis or trans relative to each other.

In one aspect, the invention provides compounds of formula 7-12, i.e., compounds of formula 7-11 where, $R_2$ is H and $R_1$ is methyl, ethyl or propyl (n or iso), or $R_1$ is H and $R_2$ is methyl, ethyl or propyl (n or iso). In one embodiment, only one of $R_1$ and $R_2$ is isopropyl. In another embodiment, only one of $R_1$ and $R_2$ is ethyl.

In still another aspect, the invention provides compounds of formula 7-13, i.e., compounds of formula 7-11 where, $R_2$ is H and $R_1$ is phenyl substituted with one or two halogens (such as F or Cl), or $R_1$ is H and $R_2$ is phenyl substituted with one or two halogens (such as F or Cl)

In one aspect, the invention provides compounds of formula 7-14, i.e., compounds of formula 7-11 where, $R_2$ is H and $R_1$ is benzyl substituted with one or two groups that are independently halogen (such as F or Cl), methyl, ethyl, methoxy, or ethoxy.

In yet another aspect, the invention provides compounds of formula 7-15, i.e., compounds of formula 7-11 where, $R_2$ is methyl or ethyl, and $R_1$ is methyl, ethyl or propyl (n or iso). In one embodiment, $R_1$ and $R_2$ are both ethyl.

In still yet another aspect, the invention provides compounds of formula 7-16, i.e., compounds of formula 7-11 where, $R_2$ is methyl or ethyl, and $R_1$ is phenyl substituted with one or two halogens (such as F or Cl).

In yet another aspect, the invention provides compounds of formula 7-17, i.e., compounds of formula 7-11 where, $R_2$ is methyl or ethyl, and $R_1$ is benzyl substituted with one or two groups that are independently halogen (such as F or Cl), methyl, ethyl, methoxy, or ethoxy.

In another aspect, the invention provides compounds of formula 7-18, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_2$ are independently H or —$CO_2$—$C_1$-$C_4$ alkyl, and $R_{1a}$ and $R_{2a}$ are both H. $R_1$ and $R_2$ may be cis or trans relative to each other. In one embodiment, $R_1$ is —$CO_2$—$C_1$-$C_2$ alkyl and $R_2$ is H. In another embodiment, $R_1$ is —$CO_2$-Et and $R_2$ is H. In still another embodiment, $R_1$ is H and $R_2$ is —$CO_2$—$C_1$-$C_2$ alkyl. In yet another embodiment, $R_1$ and $R_2$ are both —$CO_2$-Et.

In another aspect, the invention provides compounds of formula 7-19, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ and $R_3$ form a double bond and $R_{1a}$ and $R_{3a}$ are both H. In one embodiment, $R_2$ is H. In another embodiment, $R_2$ is —$CO_2$—$C_1$-$C_4$ alkyl. In yet another embodiment, $R_2$ is —$CO_2$-Et. In still another embodiment, $R_2$ is methyl or ethyl. In still yet another embodiment, $R_2$ is thiazolyl, pyridyl or pyrimidyl.

In still another aspect, the invention provides compounds of formula 7-20, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is pyridyl, pyrimidyl, $C_3$-$C_6$ cycloalkyl, or thienyl, $R_2$ is H, $C_1$-$C_4$ alkyl, or $C_3$-$C_6$ cycloalkyl, and $R_{1a}$ and $R_{2a}$ are both H. $R_1$ and $R_2$ may be cis or trans relative to each other.

In yet still another aspect, the invention provides compounds of formula 7-21, i.e., compounds of formula 7-20 where, $R_1$ is pyridyl and $R_2$ is H.

In yet another aspect, the invention provides compounds of formula 7-22, i.e., compounds of formula 7-20 where, $R_1$ is pyridyl and $R_2$ is methyl or ethyl.

In a further aspect, the invention provides compounds of formula 7-23, i.e., compounds of formula 7-20 where, $R_1$ is pyridyl and $R_2$ is $C_3$, $C_5$, or $C_6$ cycloalkyl. In another embodiment, $R_2$ is $C_3$ cycloalkyl.

In still another aspect, the invention provides compounds of formula 7-24, i.e., compounds of formula 7-20 where, $R_1$ is pyrimidyl and $R_2$ is H.

In another aspect, the invention provides compounds of formula 7-25, i.e., compounds of formula 7-20 where, $R_1$ is pyrimidyl and $R_2$ is methyl or ethyl.

In yet another aspect, the invention provides compounds of formula 7-26, i.e., compounds of formula 7-20 where, $R_1$ is pyrimidyl and $R_2$ is $C_3$, $C_5$, or $C_6$ cycloalkyl.

In still another aspect, the invention provides compounds of formula 7-27, i.e., compounds of formula 7-20 where, $R_1$ is $C_3$, $C_5$, or $C_6$ cycloalkyl and $R_2$ is H.

In yet still another aspect, the invention provides compounds of formula 7-28, i.e., compounds of formula 7-20 where, $R_1$ is $C_3$, $C_5$, or $C_6$ cycloalkyl and $R_2$ is methyl or ethyl.

In yet another aspect, the invention provides compounds of formula 7-29, i.e., compounds of formula 7-20 where, $R_1$ is $C_3$, $C_5$, or $C_6$ cycloalkyl and $R_2$ is $C_3$, $C_5$, or $C_6$ cycloalkyl. In one embodiment one of $R_1$ and $R_2$ is $C_3$ cycloalkyl. In another embodiment, both of $R_1$ and $R_2$ are $C_3$ cycloalkyl.

In still another aspect, the invention provides compounds of formula 7-30, i.e., compounds of formula 7-20 where, $R_1$ is thienyl and $R_2$ is H.

In yet another aspect, the invention provides compounds of formula 7-31, i.e., compounds of formula 7-20 where, $R_1$ is thienyl and $R_2$ is methyl or ethyl.

In yet another aspect, the invention provides compounds of formula 7-32, i.e., compounds of formula 7-20 where, $R_1$ is thienyl and $R_2$ is $C_3$, $C_5$, or $C_6$ cycloalkyl. In one embodiment, $R_2$ is $C_3$ cycloalkyl.

In a further aspect, the invention provides compounds of formula 7-33, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_2$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_1$ is H, methyl, or ethyl; where R' and R" are independently H or $C_1$-$C_4$ alkyl. When $R_1$ is methyl or ethyl, $R_1$ and $R_2$ may be cis or trans relative to each other.

In still another aspect, the invention provides compounds of formula 7-34, i.e., compounds of formula 7-33 where, $R_2$ is pyridyl, pyrimidyl, thiazolyl, benzimidazolyl, or imidazolyl. In one embodiment, $R_2$ is thiazolyl and $R_1$ is H. In another embodiment, $R_2$ is thiazolyl and $R_1$ is methyl or ethyl. In still another embodiment, $R_2$ is pyridyl and $R_1$ is H. In another embodiment, $R_2$ is pyridyl and $R_1$ is methyl or ethyl. In yet another embodiment, $R_2$ is pyrimidyl and $R_1$ is H. In another embodiment, $R_2$ is pyrimidyl and $R_1$ is methyl or ethyl.

In yet another aspect, the invention provides compounds of formula 7-35, i.e., compounds of formula 7-33 where, $R_2$ is —$CO_2$-Me or —$CO_2$-Et.

In yet another aspect, the invention provides compounds of formula 7-36, i.e., compounds of formula 7-33 where, $R_2$ is methyl, ethyl, or propyl (either n or iso).

In yet another aspect, the invention provides compounds of formula 7-37, i.e., compounds of formula 7-33 where, $R_2$ is —$CH_2$—OC(O)NR'R", where R' and R" are independently H or $C_1$-$C_2$ alkyl. In one embodiment, $R_1$ is H. In another embodiment, $R_1$ is ethyl.

In yet still another aspect, the invention provides compounds of formula 7-38, i.e., compounds according to any one of formulas 6-1, 6-2, 6-3, 6-4, 6-5, 6-6, 6-6a, 6-7, 6-8, 6-9, 6-10, 6-11, 6-11b, 6-12, 6-13, 6-14, or 6-15, wherein $R_2$ and $R_{2a}$ combine to form oxo.

In still another aspect, the invention provides compounds of formula 7-39, i.e., compounds of formula 7-38 where, $R_1$ is H, $C_1$-$C_4$ alkyl, $C_3$-$C_6$ cycloalkyl, or —$C_1$-$C_4$ alkyl-OC(O)NR'R", where R' and R" are independently H or $C_1$-$C_4$ alkyl, and $R_{1a}$ is H.

In still another aspect, the invention provides compounds of formula 7-40, i.e., compounds of formula 7-38 where, $R_1$ is H, methyl or ethyl. In one embodiment, $R_1$ is H. In another embodiment, $R_1$ is methyl or ethyl.

In yet another aspect, the invention provides compounds of formula 7-41, i.e., compounds of formula 7-38 where, $R_1$ is $C_3$, $C_5$, or $C_6$ cycloalkyl. In one embodiment, $R_1$ is $C_3$ cycloalkyl. In another embodiment, $R_1$ is $C_5$ or $C_6$ cycloalkyl.

In still yet another aspect, the invention provides compounds of formula 7-42, i.e., compounds of formula 7-38 where, $R_1$ is —$C_1$-$C_2$ alkyl-OC(O)NR'R", where R' and R" are independently H, methyl, or ethyl.

In yet still another aspect, the invention provides compounds of formula 7-43, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_3$ is NR'R", OH, halogen, $R_{3a}$ is H or halogen; or $R_3$ and $R_{3a}$ combine to form oxo, =N—OH, or =N—O—$C_1$-$C_4$ alkyl. $R_1$ is H, pyridyl, pyrimidyl, $C_1$-$C_4$ alkyl; $R_2$ is H, $C_1$-$C_4$ alkyl, pyrimidyl, pyridyl, thiazolyl, or imidazolyl; and $R_1$, and $R_{2a}$ are both H.

In still yet another aspect, the invention provides compounds of formula 7-44, i.e., compounds of formula 7-43 where, $R_3$ is NR'R"; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In still yet another aspect, the invention provides compounds of formula 7-45, i.e., compounds of formula 7-43 where, $R_3$ is NR'R"; $R_{3a}$ is H; and $R_1$ is H, methyl, ethyl or propyl (n or iso); and $R_2$ is H, pyrimidyl, pyridyl, thiazolyl, or imidazolyl. In one embodiment, $R_1$ is H and $R_2$ is pyrimidyl or pyridyl. In another embodiment, $R_1$ is H and $R_2$ is thiazolyl, or imidazolyl. In one embodiment, $R_1$ is methyl, ethyl or propyl (n or iso) and $R_2$ is pyrimidyl or pyridyl. In another embodiment, $R_1$ is methyl, ethyl or propyl (n or iso) and $R_2$ is thiazolyl, or imidazolyl.

In another aspect, the invention provides compounds of formula 7-46, i.e., compounds of formula 7-43 where, $R_3$ is NR'R"; $R_{3a}$ is H; and $R_1$ is pyridyl or pyrimidyl; and $R_2$ is H.

In still yet another aspect, the invention provides compounds of formula 7-47, i.e., compounds of formula 7-43 where, $R_3$ is NR'R"; $R_{3a}$ is H; $R_1$ is pyridyl, or pyrimidyl; and $R_2$ is pyrimidyl, pyridyl, thiazolyl, or imidazolyl.

In another aspect, the invention provides compounds of formula 7-48, i.e., compounds of formula 7-43 where $R_1$ is H and $R_2$ is methyl, ethyl or propyl (n or iso). In another embodiment $R_2$ is methyl. In yet another embodiment $R_2$ is ethyl. In another embodiment $R_2$ is propyl (n or iso).

In another aspect, the invention provides compounds of formula 7-49, i.e., compounds of formula 7-43 where $R_2$ is H and $R_1$ is methyl, ethyl or propyl (n or iso). In another embodiment $R_1$ is methyl. In yet another embodiment $R_1$ is ethyl. In another embodiment $R_1$ is propyl (n or iso).

In still yet another aspect, the invention provides compounds of formula 7-50, i.e., compounds of formula 7-43 where, $R_3$ is halogen; $R_{3a}$ is H or halogen; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other. In still another embodiment $R_3$ and $R_{3a}$ are the same. When $R_3$ and $R_{3a}$ are the same, they may both be F.

In still yet another aspect, the invention provides compounds of formula 7-51, i.e., compounds of formula 7-43 where, $R_3$ is OH; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In yet still another aspect, the invention provides compounds of formula 7-52, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_3$ and $R_{3a}$ combine to form oxo, =N—OH, or =N—O—$C_1$-$C_4$ alkyl; $R_1$ is H, pyridyl, pyrimidyl, $C_1$-$C_4$ alkyl (methyl, ethyl), or $C_3$-$C_6$ cycloalkyl; $R_2$ is H, $C_1$-$C_4$ alkyl (methyl, ethyl, isopropyl), pyrimidyl, pyridyl, thiazolyl, or imidazolyl; and $R_{1a}$ and $R_{2a}$ are both H.

In another aspect, the invention provides compounds of formula 7-53, i.e., compounds of formula 7-52 where, $R_3$ and $R_{3a}$ combine to form oxo; and $R_1$ is $C_3$-$C_6$ cycloalkyl, pyridyl or pyrimidyl.

In yet another aspect, the invention provides compounds of formula 7-54, i.e., compounds of formula 7-53 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 7-55, i.e., compounds of formula 7-52 where, $R_3$ and $R_{3a}$ combine to form oxo; and $R_1$ is H or $C_1$-$C_4$ alkyl (such as methyl, ethyl or isopropyl).

In another aspect, the invention provides compounds of formula 7-56, i.e., compounds of formula 7-55 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 7-57, i.e., compounds of formula 7-52 where, $R_1$ and $R_2$ are both H.

In still yet another aspect, the invention provides compounds of formula 7-58, i.e., compounds according to either formula 7-53 or 7-55 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 7-59, i.e., compounds of formula 7-52 where, $R_3$ and $R_{3a}$ combine to form =N—OH; and $R_1$ is $C_3$-$C_6$ cycloalkyl, pyridyl or pyrimidyl.

In yet another aspect, the invention provides compounds of formula 7-60, i.e., compounds of formula 7-59 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 7-61, i.e., compounds of formula 7-52 where, $R_3$ and $R_{3a}$ combine to form =N—OH; and $R_1$ is H or $C_1$-$C_4$ alkyl (such as methyl, ethyl or isopropyl).

In another aspect, the invention provides compounds of formula 7-62, i.e., compounds of formula 7-61 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 7-63, i.e., compounds according to either formula 7-59 or 7-61 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 7-64, i.e., compounds of formula 7-52 where, $R_3$ and $R_{3a}$ combine to form =N—O—$C_1$-$C_4$ alkyl; and $R_1$ is $C_3$-$C_6$ cycloalkyl, pyridyl or pyrimidyl.

In yet another aspect, the invention provides compounds of formula 7-65, i.e., compounds of formula 7-64 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 7-66, i.e., compounds of formula 7-52 where, $R_3$ and $R_{3a}$ combine to form =N—O—$C_1$-$C_4$ alkyl; and $R_1$ is H or $C_1$-$C_4$ alkyl (such as methyl, ethyl or isopropyl).

In another aspect, the invention provides compounds of formula 7-67, i.e., compounds of formula 7-66 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 7-68, i.e., compounds according to either formula 7-64 or 7-66 where, $R_2$ is pyrimidyl, pyridyl, thiazolyl, or imidazolyl, In one embodiment, $R_2$ is pyrimidyl or pyridyl. In another embodiment, $R_2$ is thiazolyl, or imidazolyl, In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In a further aspect, the invention provides compounds of formula 7-69, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_2$ is H, methyl, or ethyl; where R' and R" are independently H or $C_1$-$C_4$ alkyl. When $R_2$ is methyl or ethyl, $R_1$ and $R_2$ may be cis or trans relative to each other.

In still another aspect, the invention provides compounds of formula 7-70, i.e., compounds of formula 7-69 where, $R_1$ is pyridyl, pyrimidyl, thiazolyl, benzimidazolyl, or imidazolyl.

In yet another aspect, the invention provides compounds of formula 7-71, i.e., compounds of formula 7-69 where, $R_1$ is —$CO_2$-Me or —$CO_2$-Et.

In yet another aspect, the invention provides compounds of formula 7-72, i.e., compounds of formula 7-69 where, $R_1$ is methyl, ethyl, or propyl (either n or iso).

In yet another aspect, the invention provides compounds of formula 7-73, i.e., compounds of formula 7-69 where, $R_1$ is —$CH_2$—OC(O)NR'R", where R' and R" are independently H or $C_1$-$C_2$ alkyl In one embodiment, $R_2$ is H. In another embodiment, $R_2$ is ethyl.

In a further aspect, the invention provides compounds of formula 7-74, i.e., compounds according to any one of formulas 6-1, 6-2, 6-3, 6-4, 6-5, 6-6, 6-6a, 6-7, 6-8, 6-9, 6-10, 6-11, 6-11a, 6-11b, 6-12, 6-13, 6-14, or 6-15, wherein $R_1$ is —$C_1$-$C_4$ alkyl-OC(O)NR'R"; $R_2$ is H or —$C_1$-$C_4$ alkyl-OC(O)NR'R"; and $R_{1a}$, $R_2$, $R_3$, and $R_{3a}$ are H; where R' and R" are independently H or $C_1$-$C_3$ alkyl. In one embodiment, $R_1$ and $R_2$ are both —$CH_2$—OC(O)NR'R". In still another embodiment, R' and R" are both H, methyl or ethyl. In yet another embodiment, at least one of R' and R" is isopropyl.

In still yet another aspect, the invention provides compounds of formula 8, i.e., compounds according to any one of formulas 7 up to and including 7-74, wherein $R_{10}$, $R_{11}$, $R_{12}$, $R_{13}$, and $R_{14}$ are independently of each other H, halo, $CF_3$, $CHF_2$ or methyl.

In still yet another aspect, the invention provides compounds of formula 8-1, i.e., compounds of formula 8, wherein $R_{12}$ and $R_{14}$ are independently H, halo, or methyl.

In still yet another aspect, the invention provides compounds of formula 8-2, i.e., compounds of formula 8, wherein $R_{13}$ is H, halogen (in one aspect, F or Cl), $C_1$-$C_6$ alkyl optionally substituted with —$CO_2$—($C_1$-$C_6$ alkyl), $C_1$-$C_6$ alkoxy, $CF_3$, $OCF_3$, or CN.

In still yet another aspect, the invention provides compounds of formula 8-3, i.e., compounds of formula 8 wherein $R_{13}$ is phenyloxy, —$SO_2$—($C_1$-$C_6$ alkyl), —NR'R", $C_1$-$C_6$ alkanoyl, oxazolyl, pyrazolyl, thiazolyl, imidazolyl, pyridyl, furanyl thienyl, or phenyl.

In still yet another aspect, the invention provides compounds of formula 8-4, i.e., compounds of formula 8, wherein $R_{13}$ is —NR'R".

In still yet another aspect, the invention provides compounds of formula 8-5, i.e., compounds of formula 8, 8-1, 8-2, or 8-5, wherein $R_{13}$ is chloro.

In still yet another aspect, the invention provides compounds of formula 8-6, i.e., compounds of formula 8, 8-1, 8-2, or 8-5, wherein $R_{13}$ is fluoro.

In still yet another aspect, the invention provides compounds of formula 8-7, i.e., compounds of formula 8, 8-1, 8-2, or 8-5, wherein $R_{13}$ is $CF_3$.

In still yet another aspect, the invention provides compounds of formula 8-8, i.e., compounds of formula 8, 8-1, 8-2, or 8-5, wherein $R_{13}$ is $OCF_3$.

In still yet another aspect, the invention provides compounds of formula 8-9, i.e., compounds according to any one of formulas 8, 8-2, 8-3, 8-4, 8-5, 8-6, 8-7, or 8-8, wherein $R_{12}$, $R_{14}$ $R_{10}$ and $R_{11}$ are H.

In another aspect, the invention provides compounds of formula 9, i.e., compounds of formula 4, wherein the A-ring is $C_3$-$C_8$ cycloalkyl, which is optionally substituted at a substitutable position with halogen, $C_1$-$C_6$ alkyl, $C_1$-$C_6$ alkoxy, haloalkyl, haloalkoxy, hydroxyl, CN, aryloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_0$-$C_6$ alkyl; and the B-ring is pyrazolyl, imidazolyl, pyrrolyl, triazolyl, pyrrolidinyl, pyrazolidinyl, imidazolidinyl, isoxazolyl, pyrimidyl, or pyridyl, each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, or phenyl.

In still another aspect, the invention provides compounds of formula 10, i.e., compounds of formula 9 having the following formulas:

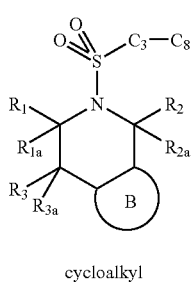

(formula 10)

cycloalkyl the cycloalkyl group is optionally substituted at a substitutable position with halogen, $C_1$-$C_6$ alkyl, $C_1$-$C_6$ alkoxy, haloalkyl, haloalkoxy, hydroxyl, CN, phenyloxy, benzyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 10-1, i.e., compounds of formula 10, wherein the B-ring is pyrazolyl, imidazolyl, pyrrolyl, triazolyl, pyrrolidinyl, pyrazolidinyl, imidazolidinyl, isoxazolyl, pyrimidyl or pyridyl, each of which is unsubstituted.

In still another aspect, the invention provides compounds of formula 10-2, i.e., compounds of formula 10, wherein the B-ring has the formula:

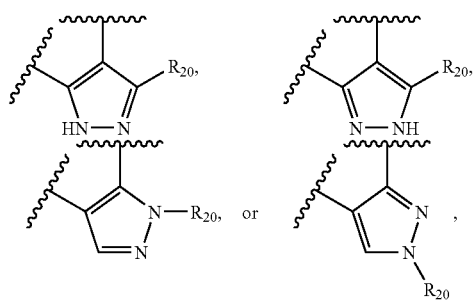

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, $C_1$-$C_6$ alkythio, halo, $CF_3$, or phenyl.

In still another aspect, the invention provides compounds of formula 10-3, i.e., compounds of formula 10, wherein the B-ring has the formula:

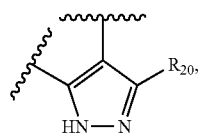

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 10-4, i.e., compounds of formula 10, wherein the B-ring has the formula:

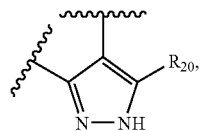

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 10-5, i.e., compounds of formula 10, wherein the B-ring has the formula:

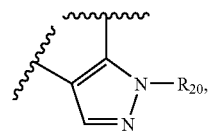

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 10-6, i.e., compounds of formula 10, wherein the B-ring has the formula:

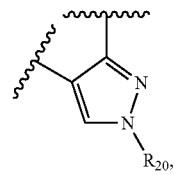

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 10-6a, i.e., compounds according to any one of formulas 10-3, 10-4, 10-5, or 10-6, where $R_{20}$ is H, or $C_1$-$C_6$ alkyl. In another embodiment, $R_{20}$ is phenyl. In still another embodiment, when the $R_{20}$ group is attached to a carbon, $R_{20}$ is $C_1$-$C_4$ alkoxy, $C_1$-$C_4$ alkythio, halo, $CF_3$, or phenyl. In yet another embodiment, $R_{20}$ is H.

In still another aspect, the invention provides compounds of formula 10-7, i.e., compounds of formula 10, wherein the B-ring has the formula:

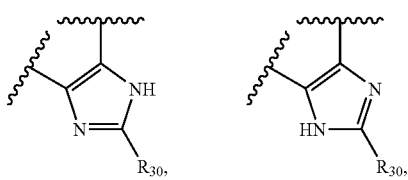

-continued

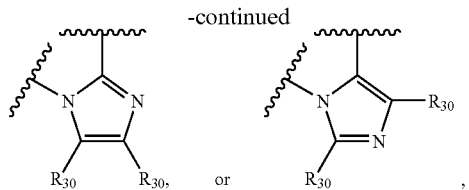

wherein $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 10-8, i.e., compounds of formula 10, wherein the B-ring has the formula:

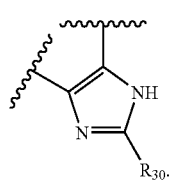

In still another aspect, the invention provides compounds of formula 10-9, i.e., compounds of formula 10, wherein the B-ring has the formula:

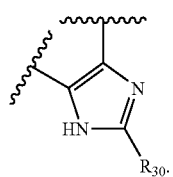

In still another aspect, the invention provides compounds of formula 10-10, i.e., compounds of formula 10, wherein the B-ring has the formula:

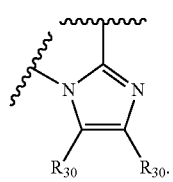

In still another aspect, the invention provides compounds of formula 10-11, i.e., compounds of formula 10, wherein the B-ring has the formula:

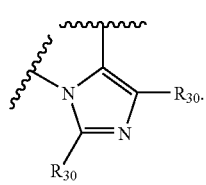

In still another aspect, the invention provides compounds of formula 10-11a, i.e., compounds according to any one of formulas 10-8, 10-9, or 10-10, where $R_{30}$ is H, or $C_1$-$C_6$ alkyl. In another embodiment, $R_{30}$ is phenyl. In still another embodiment, when the $R_{30}$ group is attached to a carbon, $R_{30}$ is $C_1$-$C_4$ alkoxy, $C_1$-$C_4$ alkythio, halo, $CF_3$, or phenyl. In yet another embodiment, $R_{30}$ is H.

In another aspect, the invention provides compounds of formula 10-11b, i.e., compounds according to any one of formulas 10-8, 10-9, or 10-10, where $R_{30}$ is amino, $C_1$-$C_4$ alkylamino, $C_1$-$C_4$ dialkylamino.

In still another aspect, the invention provides compounds of formula 10-12, i.e., compounds of formula 10, wherein the B-ring has the formula:

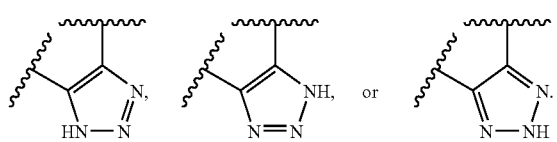

In still another aspect, the invention provides compounds of formula 10-13, i.e., compounds of formula 10, wherein the B-ring has the formula:

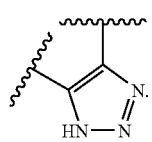

In still another aspect, the invention provides compounds of formula 10-14, i.e., compounds of formula 10, wherein the B-ring has the formula:

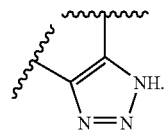

In still another aspect, the invention provides compounds of formula 10-15, i.e., compounds of formula 10, wherein the B-ring has the formula:

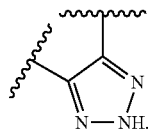

In yet another aspect, the invention provides compounds of formula 11, i.e., compounds of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, 10-15, wherein $R_1$ is $C_1$-$C_6$ alkyl, $C_3$-$C_6$ cycloalkyl, $C_3$-$C_6$ cycloalkylalkyl, phenyl, biphenyl, phenyl$C_1$-$C_6$ alkyl (such as benzyl or phenethyl), phenyloxy$C_1$-$C_6$ alkyl, or naphthyloxy$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_1$, and $R_{2a}$ are both H.

In yet another aspect, the invention provides compounds of formula 11a, i.e., compounds of formula 11, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11b, i.e., compounds of formula 11, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11c, i.e., compounds of formula 11, wherein $R_2$ is hydrogen, —$CO_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", or —$C_0$-$C_6$ alkyl-NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 11d, i.e., compounds of formula 11, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11-1, i.e., compounds of formulas 10, 10-1, 10-2, 10-3, 10-4, 10-5, 10-6, 10-6a, 10-7, 10-8, 10-9, 10-10, 10-11, 10-11a, 10-12, 10-13, 10-14, or 10-15, wherein $R_1$ is pyridyl, thiazolyl, imidazolyl, benzofuranyl, benzothienyl, benzimidazolyl, quinolinyl, isoquinolinyl, quinoxalinyl, quinazolinyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —$C_1$-$C_6$ alkyl-OC(O)NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_1$, and $R_{2a}$ are both H.

In yet another aspect, the invention provides compounds of formula 11-1a, i.e., compounds of formula 11-1, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11-1b, i.e., compounds of formula 11-1, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11-1c, i.e., compounds of formula 11-1, wherein $R_2$ is hydrogen, —$CO_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", or —$C_0$-$C_6$ alkyl-NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 11-1d, i.e., compounds of formula 11-1, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 11-2, i.e., compounds of formula 11-1, 11-1a, 11-1b, 11-1c, or 11-1d, wherein R$_1$ is pyridyl, thiazolyl, imidazolyl, benzofuranyl, benzothienyl, benzimidazolyl, quinolinyl, isoquinolinyl, quinoxalinyl, or quinazolinyl, wherein each heteroaryl group is optionally substituted with one or more groups that are independently halogen, C$_1$-C$_6$ alkyl, C$_1$-C$_6$ alkoxy, halo C$_1$-C$_4$ alkyl, halo C$_1$-C$_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and R$_{1a}$ and R$_{2a}$ are both H.

In yet another aspect, the invention provides compounds of formula 11-3, i.e., compounds of formula 11-1, 11-1a, 11-1b, 11-1c, or 11-1d, wherein R$_1$ is pyridyloxy C$_1$-C$_6$ alkyl, benzofuranyloxy C$_1$-C$_6$ alkyl, benzothienyloxy C$_1$-C$_6$ alkyl, quinolinyloxy C$_1$-C$_6$ alkyl, isoquinolinyloxy C$_1$-C$_6$ alkyl, quinoxalinyloxy C$_1$-C$_6$ alkyl, or quinazolinyloxy C$_1$-C$_6$ alkyl, wherein each heteroaryl group is optionally substituted with one or more groups that are independently halogen, C$_1$-C$_6$ alkyl, C$_1$-C$_6$ alkoxy, halo C$_1$-C$_4$ alkyl, halo C$_1$-C$_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and R$_{1a}$ and R$_{2a}$ are both H.

In yet another aspect, the invention provides compounds of formula 11-4, i.e., compounds of formula 11-1, 11-1a, 11-1b, 11-1c, or 11-1d, wherein R$_1$ is —C$_0$-C$_6$ alkyl-OC(O)NR'R", —C$_0$-C$_6$ alkyl-NR'R", —C$_1$-C$_6$ alkyl-OC(O)-piperidinyl, —C$_1$-C$_6$ alkyl-OC(O)-pyrrolidinyl, or —C$_1$-C$_6$ alkyl-OC(O)-morpholinyl, wherein each heterocycloalkyl group is optionally substituted with one or more groups that are independently halogen, C$_1$-C$_6$ alkyl, C$_1$-C$_6$ alkoxy, halo C$_1$-C$_4$ alkyl, halo C$_1$-C$_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and R$_{1a}$ and R$_{2a}$ are both H.

In yet another aspect, the invention provides compounds of formula 11-5, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ is —CO$_2$R', —CONR'R", C$_1$-C$_4$ haloalkyl, or C$_1$-C$_4$ hydroxyalkyl; and R$_{1a}$ and R$_{2a}$ are both H. In one embodiment, R$_1$ is as defined above and R$_2$ is H. In another embodiment, R$_1$ is as defined above and R$_2$ is methyl, ethyl, or cyclopropyl. In still another embodiment, R$_1$ is as defined above and R$_2$ is C$_1$-C$_4$ hydroxyalkyl. In a further embodiment, R$_1$ and R$_2$ are independently —CO$_2$—C$_1$-C$_4$ alkyl. In another embodiment, R$_1$ and R$_2$ are independently C$_1$-C$_2$ hydroxyalkyl. In yet another embodiment, R$_1$ is C$_1$-C$_2$ hydroxyalkyl and R$_2$ is methyl or ethyl.

In a further aspect, the invention provides compounds of formula 11-6, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ is H or C$_1$-C$_6$ alkoxy, R$_2$ is H or C$_1$-C$_6$ alkoxy, and R$_{1a}$ and R$_{2a}$ are both H. In one embodiment, R$_1$ is C$_1$-C$_6$ alkoxy and R$_2$ is H or C$_1$-C$_6$ alkoxy. In another embodiment R$_1$ and R$_2$ are independently C$_1$-C$_6$ alkoxy. In yet another embodiment R$_1$ and R$_2$ are both H.

In another aspect, the invention provides compounds of formula 11-7, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ and R$_2$ are both C$_2$-C$_4$ alkenyl optionally substituted with one or more halogens (such as F or Cl), and R$_{1a}$ and R$_{2a}$ are both H. In one embodiment, R$_1$ and R$_2$ are the same. In a further embodiment, R$_1$ and R$_2$ are both C$_2$ alkenyl substituted with two halogens (such as F). R$_1$ and R$_2$ may be cis or trans relative to each other.

In another aspect, the invention provides compounds of formula 11-8, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ and R$_2$ are both C$_0$-C$_2$ haloalkyl and R$_{1a}$ and R$_{2a}$ are both H. R$_1$ and R$_2$ may be cis or trans relative to each other. In one embodiment, R$_1$ and R$_2$ are the same and are —CH$_2$F, —CH$_2$CF$_3$, —CH$_2$CHF$_2$, CF$_3$, or —CF$_2$CH$_3$.

In another aspect, the invention provides compounds of formula 11-8, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ and R$_2$ are both benzyl or phenethyl, and R$_{1a}$ and R$_2$, are both H. R$_1$ and R$_2$ may be cis or trans relative to each other. In one embodiment, R$_1$ and R$_2$ are both benzyl.

In another aspect, the invention provides compounds of formula 11-10, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ and R$_2$ are both H or C$_1$-C$_4$ alkyl and R$_{1a}$, and R$_2$, are both H. R$_1$ and R$_2$ may be cis or trans relative to each other. In one embodiment, R$_1$ and R$_2$ are both methyl. In another embodiment, both R$_1$ and R$_2$ are both isopropyl. In still another embodiment, one or R$_1$ and R$_2$ is methyl while the other is isopropyl. In yet another embodiment, both of R$_1$ and R$_2$ are ethyl.

In another aspect, the invention provides compounds of formula 11-11, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein R$_1$ is H, C$_1$-C$_4$ alkyl, benzyl, phenethyl, or phenyl, where the phenyl portions of R$_1$ are optionally substituted with 1, 2, or 3 groups that are independently halogen, C$_1$-C$_4$ alkyl, or C$_1$-C$_4$ alkoxy and R$_2$ is H or C$_1$-C$_4$ alkyl, and R$_{1a}$ and R$_{2a}$ are both H. R$_1$ and R$_2$ may be cis or trans relative to each other.

In one aspect, the invention provides compounds of formula 11-12, i.e., compounds of formula 11-11 where, R$_2$ is H and R$_1$ is methyl, ethyl or propyl (n or iso), or R$_1$ is H and R$_2$ is methyl, ethyl or propyl (n or iso). In one embodiment, only one of R$_1$ and R$_2$ is isopropyl. In another embodiment, only one of R$_1$ and R$_2$ is ethyl.

In still another aspect, the invention provides compounds of formula 11-13, i.e., compounds of formula 11-11 where, R$_2$ is H and R$_1$ is phenyl substituted with one or two halogens (such as F or Cl), or R$_1$ is H and R$_2$ is phenyl substituted with one or two halogens (such as F or Cl)

In one aspect, the invention provides compounds of formula 11-14, i.e., compounds of formula 11-11 where, R$_2$ is H and R$_1$ is benzyl substituted with one or two groups that are independently halogen (such as F or Cl), methyl, ethyl, methoxy, or ethoxy.

In yet another aspect, the invention provides compounds of formula 11-15, i.e., compounds of formula 11-11 where, R$_2$ is methyl or ethyl, and $R_1$ is methyl, ethyl or propyl (n or iso). In one embodiment, $R_1$ and $R_2$ are both ethyl.

In still yet another aspect, the invention provides compounds of formula 11-16, i.e., compounds of formula 11-11 where, $R_2$ is methyl or ethyl, and $R_1$ is phenyl substituted with one or two halogens (such as F or Cl).

In yet another aspect, the invention provides compounds of formula 11-17, i.e., compounds of formula 11-11 where, $R_2$ is methyl or ethyl, and $R_1$ is benzyl substituted with one or two groups that are independently halogen (such as F or Cl), methyl, ethyl, methoxy, or ethoxy.

In another aspect, the invention provides compounds of formula 11-18, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_1$ and $R_2$ are independently H or —$CO_2$—$C_1$-$C_4$ alkyl, and $R_{1a}$ and $R_{2a}$ are both H. $R_1$ and $R_2$ may be cis or trans relative to each other. In one embodiment, $R_1$ is —$CO_2$—$C_1$-$C_2$ alkyl and $R_2$ is H. In another embodiment, $R_1$ is —$CO_2$-Et and $R_2$ is H. In still another embodiment, $R_1$ is H and $R_2$ is —$CO_2$—$C_1$-$C_2$ alkyl. In yet another embodiment, $R_1$ and $R_2$ are both —$CO_2$-Et.

In another aspect, the invention provides compounds of formula 11-19, i.e., compounds according to any one of formulas 10, 10-1, 10-2, 10-3, 10-4, 10-5, 10-6, 10-6a, 10-7, 10-8, 10-9, 10-10, 10-11, 10-1a, 10-11b, 10-12, 10-13, 10-14, or 10-15, wherein $R_1$ and $R_3$ form a double bond and $R_{1a}$ and $R_{3a}$ are both H. In one embodiment, $R_2$ is H. In another embodiment, $R_2$ is —$CO_2$—$C_1$-$C_4$ alkyl. In yet another embodiment, $R_2$ is —$CO_2$-Et. In still another embodiment, $R_2$ is methyl or ethyl. In still yet another embodiment, $R_2$ is thiazolyl, pyridyl or pyrimidyl.

In still another aspect, the invention provides compounds of formula 11-20, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_1$ is pyridyl, pyrimidyl, $C_3$-$C_6$ cycloalkyl, or thienyl, $R_2$ is H, $C_1$-$C_4$ alkyl, or $C_3$-$C_6$ cycloalkyl, and $R_{1a}$, and $R_{2a}$ are both H. $R_1$ and $R_2$ may be cis or trans relative to each other.

In yet still another aspect, the invention provides compounds of formula 11-21, i.e., compounds of formula 11-20 where, $R_1$ is pyridyl and $R_2$ is H.

In yet another aspect, the invention provides compounds of formula 11-22, i.e., compounds of formula 11-20 where, $R_1$ is pyridyl and $R_2$ is methyl or ethyl.

In a further aspect, the invention provides compounds of formula 11-23, i.e., compounds of formula 11-20 where, $R_1$ is pyridyl and $R_2$ is $C_3$, $C_5$, or $C_6$ cycloalkyl. In another embodiment, $R_2$ is $C_3$ cycloalkyl.

In still another aspect, the invention provides compounds of formula 11-24, i.e., compounds of formula 11-20 where, $R_1$ is pyrimidyl and $R_2$ is H.

In another aspect, the invention provides compounds of formula 11-25, i.e., compounds of formula 11-20 where, $R_1$ is pyrimidyl and $R_2$ is methyl or ethyl.

In yet another aspect, the invention provides compounds of formula 11-26, i.e., compounds of formula 11-20 where, $R_1$ is pyrimidyl and $R_2$ is $C_3$, $C_5$, or $C_6$ cycloalkyl.

In still another aspect, the invention provides compounds of formula 11-27, i.e., compounds of formula 11-20 where, $R_1$ is $C_3$, $C_5$, or $C_6$ cycloalkyl and $R_2$ is H.

In yet still another aspect, the invention provides compounds of formula 11-28, i.e., compounds of formula 11-20 where, $R_1$ is $C_3$, $C_5$, or $C_6$ cycloalkyl and $R_2$ is methyl or ethyl.

In yet another aspect, the invention provides compounds of formula 11-29, i.e., compounds of formula 11-20 where, $R_1$ is $C_3$, $C_5$, or $C_6$ cycloalkyl and $R_2$ is $C_3$, $C_5$, or $C_6$ cycloalkyl. In one embodiment one of $R_1$ and $R_2$ is $C_3$ cycloalkyl. In another embodiment, both of $R_1$ and $R_2$ are $C_3$ cycloalkyl.

In still another aspect, the invention provides compounds of formula 11-30, i.e., compounds of formula 11-20 where, $R_1$ is thienyl and $R_2$ is H.

In yet another aspect, the invention provides compounds of formula 11-31, i.e., compounds of formula 11-20 where, $R_1$ is thienyl and $R_2$ is methyl or ethyl.

In yet another aspect, the invention provides compounds of formula 11-32, i.e., compounds of formula 11-20 where, $R_1$ is thienyl and $R_2$ is $C_3$, $C_5$, or $C_6$ cycloalkyl. In one embodiment, $R_2$ is $C_3$ cycloalkyl.

In a further aspect, the invention provides compounds of formula 11-33, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_2$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_1$ is H, methyl, or ethyl; where R' and R" are independently H or $C_1$-$C_4$ alkyl. When $R_1$ is methyl or ethyl, $R_1$ and $R_2$ may be cis or trans relative to each other.

In still another aspect, the invention provides compounds of formula 11-34, i.e., compounds of formula 11-33 where, $R_2$ is pyridyl, pyrimidyl, thiazolyl, benzimidazolyl, or imidazolyl. In one embodiment, $R_2$ is thiazolyl and $R_1$ is H. In another embodiment, $R_2$ is thiazolyl and $R_1$ is methyl or ethyl. In still another embodiment, $R_2$ is pyridyl and $R_1$ is H. In another embodiment, $R_2$ is pyridyl and $R_1$ is methyl or ethyl. In yet another embodiment, $R_2$ is pyrimidyl and $R_1$ is H. In another embodiment, $R_2$ is pyrimidyl and $R_1$ is methyl or ethyl.

In yet another aspect, the invention provides compounds of formula 11-35, i.e., compounds of formula 11-33 where, $R_2$ is $CO_2$-Me or —$CO_2$-Et.

In yet another aspect, the invention provides compounds of formula 11-36, i.e., compounds of formula 11-33 where, $R_2$ is methyl, ethyl, or propyl (either n or iso).

In yet another aspect, the invention provides compounds of formula 11-37, i.e., compounds of formula 11-33 where, $R_2$ is —$CH_2$—OC(O)NR'R", where R' and R" are independently H or $C_1$-$C_2$ alkyl. In one embodiment, $R_1$ is H. In another embodiment, $R_1$ is ethyl.

In yet still another aspect, the invention provides compounds of formula 11-38, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_2$ and $R_{2a}$ combine to form oxo.

In still another aspect, the invention provides compounds of formula 11-39, i.e., compounds of formula 11-38 where, $R_1$ is H, $C_1$-$C_4$ alkyl, $C_3$-$C_6$ cycloalkyl, or —$C_1$-$C_4$ alkyl-OC(O)NR'R", where R' and R" are independently H or $C_1$-$C_4$ alkyl, and $R_{1a}$ is H.

In still another aspect, the invention provides compounds of formula 11-40, i.e., compounds of formula 11-38 where, $R_1$ is H, methyl or ethyl, In one embodiment, $R_1$ is H. In another embodiment, $R_1$ is methyl or ethyl.

In yet another aspect, the invention provides compounds of formula 11-41, i.e., compounds of formula 11-38 where, $R_1$ is $C_3$, $C_5$, or $C_6$ cycloalkyl, In one embodiment, $R_1$ is $C_3$ cycloalkyl. In another embodiment, $R_1$ is $C_5$ or $C_6$ cycloalky.

In still yet another aspect, the invention provides compounds of formula 11-42, i.e., compounds of formula 11-38 where, $R_1$ is —$C_1$-$C_2$ alkyl-OC(O)NR'R", where R' and R" are independently H, methyl, or ethyl.

In yet still another aspect, the invention provides compounds of formula 11-43, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_3$ is NR'R", OH, halogen, $R_{3a}$ is H or halogen; or $R_3$ and $R_{3a}$ combine to form oxo, =N—OH, or =N—O—$C_1$-$C_4$ alkyl. $R_1$ is H, pyridyl, pyrimidyl, $C_1$-$C_4$ alkyl; $R_2$ is H, $C_1$-$C_4$ alkyl, pyrimidyl, pyridyl, thiazolyl, or imidazolyl; and $R_{1a}$ and $R_{2a}$ are both H.

In still yet another aspect, the invention provides compounds of formula 11-44, i.e., compounds of formula 11-43 where, $R_3$ is NR'R"; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In still yet another aspect, the invention provides compounds of formula 11-45, i.e., compounds of formula 11-43 where, $R_3$ is NR'R"; $R_{3a}$ is H; and $R_1$ is H, methyl, ethyl or propyl (n or iso); and $R_2$ is H, pyrimidyl, pyridyl, thiazolyl, or imidazolyl. In one embodiment, $R_1$ is H and $R_2$ is pyrimidyl or pyridyl. In another embodiment, $R_1$ is H and $R_2$ is thiazolyl, or imidazolyl. In one embodiment, $R_1$ is methyl, ethyl or propyl (n or iso) and $R_2$ is pyrimidyl or pyridyl. In another embodiment, $R_1$ is methyl, ethyl or propyl (n or iso) and $R_2$ is thiazolyl, or imidazolyl.

In another aspect, the invention provides compounds of formula 11-46, i.e., compounds of formula 11-43 where, $R_3$ is NR'R"; $R_{3a}$ is H; and $R_1$ is pyridyl or pyrimidyl; and $R_2$ is H.

In still yet another aspect, the invention provides compounds of formula 11-47, i.e., compounds of formula 11-43 where, $R_3$ is NR'R"; $R_{3a}$ is H; $R_1$ is pyridyl, or pyrimidyl; and $R_2$ is pyrimidyl, pyridyl, thiazolyl, or imidazolyl.

In another aspect, the invention provides compounds of formula 11-48, i.e., compounds of formula 11-43 where $R_1$ is H and $R_2$ is methyl, ethyl or propyl (n or iso). In another embodiment $R_2$ is methyl. In yet another embodiment $R_2$ is ethyl. In another embodiment $R_2$ is propyl (n or iso).

In another aspect, the invention provides compounds of formula 11-49, i.e., compounds of formula 11-43 where $R_2$ is H and $R_1$ is methyl, ethyl or propyl (n or iso). In another embodiment $R_1$ is methyl. In yet another embodiment $R_1$ is ethyl. In another embodiment $R_1$ is propyl (n or iso).

In still yet another aspect, the invention provides compounds of formula 11-50, i.e., compounds of formula 11-43 where, $R_3$ is halogen; $R_{3a}$ is H or halogen; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other. In still another embodiment $R_3$ and $R_{3a}$ are the same. When $R_3$ and $R_{3a}$ are the same, they may both be F.

In still yet another aspect, the invention provides compounds of formula 11-51, i.e., compounds of formula 11-43 where, $R_3$ is OH; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In yet still another aspect, the invention provides compounds of formula 11-52, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_3$ and $R_3$, combine to form oxo, =N—OH, or =N—O—$C_1$-$C_4$ alkyl; $R_1$ is H, pyridyl, pyrimidyl, $C_1$-$C_4$ alkyl (methyl, ethyl), or $C_3$-$C_6$ cycloalkyl; $R_2$ is H, $C_1$-$C_4$ alkyl (methyl, ethyl, isopropyl), pyrimidyl, pyridyl, thiazolyl, or imidazolyl; and $R_{1a}$ and $R_{2a}$ are both H.

In another aspect, the invention provides compounds of formula 11-53, i.e., compounds of formula 11-52 where, $R_3$ and $R_{3a}$ combine to form oxo; and $R_1$ is $C_3$-$C_6$ cycloalkyl, pyridyl or pyrimidyl.

In yet another aspect, the invention provides compounds of formula 11-54, i.e., compounds of formula 11-53 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 11-55, i.e., compounds of formula 11-52 where, $R_3$ and $R_{3a}$ combine to form oxo; and $R_1$ is H or $C_1$-$C_4$ alkyl (such as methyl, ethyl or isopropyl).

In another aspect, the invention provides compounds of formula 11-56, i.e., compounds of formula 11-55 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 11-57, i.e., compounds of formula 11-52 where, $R_1$ and $R_2$ are both H.

In still yet another aspect, the invention provides compounds of formula 11-58, i.e., compounds according to either formula 11-53 or 11-55 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other, In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 11-59, i.e., compounds of formula 11-52 where, $R_3$ and $R_{3a}$ combine to form =N—OH; and $R_1$ is $C_3$-$C_6$ cycloalkyl, pyridyl or pyrimidyl.

In yet another aspect, the invention provides compounds of formula 11-60, i.e., compounds of formula 11-59 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 11-61, i.e., compounds of formula 11-52 where, $R_3$ and $R_{3a}$ combine to form =N—OH; and $R_1$ is H or $C_1$-$C_4$ alkyl (such as methyl, ethyl or isopropyl).

In another aspect, the invention provides compounds of formula 11-62, i.e., compounds of formula 11-61 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 11-63, i.e., compounds according to either formula 11-59 or 11-61 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl, In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 11-64, i.e., compounds of formula 11-52 where, $R_3$ and $R_{3a}$ combine to form =N—O—$C_1$-$C_4$ alkyl; and $R_1$ is $C_3$-$C_6$ cycloalkyl, pyridyl or pyrimidyl.

In yet another aspect, the invention provides compounds of formula 11-65, i.e., compounds of formula 11-64 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 11-66, i.e., compounds of formula 11-52 where, $R_3$ and $R_{3a}$ combine to form =N—O—$C_1$-$C_4$ alkyl; and $R_1$ is H or $C_1$-$C_4$ alkyl (such as methyl, ethyl or isopropyl).

In another aspect, the invention provides compounds of formula 11-67, i.e., compounds of formula 11-66 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 11-68, i.e., compounds according to either formula 11-64 or 11-66 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In a further aspect, the invention provides compounds of formula 11-69, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_1$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_2$ is H, methyl, or ethyl; where R' and R" are independently H or $C_1$-$C_4$ alkyl. When $R_2$ is methyl or ethyl, $R_1$ and $R_2$ may be cis or trans relative to each other.

In still another aspect, the invention provides compounds of formula 11-70, i.e., compounds of formula 11-69 where, $R_1$ is pyridyl, pyrimidyl, thiazolyl, benzimidazolyl, or imidazolyl.

In yet another aspect, the invention provides compounds of formula 11-71, i.e., compounds of formula 11-69 where, $R_1$ is —$CO_2$-Me or —$CO_2$-Et.

In yet another aspect, the invention provides compounds of formula 11-72, i.e., compounds of formula 11-69 where, $R_1$ is methyl, ethyl, or propyl (either n or iso).

In yet another aspect, the invention provides compounds of formula 11-73, i.e., compounds of formula 11-69 where, $R_1$ is —$CH_2$—OC(O)NR'R", where R' and R" are independently H or $C_1$-$C_2$ alkyl. In one embodiment, $R_2$ is H. In another embodiment, $R_2$ is ethyl.

In a further aspect, the invention provides compounds of formula 11-74, i.e., compounds according to any one of formulas 10, 10-1, 10-2, 10-3, 10-4, 10-5, 10-6, 10-6a, 10-7, 10-8, 10-9, 10-10, 10-11, 10-11a, 10-11b, 10-12, 10-13, 10-14, or 10-15, wherein $R_1$ is —$C_1$-$C_4$ alkyl-OC(O)NR'R"; $R_2$ is H or —$C_1$-$C_4$ alkyl-OC(O)NR'R"; and $R_{1a}$, $R_2$, $R_3$, and $R_{3a}$ are H; where R' and R" are independently H or $C_1$-$C_3$ alkyl. In one embodiment, $R_1$ and $R_2$ are both —$CH_2$—OC(O)NR'R". In still another embodiment, R' and R" are both H, methyl or ethyl. In yet another embodiment, at least one of R' and R" is isopropyl.

In yet another aspect, the invention provides compounds of formula 11-75, i.e., compounds according to any one of formulas 10, up to and including 10-15, or any one of formulas 11, up to and including 11-74, wherein the $C_3$-$C_8$ cycloalkyl group is cyclopropyl.

In yet another aspect, the invention provides compounds of formula 11-76, i.e., compounds according to any one of formulas 10, up to and including 10-15, or any one of formulas 11, up to and including 11-74, wherein the $C_3$-$C_8$ cycloalkyl group is cyclobutyl.

In yet another aspect, the invention provides compounds of formula 11-77, i.e., compounds according to any one of formulas 10, up to and including 10-15, or any one of formulas 11, up to and including 11-74, wherein the $C_3$-$C_8$ cycloalkyl group is cyclopentyl.

In yet another aspect, the invention provides compounds of formula 11-78, i.e., compounds according to any one of formulas 10, up to and including 10-15, or any one of formulas 11, up to and including 11-74, wherein the $C_3$-$C_8$ cycloalkyl group is cyclohexyl.

In yet another aspect, the invention provides compounds of formula 11-79, i.e., compounds according to any one of formulas 10, up to and including 10-15, or any one of formulas 11, up to and including 11-74, wherein the $C_3$-$C_8$ cycloalkyl group is cycloheptyl.

In still yet another aspect, the invention provides compounds of formula 11-80, i.e., compounds according to any one of formulas 10, up to and including 10-15, or any one of formulas 11, up to and including 11-74, wherein the $C_3$-$C_8$ cycloalkyl group is cyclooctyl.

In another aspect, the invention provides compounds of formula 12, i.e., compounds of formula 4, wherein the A-ring is heteroaryl, which is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, heteroaryl, aryl, or —$SO_2$—NR'R", where each R' and R" is independently H or $C_1$-$C_6$ alkyl; and the B-ring is pyrazolyl, imidazolyl, pyrrolyl, triazolyl, pyrrolidinyl, pyrazolidinyl, imidazolidinyl, isoxazolyl, pyrimidyl or pyridyl each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, or phenyl.

In still another aspect, the invention provides compounds of formula 13, i.e., compounds of formula 12, of the formulas:

(formula 13)

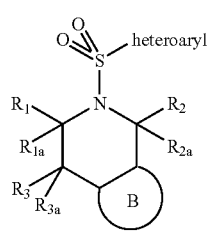

wherein the heteroaryl group is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still yet another aspect, the invention provides compounds of formula 13-1, i.e., compounds according to formula 13, wherein the B-ring is pyrazolyl, imidazolyl, pyrrolyl, triazolyl, pyrrolidinyl, pyrazolidinyl, imidazolidinyl, isoxazolyl, pyrimidyl or pyridyl, each of which is unsubstituted.

In still yet another aspect, the invention provides compounds of formula 13-2, i.e., compounds according to formula 13, wherein the B-ring has the formula:

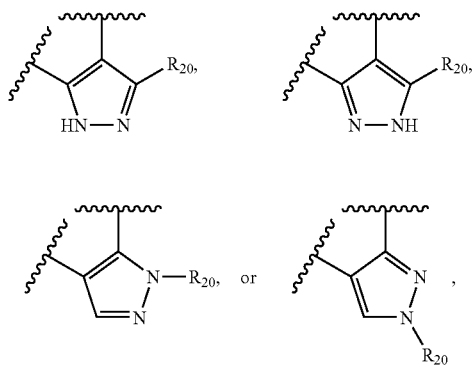

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, $C_1$-$C_6$ alkythio, halo, $CF_3$, or phenyl.

In still yet another aspect, the invention provides compounds of formula 13-3, i.e., compounds according to formula 13, wherein the B-ring has the formula:

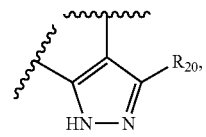

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still yet another aspect, the invention provides compounds of formula 13-4, i.e., compounds according to formula 13, wherein the B-ring has the formula:

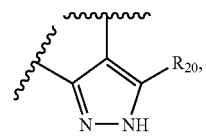

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still yet another aspect, the invention provides compounds of formula 13-5, i.e., compounds according to formula 13, wherein the B-ring has the formula:

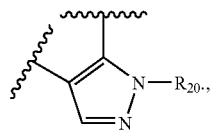

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still yet another aspect, the invention provides compounds of formula 13-6, i.e., compounds according to formula 13, wherein the B-ring has the formula:

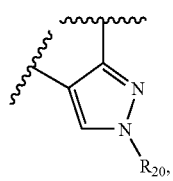

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 13-6a, i.e., compounds according to any one of formulas 13-3, 13-4, 13-5, or 13-6, where $R_{20}$ is H, or $C_1$-$C_6$ alkyl. In another embodiment, $R_{20}$ is phenyl. In still another embodiment, when the $R_{20}$ group is attached to a carbon, $R_{20}$ is $C_1$-$C_4$ alkoxy, $C_1$-$C_4$ alkythio, halo, $CF_3$, or phenyl. In yet another embodiment, $R_{20}$ is H.

In still yet another aspect, the invention provides compounds of formula 13-7, i.e., compounds according to formula 13, wherein the B-ring has the ormula:

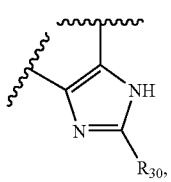 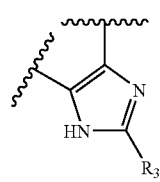 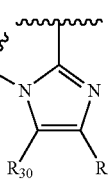 or

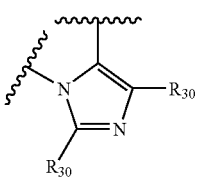

wherein $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still yet another aspect, the invention provides compounds of formula 13-8, i.e., compounds according to formula 13, wherein the B-ring has the formula:

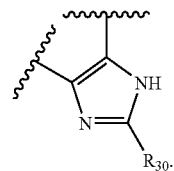

In still yet another aspect, the invention provides compounds of formula 13-9, i.e., compounds according to formula 13, wherein the B-ring has the formula:

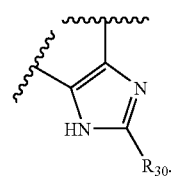

In still yet another aspect, the invention provides compounds of formula 13-10, i.e., compounds according to formula 13, wherein the B-ring has the formula:

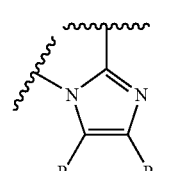

In still yet another aspect, the invention provides compounds of formula 13-11, i.e., compounds according to formula 13, wherein the B-ring has the formula:

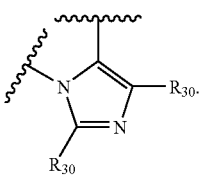

In still another aspect, the invention provides compounds of formula 13-11a, i.e., compounds according to any one of formulas 13-8, 13-9, or 13-10, where $R_{30}$ is H, or $C_1$-$C_6$ alkyl. In another embodiment, $R_{30}$ is phenyl. In still another embodiment, when the $R_{30}$ group is attached to a carbon, $R_{30}$ is $C_1$-$C_4$ alkoxy, $C_1$-$C_4$ alkythio, halo, $CF_3$, or phenyl. In yet another embodiment, $R_{30}$ is H.

In another aspect, the invention provides compounds of formula 13-11b, i.e., compounds according to any one of formulas 13-8, 13-9, or 13-10, where $R_{30}$ is amino, $C_1$-$C_4$ alkylamino, $C_1$-$C_4$ dialkylamino.

In still yet another aspect, the invention provides compounds of formula 13-12, i.e., compounds according to formula 13, wherein the B-ring has the formula:

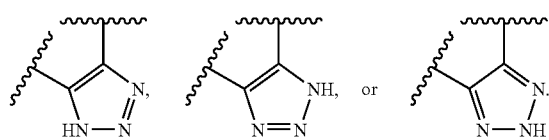

In still yet another aspect, the invention provides compounds of formula 13-13, i.e., compounds according to formula 13, wherein the B-ring has the formula:

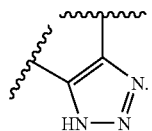

In still yet another aspect, the invention provides compounds of formula 13-14, i.e., compounds according to formula 13, wherein the B-ring has the formula:

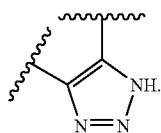

In still yet another aspect, the invention provides compounds of formula 13-15, i.e., compounds according to formula 13, wherein the B-ring has the formula:

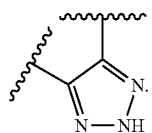

In yet still another aspect, the invention provides compounds of formula 14, i.e., compounds according to any one of formulas 13, 13-1, 13-2, 13-3, 13-4, 13-5, 13-6, 13-7, 13-8, 13-9, 13-10, 13-11, 13-12, 13-13, 13-14, or 13-15, wherein $R_1$ is $C_1$-$C_6$ alkyl, $C_3$-$C_6$cycloalkyl, $C_3$-$C_6$cycloalkylalkyl, phenyl, biphenyl, phenyl$C_1$-$C_6$ alkyl (such as benzyl or phenethyl), phenyloxy$C_1$-$C_6$ alkyl, or naphthyloxy$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 14a, i.e., compounds of formula 14, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 14b, i.e., compounds of formula 14, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 14c, i.e., compounds of formula 14, wherein $R_2$ is hydrogen, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", —$C_0$-$C_6$ alkyl NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 14d, i.e., compounds of formula 14, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet still another aspect, the invention provides compounds of formula 14-1, i.e., compounds according to any one of formulas 13, 13-1, 13-2, 13-3, 13-4, 13-5, 13-6, 13-7, 13-8, 13-9, 13-10, 13-11, 13-12, 13-13, 13-14, or 13-15 wherein $R_1$ is pyridyl, thiazolyl, imidazolyl, benzofuranyl, benzothienyl, benzimidazolyl, quinolinyl, isoquinolinyl, quinoxalinyl, quinazolinyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —$C_1$-$C_6$ alkyl-OC(O)NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 14-1a, i.e., compounds of formula 14-1, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl; $C_3$-$C_6$ cycloalkyl, $C_3$-$C_6$ cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 14-1b, i.e., compounds of formula 14-1, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 14-1c, i.e., compounds of formula 14-1, wherein $R_2$ is hydrogen, —$CO_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", —$C_0$-$C_6$ alkyl-NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 14-1d, i.e., compounds of formula 14-1, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet still another aspect, the invention provides compounds of formula 14-2, i.e., compounds according to any one of formulas 14-1, 14-1a, 14-1b, 14-1c, or 14-1d, wherein $R_1$ is pyridyl, thiazolyl, imidazolyl, benzofuranyl, benzothienyl, benzimidazolyl, quinolinyl, isoquinolinyl, quinoxalinyl, or quinazolinyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, -$CO_2$R', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and $R_{1a}$ and $R_{2a}$ are both H.

In yet still another aspect, the invention provides compounds of formula 14-3, i.e., compounds according to any one of formulas 14-1, 14-1a, 14-1b, 14-1c, or 14-1d, wherein $R_1$ is pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, or quinazolinyloxy $C_1$-$C_6$ alkyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet still another aspect, the invention provides compounds of formula 14-4, i.e., compounds according to formula 14-1, 14-1a, 14-1b, 14-1c, or 14-1d, wherein $R_1$ is —$C_0$-$C_6$ alkyl-OC(O)NR'R", —$C_0$-$C_6$ alkyl-NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, —$CO_2$R', phenyl, pyridazinyl, pyrazinyl, pyrimidyl, thiazolyl, pyridyl, N-methyl pyrazolyl, N-benzyl pyrazolyl, oxadiazolyl, oxazolyl, or imidazolyl; and $R_{1a}$ and $R_{2a}$ are both H.

In yet still another aspect, the invention provides compounds of formula 14-5, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ is —$CO_2$R', —CONR'R", $C_1$-$C_4$ haloalkyl, or $C_1$-$C_4$ hydroxyalkyl; and $R_{1a}$ and $R_{2a}$ are both H. In one embodiment, $R_1$ is as defined above and $R_2$ is H. In another embodiment, $R_1$ is as defined above and $R_2$ is methyl, ethyl, or cyclopropyl. In still another embodiment, $R_1$ is as defined above and $R_2$ is $C_1$-$C_4$ hydroxyalkyl. In a further embodiment, $R_1$ and $R_2$ are independently —$CO_2$—$C_1$-$C_4$ alkyl. In another embodiment, $R_1$ and $R_2$ are independently $C_1$-$C_2$ hydroxyalkyl. In yet another embodiment, $R_1$ is $C_1$-$C_2$ hydroxyalkyl and $R_2$ is methyl or ethyl.

In a further aspect, the invention provides compounds of formula 14-6, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ is H or $C_1$-$C_6$ alkoxy, $R_2$ is H or $C_1$-$C_6$ alkoxy, and $R_{1a}$ and $R_{2a}$ are both H. In one embodiment, $R_1$ is $C_1$-$C_6$ alkoxy and $R_2$ is H or $C_1$-$C_6$ alkoxy. In another embodiment $R_1$ and $R_2$ are independently $C_1$-$C_6$ alkoxy, In yet another embodiment $R_1$ and $R_2$ are both H.

In another aspect, the invention provides compounds of formula 14-7, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_2$ are both $C_2$-$C_4$ alkenyl optionally substituted with one or more halogens (such as F or Cl), and $R_{1a}$ and $R_{2a}$ are both H. In one embodiment, $R_1$ and $R_2$ are the same. In a further embodiment, $R_1$ and $R_2$ are both $C_2$ alkenyl substituted with two halogens (such as F). $R_1$ and $R_2$ may be cis or trans relative to each other.

In another aspect, the invention provides compounds of formula 14-8, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are the same and are —$CH_2F$, —$CH_2CF_3$, —$CH_2CHF_2$, $CF_3$, or —$CF_2CH_3$.

In another aspect, the invention provides compounds of formula 14-9, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_2$ are both benzyl or phenethyl, and $R_{1a}$ and $R_{2a}$ are both H. $R_1$ and $R_2$ may be cis or trans relative to each other. In one embodiment, $R_1$ and $R_2$ are both benzyl.

In another aspect, the invention provides compounds of formula 14-10, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_2$ are both H or $C_1$-$C_4$ alkyl and $R_{1a}$ and $R_{2a}$ are both H. $R_1$ and $R_2$ may be cis or trans relative to each other. In one embodiment, $R_1$ and $R_2$ are both methyl. In another embodiment, both $R_1$ and $R_2$ are both isopropyl. In still another embodiment, one or $R_1$ and $R_2$ is methyl while the other is isopropyl. In yet another embodiment, both of $R_1$ and $R_2$ are ethyl.

In another aspect, the invention provides compounds of formula 14-11, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ is H, $C_1$-$C_4$ alkyl, benzyl, phenethyl, or phenyl, where the phenyl portions of $R_1$ are optionally substituted with 1, 2, or 3 groups that are independently halogen, $C_1$-$C_4$ alkyl, or $C_1$-$C_4$ alkoxy and $R_2$ is H or $C_1$-$C_4$ alkyl, and $R_{1a}$ and $R_{2a}$ are both H. $R_1$ and $R_2$ may be cis or trans relative to each other.

In one aspect, the invention provides compounds of formula 14-12, i.e., compounds of formula 14-11 where, $R_2$ is H and $R_1$ is methyl, ethyl or propyl (n or iso), or $R_1$ is H and $R_2$ is methyl, ethyl or propyl (n or iso). In one embodiment, only one of $R_1$ and $R_2$ is isopropyl. In another embodiment, only one of $R_1$ and $R_2$ is ethyl.

In still another aspect, the invention provides compounds of formula 14-13, i.e., compounds of formula 14-11 where, $R_2$ is H and $R_1$ is phenyl substituted with one or two halogens (such as F or Cl), or $R_1$ is H and $R_2$ is phenyl substituted with one or two halogens (such as F or Cl)

In one aspect, the invention provides compounds of formula 14-14, i.e., compounds of formula 14-11 where, $R_2$ is H and $R_1$ is benzyl substituted with one or two groups that are independently halogen (such as F or Cl), methyl, ethyl, methoxy, or ethoxy.

In yet another aspect, the invention provides compounds of formula 14-15, i.e., compounds of formula 14-11 where, $R_2$ is methyl or ethyl, and $R_1$ is methyl, ethyl or propyl (n or iso). In one embodiment, $R_1$ and $R_2$ are both ethyl.

In still yet another aspect, the invention provides compounds of formula 14-16, i.e., compounds of formula 14-11 where, $R_2$ is methyl or ethyl, and $R_1$ is phenyl substituted with one or two halogens (such as F or Cl).

In yet another aspect, the invention provides compounds of formula 14-17, i.e., compounds of formula 14-11 where, $R_2$ is methyl or ethyl, and $R_1$ is benzyl substituted with one or two groups that are independently halogen (such as F or Cl), methyl, ethyl, methoxy, or ethoxy.

In another aspect, the invention provides compounds of formula 14-18, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_2$ are independently H or —$CO_2$—$C_1$-$C_4$ alkyl, and $R_{1a}$ and $R_{2a}$ are both H. $R_1$ and $R_2$ may be cis or trans relative to each other. In one embodiment, $R_1$ is —$CO_2$—$C_1$-$C_2$ alkyl and $R_2$ is H. In another embodiment, $R_1$ is —$CO_2$-Et and $R_2$ is H. In still another embodiment, $R_1$ is H and $R_2$ is —$CO_2$—$C_1$-$C_2$ alkyl. In yet another embodiment, $R_1$ and $R_2$ are both —$CO_2$-Et.

In another aspect, the invention provides compounds of formula 14-19, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ and $R_3$ form a double bond and $R_{1a}$ and $R_{3a}$ are both H. In one embodiment, $R_2$ is H. In another embodiment, $R_2$ is —$CO_2$—$C_1$-$C_4$ alkyl. In yet another embodiment, $R_2$ is —$CO_2$-Et. In still another embodiment, $R_2$ is methyl or ethyl. In still yet another embodiment, $R_2$ is thiazolyl, pyridyl or pyrimidyl.

In still another aspect, the invention provides compounds of formula 14-20, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_1$ is pyridyl, pyrimidyl, $C_3$-$C_6$ cycloalkyl, or thienyl, $R_2$ is H, $C_0$-$C_4$ alkyl, or $C_3$-$C_6$ cycloalkyl, and $R_{1a}$ and $R_{2a}$ are both H. $R_1$ and $R_2$ may be cis or trans relative to each other.

In yet still another aspect, the invention provides compounds of formula 14-21, i.e., compounds of formula 14-20 where, $R_1$ is pyridyl and $R_2$ is H.

In yet another aspect, the invention provides compounds of formula 14-22, i.e., compounds of formula 14-20 where, $R_1$ is pyridyl and $R_2$ is methyl or ethyl.

In a further aspect, the invention provides compounds of formula 14-23, i.e., compounds of formula 14-20 where, $R_1$ is pyridyl and $R_2$ is $C_3$, $C_5$, or $C_6$ cycloalkyl. In another embodiment, $R_2$ is $C_3$ cycloalkyl.

In still another aspect, the invention provides compounds of formula 14-24, i.e., compounds of formula 14-20 where, $R_1$ is pyrimidyl and $R_2$ is H.

In another aspect, the invention provides compounds of formula 14-25, i.e., compounds of formula 14-20 where, $R_1$ is pyrimidyl and $R_2$ is methyl or ethyl.

In yet another aspect, the invention provides compounds of formula 14-26, i.e., compounds of formula 14-20 where, $R_1$ is pyrimidyl and $R_2$ is $C_3$, $C_5$, or $C_6$ cycloalkyl.

In still another aspect, the invention provides compounds of formula 14-27, i.e., compounds of formula 14-20 where, $R_1$ is $C_3$, $C_5$, or $C_6$ cycloalkyl and $R_2$ is H.

In yet still another aspect, the invention provides compounds of formula 14-28, i.e., compounds of formula 14-20 where, $R_1$ is $C_3$, $C_5$, or $C_6$ cycloalkyl and $R_2$ is methyl or ethyl.

In yet another aspect, the invention provides compounds of formula 14-29, i.e., compounds of formula 14-20 where, $R_1$ is $C_3$, $C_5$, or $C_6$ cycloalkyl and $R_2$ is $C_3$, $C_5$, or $C_6$ cycloalkyl. In one embodiment one of $R_1$ and $R_2$ is $C_3$ cycloalkyl. In another embodiment, both of $R_1$ and $R_2$ are $C_3$ cycloalkyl.

In still another aspect, the invention provides compounds of formula 14-30, i.e., compounds of formula 14-20 where, $R_1$ is thienyl and $R_2$ is H.

In yet another aspect, the invention provides compounds of formula 14-31, i.e., compounds of formula 14-20 where, $R_1$ is thienyl and $R_2$ is methyl or ethyl.

In yet another aspect, the invention provides compounds of formula 14-32, i.e., compounds of formula 14-20 where, $R_1$ is thienyl and $R_2$ is $C_3$, $C_5$, or $C_6$ cycloalkyl. In one embodiment, $R_2$ is $C_3$ cycloalkyl.

In a further aspect, the invention provides compounds of formula 14-33, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_2$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_1$ is H, methyl, or ethyl; where R' and R" are independently H or $C_1$-$C_4$ alkyl. When $R_1$ is methyl or ethyl, $R_1$ and $R_2$ may be cis or trans relative to each other.

In still another aspect, the invention provides compounds of formula 14-34, i.e., compounds of formula 14-33 where, $R_2$ is pyridyl, pyrimidyl, thiazolyl, benzimidazolyl, or imidazolyl. In one embodiment, $R_2$ is thiazolyl and $R_1$ is H. In another embodiment, $R_2$ is thiazolyl and $R_1$ is methyl or ethyl. In still another embodiment, $R_2$ is pyridyl and $R_1$ is H. In another embodiment, $R_2$ is pyridyl and $R_1$ is methyl or ethyl. In yet another embodiment, $R_2$ is pyrimidyl and $R_1$ is H. In another embodiment, $R_2$ is pyrimidyl and $R_1$ is methyl or ethyl.

In yet another aspect, the invention provides compounds of formula 14-35, i.e., compounds of formula 14-33 where, $R_2$ is —$CO_2$-Me or —$CO_2$-Et.

In yet another aspect, the invention provides compounds of formula 14-36, i.e., compounds of formula 14-33 where, $R_2$ is methyl, ethyl, or propyl (either n or iso).

In yet another aspect, the invention provides compounds of formula 14-37, i.e., compounds of formula 14-33 where, $R_2$ is —$CH_2$—OC(O)NR'R", where R' and R" are independently H or $C_1$-$C_2$ alkyl. In one embodiment, $R_1$ is H. In another embodiment, $R_1$ is ethyl.

In yet still another aspect, the invention provides compounds of formula 14-38, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_2$ and $R_{2a}$ combine to form oxo.

In still another aspect, the invention provides compounds of formula 14-39, i.e., compounds of formula 14-38 where, $R_1$ is H, $C_1$-$C_4$ alkyl, $C_3$-$C_6$ cycloalkyl, or —$C_1$-$C_4$ alkyl-OC(O)NR'R", where R' and R" are independently H or $C_1$-$C_4$ alkyl, and $R_{1a}$ is H.

In still another aspect, the invention provides compounds of formula 14-40, i.e., compounds of formula 14-38 where, $R_1$ is H, methyl or ethyl. In one embodiment, $R_1$ is H. In another embodiment, $R_1$ is methyl or ethyl.

In yet another aspect, the invention provides compounds of formula 14-41, i.e., compounds of formula 14-38 where, $R_1$ is $C_3$, $C_5$, or $C_6$ cycloalkyl. In one embodiment, $R_1$ is $C_3$ cycloalkyl. In another embodiment, $R_1$ is $C_5$ or $C_6$ cycloalky.

In still yet another aspect, the invention provides compounds of formula 14-42, i.e., compounds of formula 14-38 where, $R_1$ is —$C_1$-$C_2$ alkyl-OC(O)NR'R", where R' and R" are independently H, methyl, or ethyl.

In yet still another aspect, the invention provides compounds of formula 14-43, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_3$ is NR'R", OH, halogen, $R_{3a}$ is H or halogen; or $R_3$ and $R_{3a}$ combine to form oxo, =N—OH, or =N—O—$C_1$-$C_4$ alkyl. $R_1$ is H, pyridyl, pyrimidyl, $C_1$-$C_4$ alkyl; $R_2$ is H, $C_1$-$C_4$ alkyl, pyrimidyl, pyridyl, thiazolyl, or imidazolyl; and $R_{1a}$ and $R_{2a}$ are both H.

In still yet another aspect, the invention provides compounds of formula 14-44, i.e., compounds of formula 14.43 where, $R_3$ is NR'R"; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In still yet another aspect, the invention provides compounds of formula 14-45, i.e., compounds of formula 14-43 where, $R_3$ is NR'R"; $R_{3a}$ is H; and $R_1$ is H, methyl ethyl or propyl (n or iso); and $R_2$ is H, pyrimidyl, pyridyl, thiazolyl, or imidazolyl. In one embodiment, $R_1$ is H and $R_2$ is pyrimidyl or pyridyl. In another embodiment, $R_1$ is H and $R_2$ is thiazolyl, or imidazolyl. In one embodiment, $R_1$ is methyl, ethyl or propyl (n or iso) and $R_2$ is pyrimidyl or pyridyl. In another embodiment, $R_1$ is methyl, ethyl or propyl (n or iso) and $R_2$ is thiazolyl, or imidazolyl.

In another aspect, the invention provides compounds of formula 14-46, i.e., compounds of formula 14-43 where, $R_3$ is NR'R"; $R_{3a}$ is H; and $R_1$ is pyridyl or pyrimidyl; and $R_2$ is H.

In still yet another aspect, the invention provides compounds of formula 14-47, i.e., compounds of formula 14-43 where, $R_3$ is NR'R"; $R_{3a}$ is H; $R_1$ is pyridyl, or pyrimidyl; and $R_2$ is pyrimidyl, pyridyl, thiazolyl, or imidazolyl.

In another aspect, the invention provides compounds of formula 14-48, i.e., compounds of formula 14-43 where $R_1$ is H and $R_2$ is methyl, ethyl or propyl (n or iso). In another embodiment $R_2$ is methyl. In yet another embodiment $R_2$ is ethyl. In another embodiment $R_2$ is propyl (n or iso).

In another aspect, the invention provides compounds of formula 14-49, i.e., compounds of formula 14-43 where $R_2$ is H and $R_1$ is methyl, ethyl or propyl (n or iso). In another embodiment $R_1$ is methyl. In yet another embodiment $R_1$ is ethyl. In another embodiment $R_1$ is propyl (n or iso).

In still yet another aspect, the invention provides compounds of formula 14-50, i.e., compounds of formula 14-43 where, $R_3$ is halogen; $R_{3a}$ is H or halogen; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other. In still another embodiment $R_3$ and $R_{3a}$ are the same. When $R_3$ and $R_{3a}$ are the same, they may both be F.

In still yet another aspect, the invention provides compounds of formula 14-51, i.e., compounds of formula 14-43 where, $R_3$ is OH; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In yet still another aspect, the invention provides compounds of formula 14-52, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein $R_3$ and $R_{3a}$ combine to form oxo, =N—OH, or =N—O—$C_1$-$C_4$ alkyl; $R_1$ is H, pyridyl, pyrimidyl, $C_1$-$C_4$ alkyl (methyl, ethyl), or $C_3$-$C_6$ cycloalkyl; $R_2$ is H, $C_1$-$C_4$ alkyl (methyl, ethyl, isopropyl), pyrimidyl, pyridyl, thiazolyl, or imidazolyl; and $R_{1a}$ and $R_{2a}$ are both H.

In another aspect, the invention provides compounds of formula 14-53, i.e., compounds of formula 14-52 where, $R_3$ and $R_{3a}$ combine to form oxo; and $R_1$ is $C_3$-$C_6$ cycloalkyl, pyridyl or pyrimidyl.

In yet another aspect, the invention provides compounds of formula 14-54, i.e., compounds of formula 14-53 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 14-55, i.e., compounds of formula 14-52 where, $R_3$ and $R_{3a}$ combine to form oxo; and $R_1$ is H or $C_1$-$C_4$ alkyl (such as methyl, ethyl or isopropyl).

In another aspect, the invention provides compounds of formula 14-56, i.e., compounds of formula 14-55 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 14-57, i.e., compounds of formula 14-52 where, $R_1$ and $R_2$ are both H.

In still yet another aspect, the invention provides compounds of formula 14-58, i.e., compounds according to either formula 14-53 or 14-55 where, $R_2$ is pyrimidyl, pyridyl, thiazolyl, or imidazolyl, In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 14-59, i.e., compounds of formula 14-52 where, $R_3$ and $R_{3a}$ combine to form =N—OH; and $R_1$ is $C_3$-$C_6$ cycloalkyl, pyridyl or pyrimidyl.

In yet another aspect, the invention provides compounds of formula 14-60, i.e., compounds of formula 14-59 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H, In a further embodiment, $R_1$ is cyclopropyl and $R_2$ is H. In a further embodiment, $R_1$ is cyclopropyl and $R_2$ is H.

In still yet another aspect, the invention provides compounds of formula 14-61, i.e., compounds of formula 14-52 where, $R_3$ and $R_{3a}$ combine to form =N—OH; and $R_1$ is H or $C_1$-$C_4$ alkyl (such as methyl, ethyl or isopropyl).

In another aspect, the invention provides compounds of formula 14-62, i.e., compounds of formula 14-61 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 14-63, i.e., compounds according to either formula 14-59 or 14-61 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 14-64, i.e., compounds of formula 14-52 where, $R_3$ and $R_{3a}$ combine to form =N—O—$C_1$-$C_4$ alkyl; and $R_1$ is $C_3$-$C_6$ cycloalkyl, pyridyl or pyrimidyl.

In yet another aspect, the invention provides compounds of formula 14-65, i.e., compounds of formula 14-64 where, $R_2$ is H, $C_0$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 14-66, i.e., compounds of formula 14-52 where, $R_3$ and $R_{3a}$ combine to form =N—O—$C_1$-$C_4$ alkyl; and $R_1$ is H or $C_1$-$C_4$ alkyl (such as methyl, ethyl or isopropyl).

In another aspect, the invention provides compounds of formula 14-67, i.e., compounds of formula 14-66 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 14-68, i.e., compounds according to either formula 14-64 or 14-66 where, R₂ is pyrimidyl, pyridyl, thiazolyl, or imidazolyl. In one embodiment, R₂ is pyrimidyl or pyridyl. In another embodiment, R₂ is thiazolyl, or imidazolyl. In still another embodiment, when R₁ is not H, then R₁ and R₂ are cis relative to each other. In still another embodiment, when R₁ is not H, then R₁ and R₂ are trans relative to each other. In still another embodiment, R₁ is pyrimidyl and R₂ is pyrimidyl or pyridyl. In yet still another embodiment, R₁ is pyridyl and R₂ is pyrimidyl or pyridyl. In a further embodiment, R₁ is cyclopropyl and R₂ is pyrimidyl or pyridyl. In a further embodiment, R₁ is cyclopropyl and R₂ is pyrimidyl or pyridyl.

In a further aspect, the invention provides compounds of formula 14-69, i.e., compounds according to any one of formulas 13, 13-1, 13-2, 13-2, 13-4, 13-5, 13-6, 13-6a, 13-7, 13-8, 13-9, 13-10, 13-11, 13-11a, 13-11b, 13-12, 13-13, 13-14, or 13-15 wherein R₁ is pyridyl, pyrimidyl, —CO₂—C₁-C₄ alkyl, C₁-C₄ alkyl, —C₁-C₄ alkyl-OC(O)NR'R", benzimidazolyl, thiazolyl, or imidazolyl, and R₂ is H, methyl, or ethyl; where R' and R" are independently H or C₁-C₄ alkyl. When R₂ is methyl or ethyl, R₁ and R₂ may be cis or trans relative to each other.

In still another aspect, the invention provides compounds of formula 14-70, i.e., compounds of formula 14-69 where, R₁ is pyridyl, pyrimidyl, thiazolyl, benzimidazolyl, or imidazolyl.

In yet another aspect, the invention provides compounds of formula 14-71, i.e., compounds of formula 14-69 where, R₁ is —CO₂-Me or —CO₂-Et.

In yet another aspect, the invention provides compounds of formula 14-72, i.e., compounds of formula 14-69 where, R₁ is methyl, ethyl, or propyl (either n or iso).

In yet another aspect, the invention provides compounds of formula 14-73, i.e., compounds of formula 14-69 where, R₁ is —CH₂—OC(O)NR'R", where R' and R" are independently H or C₁-C₂ alkyl. In one embodiment, R₂ is H. In another embodiment, R₂ is ethyl.

In a further aspect, the invention provides compounds of formula 14-74, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein R₁ is —C₁-C₄ alkyl-OC(O)NR'R"; R₂ is H or —C₁-C₄ alkyl-OC(O)NR'R"; and R₁ₐ, R₂, R₃, and R₃, are H; where R' and R" are independently H or C₁-C₃ alkyl. In one embodiment, R₁ and R₂ are both —CH₂—OC(O)NR'R". In still another embodiment, R' and R" are both H, methyl or ethyl. In yet another embodiment, at least one of R' and R" is isopropyl.

In yet still another aspect, the invention provides compounds of formula 14-75, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein the heteroaryl group is pyridyl optionally substituted with 1 or 2 groups that are independently halogen, C₁-C₄ alkyl, C₁-C₄ alkoxy, CF₃, OCF₃, OH, amino, or mono or di(C₁-C₄ alkyl)amino.

In yet still another aspect, the invention provides compounds of formula 14-76, i.e., compounds 14-75, wherein the pyridyl is substituted with one group that is halogen, C₁-C₄ alkyl, C₁-C₄ alkoxy, CF₃, OCF₃, OH, amino, or mono or di(C₁-C₄ alkyl)amino.

In yet still another aspect, the invention provides compounds of formula 14-77, i.e., compounds of formula 14-76, wherein the pyridyl is substituted at the 4-position.

In yet still another aspect, the invention provides compounds of formula 14-78, i.e., compounds of formula 14-77, wherein the pyridyl is substituted with one group that is halogen (preferably chloro).

In yet still another aspect, the invention provides compounds of formula 14-79, i.e., compounds of formula 14-78, wherein the heteroaryl group has the following structure:

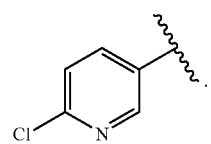

In yet still another aspect, the invention provides compounds of formula 14-80, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein the heteroaryl group is an unsubstituted pyridyl. In one embodiment, the pyridyl is a pyrid-2-yl. In another embodiment, the pyridyl is a pyrid-3-yl. In still another embodiment, the pyridyl is a pyrid-4-yl.

In yet still another aspect, the invention provides compounds of formula 14-81, i.e., compounds according to any one of formulas 13, 13-1, 13-2, 13-3, 13-4, 13-5, 13-6, 13-6a, 13-7, 13-8, 13-9, 13-10, 13-11, 13-11a, 13-11b, 13-12, 13-13, 13-14, or 13-15 wherein the heteroaryl group is thienyl optionally substituted with 1 or 2 groups that are independently halogen, C₁-C₄ alkyl, C₁-C₄ alkoxy, CF₃, OCF₃, OH, amino, or mono or di(C₁-C₄ alkyl)amino.

In yet still another aspect, the invention provides compounds of formula 14-82, i.e., compounds of formula 14-81 where the thienyl group is substituted with one group that is halogen, C₁-C₄ alkyl, C₁-C₄ alkoxy, CF₃, OCF₃, OH, amino, or mono or di(C₁-C₄ alkyl)amino.

In yet still another aspect, the invention provides compounds of formula 14-83, i.e., compounds of formula 14-82, wherein the thienyl group is substituted with one halogen (preferably Cl).

In yet still another aspect, the invention provides compounds of formula 14-84, i.e., compounds of formula 14-83, wherein the thienyl group has the formula:

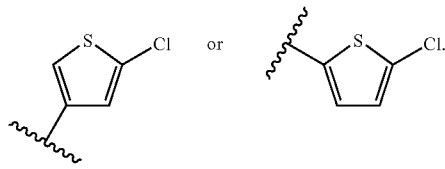

In yet still another aspect, the invention provides compounds of formula 14-85, i.e., compounds of formula 14-81, wherein the thienyl group is unsubstituted.

In yet still another aspect, the invention provides compounds of formula 14-86, i.e., compounds of formula 14-85, wherein the thienyl group has the formula:

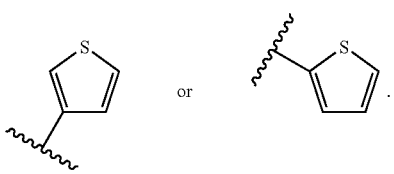 or 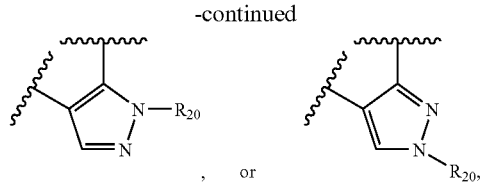

In another aspect, the invention provides compounds of formula 15, i.e., compounds of formula 4, wherein the A-ring is heterocycloalkyl, which is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, heteroaryl, aryl, or —$SO_2$—NR'R", where each R' and R" is independently H or $C_1$-$C_6$ alkyl; and the B-ring is pyrazolyl, imidazolyl, pyrrolyl, triazolyl, pyrrolidinyl, pyrazolidinyl, imidazolidinyl, isoxazolyl, pyrimidyl or pyridyl, each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, or phenyl.

In another aspect, the invention provides compounds of formula 16, i.e., compounds of either formula 4 or formula 15, wherein

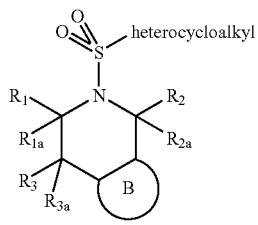

(formula 16)

wherein the heterocycloalkyl group is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In another aspect, the invention provides compounds of formula 16-1, i.e., compounds of formula 16, wherein the B-ring is pyrazolyl, imidazolyl, pyrrolyl, triazolyl, pyrrolidinyl, pyrazolidinyl, imidazolidinyl, isoxazolyl, pyrimidyl or pyridyl, each of which is unsubstituted.

In another aspect, the invention provides compounds of formula 16-2, i.e., compounds of formula 16, wherein the B-ring has the formula:

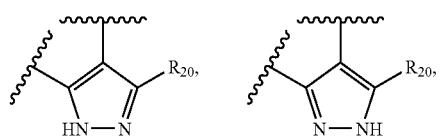

-continued wherein $R_{20}$ is H, $C_1$-$C_6$ alkyl, $C_1$-$C_6$ alkoxy, amino, $C_1$-$C_6$ alkylamino, $C_1$-$C_6$ dialkylamino, $C_1$-$C_6$ alkythio, halo, $CF_3$, or phenyl.

In another aspect, the invention provides compounds of formula 16-3, i.e., compounds of formula 16, wherein the B-ring has the formula:

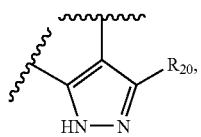

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In another aspect, the invention provides compounds of formula 16-4, i.e., compounds of formula 16, wherein the B-ring has the formula:

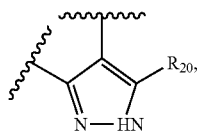

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In another aspect, the invention provides compounds of formula 16-5, i.e., compounds of formula 16, wherein the B-ring has the formula:

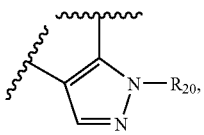

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In another aspect, the invention provides compounds of formula 16-6, i.e., compounds of formula 16, wherein the B-ring has the formula:

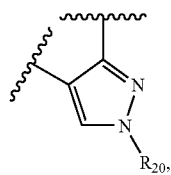

wherein R$_{20}$ is H, C$_1$-C$_4$ alkyl, C$_1$-C$_4$ alkoxy, amino, C$_1$-C$_4$ alkylamino, C$_1$-C$_4$ dialkylamino, C$_1$-C$_4$ alkythio, halo, CF$_3$, or phenyl.

In still another aspect, the invention provides compounds of formula 16-6a, i.e., compounds according to any one of formulas 16-3, 16-4, 16-5, or 16-6, where R$_{20}$ is H, or C$_1$-C$_6$ alkyl. In another embodiment, R$_{20}$ is phenyl. In still another embodiment, when the R$_{20}$ group is attached to a carbon, R$_{20}$ is C$_1$-C$_4$ alkoxy, C$_1$-C$_4$ alkythio, halo, CF$_3$, or phenyl. In yet another embodiment, R$_{20}$ is H.

In another aspect, the invention provides compounds of formula 16-7, i.e., compounds of formula 16, wherein the B-ring has the formula:

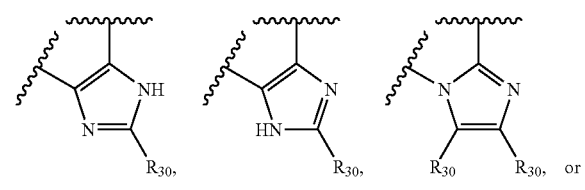

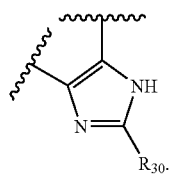

wherein R$_{30}$ is H, C$_1$-C$_4$ alkyl, C$_1$-C$_4$ alkoxy, amino, C$_1$-C$_4$ alkylamino, C$_1$-C$_4$ dialkylamino, C$_1$-C$_4$ alkythio, halo, CF$_3$, or phenyl.

In another aspect, the invention provides compounds of formula 16-8, i.e., compounds of formula 16, wherein the B-ring has the formula:

In another aspect, the invention provides compounds of formula 16-9, i.e., compounds of formula 16, wherein the B-ring has the formula:

In another aspect, the invention provides compounds of formula 16-10, i.e., compounds of formula 16, wherein the B-ring has the formula:

In another aspect, the invention provides compounds of formula 16-11, i.e., compounds of formula 16, wherein the B-ring has the formula:

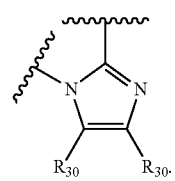

In still another aspect, the invention provides compounds of formula 16-11a, i.e., compounds according to any one of formulas 16-8, 16-10, or 16-10, where R$_{30}$ is H, or C$_1$-C$_6$ alkyl. In another embodiment, R$_{30}$ is phenyl. In still another embodiment, when the R$_{30}$ group is attached to a carbon, R$_{30}$ is C$_1$-C$_4$ alkoxy, C$_1$-C$_4$ alkythio, halo, CF$_3$, or phenyl. In yet another embodiment, R$_{30}$ is H.

In another aspect, the invention provides compounds of formula 16-11b, i.e., compounds according to any one of formulas 16-8, 16-9, or 16-10, where R$_{30}$ is amino, C$_1$-C$_4$ alkylamino, C$_1$-C$_4$ dialkylamino.

In another aspect, the invention provides compounds of formula 16-12, i.e., compounds of formula 16, wherein the B-ring has the formula:

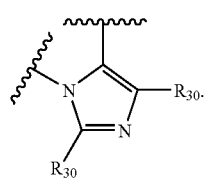

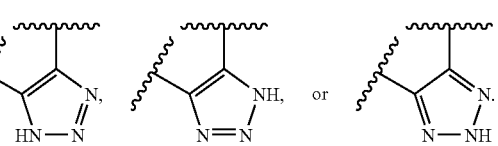

In another aspect, the invention provides compounds of formula 16-13, i.e., compounds of formula 16, wherein the B-ring has the formula:

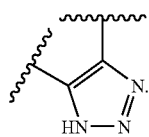

In another aspect, the invention provides compounds of formula 16-14, i.e., compounds of formula 16, wherein the B-ring has the formula:

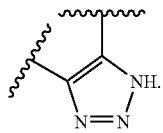

In another aspect, the invention provides compounds of formula 16-15, i.e., compounds of formula 16, wherein the B-ring has the formula:

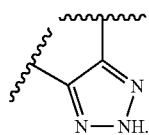

In another aspect, the invention provides compounds of formula 17, i.e., compounds of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is $C_1$-$C_6$ alkyl, $C_3$-$C_6$cycloalkyl, $C_3$-$C_6$cycloalkylalkyl, phenyl, biphenyl, phenyl$C_1$-$C_6$ alkyl (such as benzyl or phenethyl), phenyloxy$C_1$-$C_6$ alkyl, or naphthyloxy$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 17a, i.e., compounds of formula 17, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 17b, i.e., compounds of formula 17, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 17c, i.e., compounds of formula 17, wherein $R_2$ is hydrogen, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", —$C_0$-$C_6$ alkyl-NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 17d, i.e., compounds of formula 17, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In another aspect, the invention provides compounds of formula 17-1, i.e., compounds of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is pyridyl, thiazolyl, imidazolyl, benzofuranyl, benzothienyl, benzimidazolyl, quinolinyl, isoquinolinyl, quinoxalinyl, quinazolinyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —$C_1$-$C_6$ alkyl-OC(O)NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 17-1a, i.e., compounds of formula 17-1, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)

OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 17-1b, i.e., compounds of formula 17-1, wherein $R_2$ is hydrogen, pyridyl, thiazolyl, pyrimidyl, pyrazolyl, pyridyloxy $C_1$-$C_6$ alkyl, pyrimidyloxy $C_1$-$C_6$ alkyl, thienyloxy $C_1$-$C_6$ alkyl, pyrrolyloxy $C_1$-$C_6$ alkyl, or thiazolyloxy $C_1$-$C_6$ alkyl, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein each heteroaryl and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 17-1c, i.e., compounds of formula 17-1, wherein $R_2$ is hydrogen, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, phenyloxy$C_1$-$C_6$ alkyl, naphthyloxy$C_1$-$C_6$ alkyl, —$C_0$-$C_6$ alkyl-OC(O)NR'R", —$C_0$-$C_6$ alkyl-NR'R", wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and where R' and R" are independently H or $C_1$-$C_6$ alkyl.

In yet another aspect, the invention provides compounds of formula 17-1d, i.e., compounds of formula 17-1, wherein $R_2$ is hydrogen, or —$C_0$-$C_6$ alkyl-OC(O)-heterocycloalkyl, where the heterocycloalkyl group is piperazinyl, pyrrolidinyl, morpholinyl, thiomorpholinyl, thiomorpholinyl S,S-dioxide, tetrahydrofuranyl, or imidazolidinyl, wherein heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl.

In yet another aspect, the invention provides compounds of formula 17-2, i.e., compounds of formula 17-1, 17-1a, 17-1b, 17-1c, or 17-1d, wherein $R_1$ is pyridyl, thiazolyl, imidazolyl, benzofuranyl, benzothienyl, benzimidazolyl, quinolinyl, isoquinolinyl, quinoxalinyl, or quinazolinyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 17-3, i.e., compounds of formula 17-1, 17-1a, 17-1b, 17-1c, or 17-1d, wherein $R_1$ is pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, or quinazolinyloxy $C_1$-$C_6$ alkyl, wherein each heteroaryl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In yet another aspect, the invention provides compounds of formula 17-4, i.e., compounds of formula 17-1, 17-1a, 17-1b, 17-1c, or 17-1d, wherein $R_1$ is —$C_0$-$C_6$ alkyl-OC(O)NR'R", —$C_0$-$C_6$ alkyl-NR'R", —$C_1$-$C_6$ alkyl-OC(O)-piperidinyl, —$C_1$-$C_6$ alkyl-OC(O)-pyrrolidinyl, or —$C_1$-$C_6$ alkyl-OC(O)-morpholinyl, wherein each heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—(CH$_2$)$_{1-2}$—O—, —CO$_2$R', phenyl, pyridazinyl, pyrazinyl, pyrimidyl, thiazolyl, pyridyl, N-methylpyrazolyl, N-benzyl pyrazolyl, oxadiazolyl, oxazolyl, or imidazolyl; and $R_{1a}$ and $R_{2a}$ are both H.

In another aspect, the invention provides compounds of formula 17-5, i.e., compounds of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is —CO$_2$R', —CONR'R", $C_1$-$C_4$ haloalkyl, or $C_1$-$C_4$ hydroxyalkyl; and $R_{1a}$ and $R_{2a}$ are both H. In one embodiment, $R_1$ is as defined above and $R_2$ is H. In another embodiment, $R_1$ is as defined above and $R_2$ is methyl, ethyl, or cyclopropyl. In still another embodiment, $R_1$ is as defined above and $R_2$ is $C_1$-$C_4$ hydroxyalkyl. In a further embodiment, $R_1$ and $R_2$ are independently —CO$_2$—$C_1$-$C_4$ alkyl. In another embodiment, $R_1$ and $R_2$ are independently $C_1$-$C_2$ hydroxyalkyl. In yet another embodiment, $R_1$ is $C_1$-$C_2$ hydroxyalkyl and $R_2$ is methyl or ethyl.

In a further aspect, the invention provides compounds of formula 17-6, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15, wherein $R_1$ is H or $C_1$-$C_6$ alkoxy, $R_2$ is H or $C_1$-$C_6$ alkoxy, and $R_{1a}$ and $R_{2a}$ are both H. In one embodiment, $R_1$ is $C_1$-$C_6$ alkoxy and $R_2$ is H or $C_1$-$C_6$ alkoxy. In another embodiment $R_1$ and $R_2$ are independently $C_1$-$C_6$ alkoxy. In yet another embodiment $R_1$ and $R_2$ are both H.

In another aspect, the invention provides compounds of formula 17-7, i.e., compounds according to any one of formulas 16, 16-1, 16-2, 16-3, 16-4, 16-5, 16-6, 16-6a, 16-7, 16-8, 16-9, 16-10, 16-11, 16-1a, 16-11b, 16-12, 16-13, 16-14, or 16-15 wherein $R_1$ and $R_2$ are both $C_2$-$C_4$ alkenyl optionally substituted with one or more halogens (such as F or Cl), and $R_{1a}$ and $R_{2a}$ are both H. In one embodiment, $R_1$ and $R_2$ are the same. In a further embodiment, $R_1$ and $R_2$ are both $C_2$ alkenyl substituted with two halogens (such as F). $R_1$ and $R_2$ may be cis or trans relative to each other.

In another aspect, the invention provides compounds of formula 17-8, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are the same and are —CH$_2$F, —CH$_2$CF$_3$, —CH$_2$CHF$_2$, CF$_3$, or —CF$_2$CH$_3$.

In another aspect, the invention provides compounds of formula 17-9, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ and $R_2$ are both benzyl or phenethyl, and $R_{1a}$ and $R_{2a}$ are both H. $R_1$ and $R_2$ may be cis or trans relative to each other. In one embodiment, $R_1$ and $R_2$ are both benzyl.

In another aspect, the invention provides compounds of formula 17-10, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ and $R_2$ are both H or $C_1$-$C_4$ alkyl and $R_{1a}$ and $R_{2a}$ are both H. $R_1$ and $R_2$ may be cis or trans relative to each other. In one embodiment, $R_1$ and $R_2$ are both methyl. In another embodiment, both $R_1$ and $R_2$ are both isopropyl. In still another embodiment, one or $R_1$ and $R_2$ is methyl while the other is isopropyl. In yet another embodiment, both of $R_1$ and $R_2$ are ethyl.

In another aspect, the invention provides compounds of formula 17-11, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is H, $C_1$-$C_4$ alkyl, benzyl, phenethyl, or phenyl, where the phenyl portions of $R_1$ are optionally substituted with 1, 2, or 3 groups that are independently halogen, $C_1$-$C_4$ alkyl, or $C_1$-$C_4$ alkoxy and $R_2$ is H or $C_1$-$C_4$ alkyl, and $R_{1a}$ and $R_{2a}$ are both H. $R_1$ and $R_2$ may be cis or trans relative to each other.

In one aspect, the invention provides compounds of formula 17-12, i.e., compounds of formula 17-11 where, $R_2$ is H and $R_1$ is methyl, ethyl or propyl (n or iso), or $R_1$ is H and $R_2$ is methyl, ethyl or propyl (n or iso). In one embodiment, only one of $R_1$ and $R_2$ is isopropyl. In another embodiment, only one of $R_1$ and $R_2$ is ethyl.

In still another aspect, the invention provides compounds of formula 17-13, i.e., compounds of formula 17-11 where, $R_2$ is H and $R_1$ is phenyl substituted with one or two halogens (such as F or Cl), or $R_1$ is H and $R_2$ is phenyl substituted with one or two halogens (such as F or Cl)

In one aspect, the invention provides compounds of formula 17-14, i.e., compounds of formula 17-11 where, $R_2$ is H and $R_1$ is benzyl substituted with one or two groups that are independently halogen (such as F or Cl), methyl, ethyl, methoxy, or ethoxy.

In yet another aspect, the invention provides compounds of formula 17-15, i.e., compounds of formula 17-11 where, $R_2$ is methyl or ethyl, and $R_1$ is methyl, ethyl or propyl (n or iso). In one embodiment, $R_1$ and $R_2$ are both ethyl.

In still yet another aspect, the invention provides compounds of formula 17-16, i.e., compounds of formula 17-11 where, $R_2$ is methyl or ethyl, and $R_1$ is phenyl substituted with one or two halogens (such as F or Cl).

In yet another aspect, the invention provides compounds of formula 17-17, i.e., compounds of formula 17-11 where, $R_2$ is methyl or ethyl, and $R_1$ is benzyl substituted with one or two groups that are independently halogen (such as F or Cl), methyl, ethyl, methoxy, or ethoxy.

In another aspect, the invention provides compounds of formula 17-18, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ and $R_2$ are independently H or —$CO_2$—$C_1$-$C_4$ alkyl, and $R_{1a}$, and $R_{2a}$ are both H. $R_1$ and $R_2$ may be cis or trans relative to each other. In one embodiment, $R_1$ is —$CO_2$—$C_1$-$C_2$ alkyl and $R_2$ is H. In another embodiment, $R_1$ is —$CO_2$-Et and $R_2$ is H. In still another embodiment, $R_1$ is H and $R_2$ is —$CO_2$—$C_1$-$C_2$ alkyl. In yet another embodiment, $R_1$ and $R_2$ are both —$CO_2$-Et.

In another aspect, the invention provides compounds of formula 17-19, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ and $R_3$ form a double bond and $R_{1a}$ and $R_{3a}$ are both H. In one embodiment, $R_2$ is H. In another embodiment, $R_2$ is —$CO_2$—$C_1$-$C_4$ alkyl. In yet another embodiment, $R_2$ is —$CO_2$-Et. In still another embodiment, $R_2$ is methyl or ethyl. In still yet another embodiment, $R_2$ is thiazolyl, pyridyl or pyrimidyl.

In still another aspect, the invention provides compounds of formula 17-20, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is pyridyl, pyrimidyl, $C_3$-$C_6$ cycloalkyl, or thienyl, $R_2$ is H, $C_1$-$C_4$ alkyl, or $C_3$-$C_6$ cycloalkyl, and $R_{1a}$ and $R_{2a}$ are both H, $R_1$ and $R_2$ may be cis or trans relative to each other.

In yet still another aspect, the invention provides compounds of formula 17-21, i.e., compounds of formula 17-20 where, $R_1$ is pyridyl and $R_2$ is H.

In yet another aspect, the invention provides compounds of formula 17-22, i.e., compounds of formula 17-20 where, $R_1$ is pyridyl and $R_2$ is methyl or ethyl.

In a further aspect, the invention provides compounds of formula 17-23, i.e., compounds of formula 17-20 where, $R_1$ is pyridyl and $R_2$ is $C_3$, $C_5$, or $C_6$ cycloalkyl. In another embodiment, $R_2$ is $C_3$ cycloalkyl.

In still another aspect, the invention provides compounds of formula 17-24, i.e., compounds of formula 17-20 where, $R_1$ is pyrimidyl and $R_2$ is H.

In another aspect, the invention provides compounds of formula 17-25, i.e., compounds of formula 17-20 where, $R_1$ is pyrimidyl and $R_2$ is methyl or ethyl.

In yet another aspect, the invention provides compounds of formula 17-26, i.e., compounds of formula 17-20 where, $R_1$ is pyrimidyl and $R_2$ is $C_3$, $C_5$, or $C_6$ cycloalkyl.

In still another aspect, the invention provides compounds of formula 17-27, i.e., compounds of formula 17-20 where, $R_1$ is $C_3$, $C_5$, or $C_6$ cycloalkyl and $R_2$ is H.

In yet still another aspect, the invention provides compounds of formula 17-28, i.e., compounds of formula 17-20 where, $R_1$ is $C_3$, $C_5$, or $C_6$ cycloalkyl and $R_2$ is methyl or ethyl.

In yet another aspect, the invention provides compounds of formula 17-29, i.e., compounds of formula 17-20 where, $R_1$ is $C_3$, $C_5$, or $C_6$ cycloalkyl and $R_2$ is $C_3$, $C_5$, or $C_6$ cycloalkyl. In one embodiment one of $R_1$ and $R_2$ is $C_3$ cycloalkyl. In another embodiment, both of $R_1$ and $R_2$ are $C_3$ cycloalkyl.

In still another aspect, the invention provides compounds of formula 17-30, i.e., compounds of formula 17-20 where, $R_1$ is thienyl and $R_2$ is H.

In yet another aspect, the invention provides compounds of formula 17-31, i.e., compounds of formula 17-20 where, $R_1$ is thienyl and $R_2$ is methyl or ethyl.

In yet another aspect, the invention provides compounds of formula 17-32, i.e., compounds of formula 17-20 where, $R_1$ is thienyl and $R_2$ is $C_3$, $C_5$, or $C_6$ cycloalkyl. In one embodiment, $R_2$ is $C_3$ cycloalkyl.

In a further aspect, the invention provides compounds of formula 17-33, i.e., compounds according to any one of formulas 16, 16-1, 16-2, 16-3, 16-4, 16-5, 16-6, 16-6a, 16-7, 16-8, 16-9, 16-10, 16-11, 16-1a, 16-11b, 16-12, 16-13, 16-14, or 16-15 wherein $R_2$ is pyridyl, pyrimidyl, —$CO_2$—$C_1$-$C_4$ alkyl, $C_1$-$C_4$ alkyl, —$C_1$-$C_4$ alkyl-OC(O)NR'R'', benzimidazolyl, thiazolyl, or imidazolyl, and $R_1$ is H, methyl, or ethyl; where R' and R'' are independently H or $C_1$-$C_4$ alkyl. When $R_1$ is methyl or ethyl, $R_1$ and $R_2$ may be cis or trans relative to each other.

In still another aspect, the invention provides compounds of formula 17-34, i.e., compounds of formula 17-33 where, $R_2$ is pyridyl, pyrimidyl, thiazolyl, benzimidazolyl, or imidazolyl. In one embodiment, $R_2$ is thiazolyl and $R_1$ is H. In another embodiment, $R_2$ is thiazolyl and $R_1$ is methyl or ethyl. In still another embodiment, $R_2$ is pyridyl and $R_1$ is H. In another embodiment, $R_2$ is pyridyl and $R_1$ is methyl or ethyl. In yet another embodiment, $R_2$ is pyrimidyl and $R_1$ is H. In another embodiment, $R_2$ is pyrimidyl and $R_1$ is methyl or ethyl.

In yet another aspect, the invention provides compounds of formula 17-35, i.e., compounds of formula 17-33 where, $R_2$ is —$CO_2$-Me or —$CO_2$-Et.

In yet another aspect, the invention provides compounds of formula 17-36, i.e., compounds of formula 17-33 where, $R_2$ is methyl, ethyl, or propyl (either n or iso).

In yet another aspect, the invention provides compounds of formula 17-37, i.e., compounds of formula 17-33 where, $R_2$ is —$CH_2$—OC(O)NR'R", where R' and R" are independently H or $C_1$-$C_2$ alkyl. In one embodiment, $R_1$ is H. In another embodiment, $R_1$ is ethyl.

In yet still another aspect, the invention provides compounds of formula 17-38, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_2$ and $R_{2a}$ combine to form oxo.

In still another aspect, the invention provides compounds of formula 17-39, i.e., compounds of formula 17-38 where, $R_1$ is H, $C_1$-$C_4$ alkyl, $C_3$-$C_6$ cycloalkyl, or —$C_1$-$C_4$ alkyl-OC(O)NR'R", where R' and R" are independently H or $C_1$-$C_4$ alkyl, and $R_{1a}$ is H.

In still another aspect, the invention provides compounds of formula 17-40, i.e., compounds of formula 17-38 where, $R_1$ is H, methyl or ethyl. In one embodiment, $R_1$ is H. In another embodiment, $R_1$ is methyl or ethyl.

In yet another aspect, the invention provides compounds of formula 17-41, i.e., compounds of formula 17-38 where, $R_1$ is $C_3$, $C_5$, or $C_6$ cycloalkyl. In one embodiment, $R_1$ is $C_3$ cycloalkyl. In another embodiment, $R_1$ is $C_5$ or $C_6$ cycloalky.

In still yet another aspect, the invention provides compounds of formula 17-42, i.e., compounds of formula 17-38 where, $R_1$ is —$C_1$-$C_2$ alkyl-OC(O)NR'R", where R' and R" are independently H, methyl, or ethyl.

In yet still another aspect, the invention provides compounds of formula 17-43, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_3$ is NR'R", OH, halogen, $R_{3a}$ is H or halogen; or $R_3$ and $R_{3a}$ combine to form oxo, =N—OH, or =N—O—$C_1$-$C_4$ alkyl. $R_1$ is H, pyridyl, pyrimidyl, $C_1$-$C_4$ alkyl; $R_2$ is H, $C_1$-$C_4$ alkyl, pyrimidyl, pyridyl, thiazolyl, or imidazolyl; and $R_{1a}$ and $R_{2a}$ are both H.

In still yet another aspect, the invention provides compounds of formula 17-44, i.e., compounds of formula 17-43 where, $R_3$ is NR'R"; $R_{3a}$ is H; and $R_1$ and $R_2$ are independently methyl, ethyl or propyl (n or iso), In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In still yet another aspect, the invention provides compounds of formula 17-45, i.e., compounds of formula 17-43 where, $R_3$ is NR'R"; $R_{3a}$ is H; and $R_1$ is H, methyl, ethyl or propyl (n or iso); and $R_2$ is H, pyrimidyl, pyridyl, thiazolyl, or imidazolyl. In one embodiment, $R_1$ is H and $R_2$ is pyrimidyl or pyridyl. In another embodiment, $R_1$ is H and $R_2$ is thiazolyl, or imidazolyl. In one embodiment, $R_1$ is methyl, ethyl or propyl (n or iso) and $R_2$ is pyrimidyl or pyridyl. In another embodiment, $R_1$ is methyl, ethyl or propyl (n or iso) and $R_2$ is thiazolyl, or imidazolyl.

In another aspect, the invention provides compounds of formula 17-46, i.e., compounds of formula 17-43 where, $R_3$ is NR'R"; $R_{3a}$ is H; and $R_1$ is pyridyl or pyrimidyl; and $R_2$ is H.

In still yet another aspect, the invention provides compounds of formula 17-47, i.e., compounds of formula 17-43 where, $R_3$ is NR'R"; $R_{3a}$ is H; $R_1$ is pyridyl, or pyrimidyl; and $R_2$ is pyrimidyl, pyridyl, thiazolyl, or imidazolyl.

In another aspect, the invention provides compounds of formula 17-48, i.e., compounds of formula 17-43 where $R_1$ is H and $R_2$ is methyl, ethyl or propyl (n or iso). In another embodiment $R_2$ is methyl. In yet another embodiment $R_2$ is ethyl. In another embodiment $R_2$ is propyl (n or iso).

In another aspect, the invention provides compounds of formula 17-49, i.e., compounds of formula 17-43 where $R_2$ is H and $R_1$ is methyl, ethyl or propyl (n or iso). In another embodiment $R_1$ is methyl. In yet another embodiment $R_1$ is ethyl. In another embodiment $R_1$ is propyl (n or iso).

In still yet another aspect, the invention provides compounds of formula 17-50, i.e., compounds of formula 17-43 where, $R_3$ is halogen; $R_{3a}$ is H or halogen; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other. In still another embodiment $R_3$ and $R_{3a}$ are the same. When $R_3$ and $R_{3a}$ are the same, they may both be F.

In still yet another aspect, the invention provides compounds of formula 17-51, i.e., compounds of formula 17-43 where, $R_3$ is OH; $R_{3a}$ is H; and $R_1$ and $R_2$ are independently methyl, ethyl or propyl (n or iso). In one embodiment, $R_1$ and $R_2$ are the same, and they are cis, relative to each other. In another embodiment, $R_1$ and $R_2$ are the same, and they are trans, relative to each other. In still another embodiment $R_1$ is methyl or ethyl and $R_2$ is methyl, ethyl or propyl (n or iso). In another embodiment $R_1$ is methyl and $R_2$ is methyl, ethyl or propyl (n or iso), and $R_1$ and $R_2$ are cis, relative to each other. In yet another embodiment $R_1$ is methyl and $R_2$ is methyl, ethyl or propyl (n or iso), and $R_1$ and $R_2$ are trans, relative to each other. In another embodiment $R_1$ is ethyl and $R_2$ is methyl, ethyl or propyl (n or iso), and $R_1$ and $R_2$ are cis, relative to each other. In yet another embodiment $R_1$ is ethyl and $R_2$ is methyl, ethyl or propyl (n or iso), and $R_1$ and $R_2$ are trans, relative to each other.

In yet still another aspect, the invention provides compounds of formula 17-52, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_3$ and $R_{3a}$ combine to form oxo, =N—OH, or =N—O—$C_1$-$C_4$ alkyl; $R_1$ is H, pyridyl, pyrimidyl, $C_1$-$C_4$ alkyl (methyl, ethyl), or $C_3$-$C_6$ cycloalkyl; $R_2$ is H, $C_1$-$C_4$ alkyl (methyl, ethyl, isopropyl), pyrimidyl, pyridyl, thiazolyl, or imidazolyl; and $R_{1a}$ and $R_{2a}$ are both H.

In another aspect, the invention provides compounds of formula 17-53, i.e., compounds of formula 17-52 where, $R_3$ and $R_{3a}$ combine to form oxo; and $R_1$ is $C_3$-$C_6$ cycloalkyl, pyridyl or pyrimidyl.

In yet another aspect, the invention provides compounds of formula 17-54, i.e., compounds of formula 17-53 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 17-55, i.e., compounds of formula 17-52 where, $R_3$ and $R_{3a}$ combine to form oxo; and $R_1$ is H or $C_1$-$C_4$ alkyl (such as methyl, ethyl or isopropyl).

In another aspect, the invention provides compounds of formula 17-56, i.e., compounds of formula 17-55 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 17-57, i.e., compounds of formula 17-52 where, $R_1$ and $R_2$ are both H.

In still yet another aspect, the invention provides compounds of formula 17-58, i.e., compounds according to either formula 17-53 or 17-55 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 17-59, i.e., compounds of formula 17-52 where, $R_3$ and $R_{3a}$ combine to form =N—OH; and $R_1$ is $C_3$-$C_6$ cycloalkyl, pyridyl or pyrimidyl.

In yet another aspect, the invention provides compounds of formula 17-60, i.e., compounds of formula 17-59 where, $R_2$ is H, $C_1$-$C_4$ alkyl. In one embodiment, $R_2$ is methyl.

In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 17-61, i.e., compounds of formula 17-52 where, $R_3$ and $R_{3a}$ combine to form =N—OH; and $R_1$ is H or $C_1$-$C_4$ alkyl (such as methyl, ethyl or isopropyl).

In another aspect, the invention provides compounds of formula 17-62, i.e., compounds of formula 17-61 where, $R_2$ is H, $C_1$-$C_4$ alkyl. In one embodiment, $R_2$ is methyl.

In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other.

In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 17-63, i.e., compounds according to either formula 17-59 or 17-61 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl. In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In another aspect, the invention provides compounds of formula 17-64, i.e., compounds of formula 17-52 where, $R_3$ and $R_{3a}$ combine to form =N—O—$C_1$-$C_4$ alkyl; and $R_1$ is $C_3$-$C_6$ cycloalkyl, pyridyl or pyrimidyl.

In yet another aspect, the invention provides compounds of formula 17-65, i.e., compounds of formula 17-64 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, $R_1$ and $R_2$ are cis relative to each other. In another embodiment, $R_1$ and $R_2$ are trans relative to each other. In still another embodiment, $R_1$ is pyrimidyl and $R_2$ is H. In yet still another embodiment, $R_1$ is pyridyl and $R_2$ is H. In a further embodiment, $R_1$ is cyclopropyl and $R_2$ is H. In a further embodiment, $R_1$ is cyclopropyl and $R_2$ is H.

In still yet another aspect, the invention provides compounds of formula 17-66, i.e., compounds of formula 17-52 where, $R_3$ and $R_{3a}$ combine to form =N—O—$C_1$-$C_4$ alkyl; and $R_1$ is H or $C_1$-$C_4$ alkyl (such as methyl, ethyl or isopropyl).

In another aspect, the invention provides compounds of formula 17-67, i.e., compounds of formula 17-66 where, $R_2$ is H, $C_1$-$C_4$ alkyl. In one embodiment, $R_2$ is methyl. In another embodiment, $R_2$ is ethyl, in still another embodiment, $R_2$ is isopropyl. In still another embodiment, when $R_1$ is $C_1$-$C_4$ alkyl, then $R_1$ and $R_2$ are cis relative to each other. In still another embodiment, when $R_1$ is $C_1$-$C_4$ alkyl, then $R_1$ and $R_2$ are trans relative to each other. In another embodiment, $R_1$ and $R_2$ are the same, and are methyl or ethyl.

In still yet another aspect, the invention provides compounds of formula 17-68, i.e., compounds according to either formula 17-64 or 17-66 where, $R_2$ is pyrimidyl, pyridyl, thiazolyl, or imidazolyl. In one embodiment, $R_2$ is pyrimidyl or pyridyl. In another embodiment, $R_2$ is thiazolyl, or imidazolyl. In still another embodiment, when $R_1$ is not H, then $R_1$ and $R_2$ are cis relative to each other. In still another embodiment, when $R_1$ is not H, then $R_1$ and $R_2$ are trans relative to each other. In still another embodiment, $R_1$ is pyrimidyl and $R_2$ is pyrimidyl or pyridyl. In yet still another embodiment, $R_1$ is pyridyl and $R_2$ is pyrimidyl or pyridyl, In a further embodiment, $R_1$ is cyclopropyl and $R_2$ is pyrimidyl or pyridyl. In a further embodiment, $R_1$ is cyclopropyl and $R_2$ is pyrimidyl or pyridyl.

In a further aspect, the invention provides compounds of formula 17-69, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is pyridyl, pyrimidyl, —$CO_2$—$C_1$-$C_4$ alkyl, $C_1$-$C_4$ alkyl, —$C_1$-$C_4$ alkyl-OC(O)NR'R", benzimidazolyl, thiazolyl, or imidazolyl, and $R_2$ is H, methyl, or ethyl; where R' and R" are independently H or $C_1$-$C_4$ alkyl. When $R_2$ is methyl or ethyl, $R_1$ and $R_2$ may be cis or trans relative to each other.

In still another aspect, the invention provides compounds of formula 17-70, i.e., compounds of formula 17-69 where, $R_1$ is pyridyl, pyrimidyl, thiazolyl, benzimidazolyl, or imidazolyl.

In yet another aspect, the invention provides compounds of formula 17-71, i.e., compounds of formula 17-69 where, $R_1$ is —$CO_2$-Me or $CO_2$-Et.

In yet another aspect, the invention provides compounds of formula 17-72, i.e., compounds of formula 17-69 where, $R_1$ is methyl, ethyl, or propyl (either n or iso).

In yet another aspect, the invention provides compounds of formula 17-73, i.e., compounds of formula 17-69 where, $R_1$ is —$CH_2$—OC(O)NR'R", where R' and R" are independently H or $C_1$-$C_2$ alkyl. In one embodiment, $R_2$ is H. In another embodiment, $R_2$ is ethyl.

In a further aspect, the invention provides compounds of formula 17-74, i.e., compounds according to any one of formulas 16, 16-1, 16-2, 16-3, 16-4, 16-5, 16-6, 16-6a, 16-7, 16-8, 16-9, 16-10, 16-11, 16-11a, 16-11b, 16-12, 16-13, 16-14, or 16-15 wherein $R_1$ is —$C_1$-$C_4$ alkyl-OC(O)NR'R"; $R_2$ is H or —$C_1$-$C_4$ alkyl-OC(O)NR'R"; and $R_{1a}$, $R_2$, $R_3$, and $R_{3a}$ are H; where R' and R" are independently H or $C_1$-$C_3$ alkyl. In one embodiment, $R_1$ and $R_2$ are both —$CH_2$—OC(O)NR'R". In still another embodiment, R' and R" are both H, methyl or ethyl. In yet another embodiment, at least one of R' and R" is isopropyl.

In yet another aspect, the invention provides compounds of formula 17-75, i.e., compounds according to any one of formulas 16 up to and including 16-15, or any one of formulas 17, up to and including 17-74, wherein the heterocycloalkyl group is morpholinyl optionally substituted with one or more groups that are independently halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 17-75a, i.e., compounds of formula 17-75 where the morpholinyl group is not attached to the sulfur of the $SO_2$ group via the ring nitrogen.

In still another aspect, the invention provides compounds of formula 17-75b, i.e., compounds of formula 17-75 where the morpholinyl group is attached to the sulfur of the $SO_2$ group via the ring nitrogen.

In yet another aspect, the invention provides compounds of formula 17-76, i.e., compounds according to any one of formulas 16 up to and including 16-15, or any one of formulas 17, up to and including 17-74, wherein the heterocycloalkyl group is thiomorpholinyl optionally substituted with one or more groups that are independently halogen, $C_1$-$C_6$ alkyl, $C_1$-$C_6$ alkoxy, haloalkyl, haloalkoxy, hydroxyl, CN, aryloxy, arylalkyloxy —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 17-76a, i.e., compounds of formula 17-76 where the thiomorpholinyl group is not attached to the sulfur of the $SO_2$ group via the ring nitrogen.

In still another aspect, the invention provides compounds of formula 17-76b, i.e., compounds of formula 17-76 where the thiomorpholinyl group is attached to the sulfur of the $SO_2$ group via the ring nitrogen.

In yet another aspect, the invention provides compounds of formula 17-77, i.e., compounds according to any one of formulas 16 up to and including 16-15, or any one of formulas 17, up to and including 17-74, wherein the heterocycloalkyl group is thiomorpholinyl S,S-dioxide optionally substituted with one or more groups that are independently halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 17-77a, i.e., compounds of formula 17-77 where the thiomorpholinyl group is not attached to the sulfur of the $SO_2$ group via the ring nitrogen.

In still another aspect, the invention provides compounds of formula 17-77b, i.e., compounds of formula 17-77 where the thiomorpholinyl group is attached to the sulfur of the $SO_2$ group via the ring nitrogen.

In yet another aspect, the invention provides compounds of formula 17-78, i.e., compounds according to any one of formulas 16 up to and including 16-15, or any one of formulas 17, up to and including 17-74, wherein the heterocycloalkyl group is piperidinyl optionally substituted with one or more groups that are independently halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 17-78a, i.e., compounds of formula 17-78 where the thiomorpholinyl group is not attached to the sulfur of the $SO_2$ group via the ring nitrogen.

In still another aspect, the invention provides compounds of formula 17-78b, i.e., compounds of formula 17-78 where the thiomorpholinyl group is attached to the sulfur of the $SO_2$ group via the ring nitrogen.

In yet another aspect, the invention provides compounds of formula 17-79, i.e., compounds according to any one of formulas 16 up to and including 16-15, or any one of formulas 17, up to and including 17-74, wherein the heterocycloalkyl group is piperazinyl optionally substituted with one or more groups that are independently halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of formula 17-79a, i.e., compounds of formula 17-79 where the thiomorpholinyl group is not attached to the sulfur of the $SO_2$ group via the ring nitrogen.

In still another aspect, the invention provides compounds of formula 17-79b, i.e., compounds of formula 17-79 where the thiomorpholinyl group is attached to the sulfur of the $SO_2$ group via the ring nitrogen.

In another aspect, the invention provides compounds of formula 18, i.e., compounds of formulas 1 or 2, wherein $R_1$ is phenyl, benzyl, pyridazinyl, pyrazinyl, pyrimidyl, thiazolyl, pyridyl, N-methylpyrazolyl, N-benzyl pyrazolyl, oxadiazolyl, oxazolyl, or imidazolyl, —CO₂R', —CONR'R", methyl, Ethyl, i-Propyl, i-Butyl, s-Butyl,

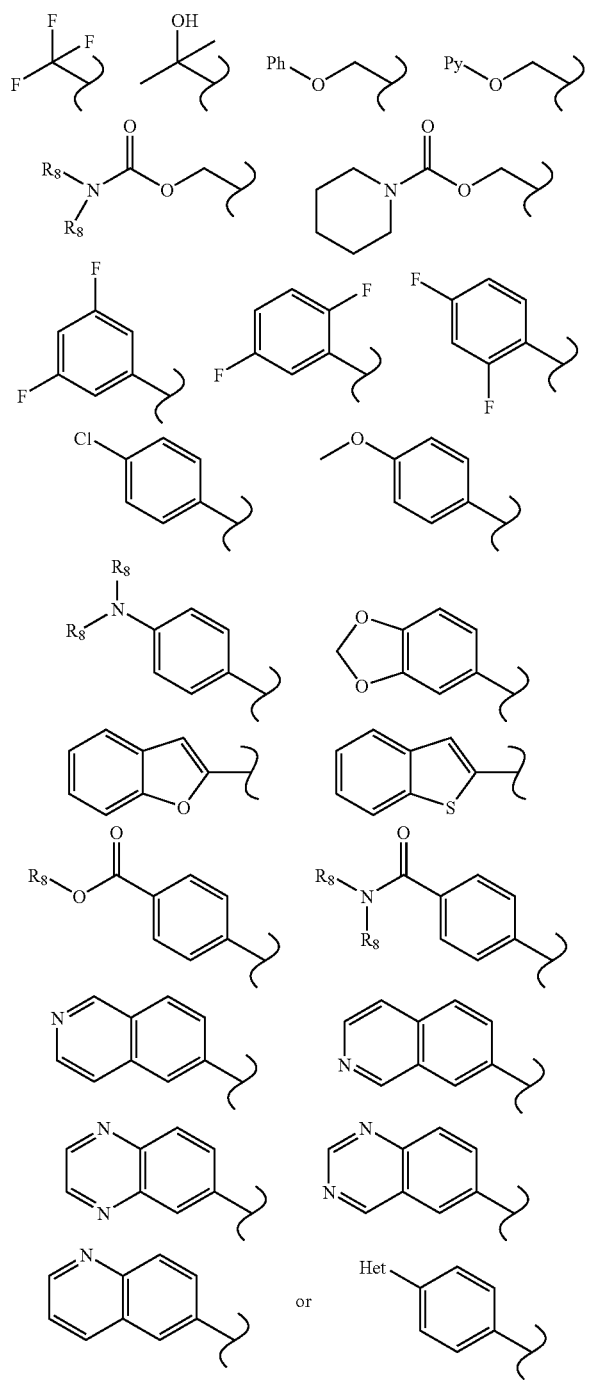

where Het at each occurrence is independently pyridazinyl, pyrazinyl, pyrimidyl, thiazolyl, pyridiyl, N-methylpyrazolyl, N-benzyl pyrazolyl, oxadiazolyl, oxazolyl, or imidazolyl;

Ph is phenyl;

Py is pyridyl;

the B-ring is pyrazolyl, imidazolyl, pyrrolyl, triazolyl, pyrrolidinyl, pyrazolidinyl, imidazolidinyl, isoxazolyl, pyrimidyl or pyridyl, each of which is optionally substituted at a substitutable position with a group that is independently $C_1$-$C_6$ alkyl, $C_1$-$C_6$ alkoxy, amino, $C_1$-$C_6$ alkylamino, $C_1$-$C_6$ dialkylamino, $C_1$-$C_6$ alkylthio, halo, $C_1$-$C_2$ haloalkyl, $C_1$-$C_2$ haloalkoxy, or phenyl;

$R_8$=H or $C_1$-$C_6$ alkyl (such as methyl);

$R_2$=methyl, ethyl, isopropyl, vinyl, or allyl; and

R'=H or methyl.

In another aspect, the invention provides compounds of formula 18-1, i.e., compounds of formula 18 where the B-ring has the formula:

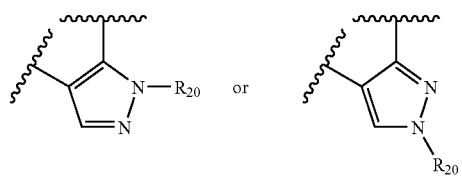

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In still another aspect, the invention provides compounds of formula 18-2, i.e., compounds of formula 18-1 where $R_{20}$ is H, or $C_1$-$C_6$ alkyl. In another embodiment, $R_{20}$ is phenyl. In yet another embodiment, $R_{20}$ is H. In still another embodiment, $R_{20}$ is methyl or ethyl.

In another aspect, the invention provides compounds of formula 18-3, i.e., compounds of formula 18 where the B-ring has the formula:

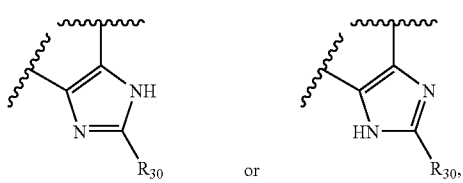

where $R_{30}$ is H, $C_1$-$C_4$ alkyl, $C_1$-$C_4$ alkoxy, amino, $C_1$-$C_4$ alkylamino, $C_1$-$C_4$ dialkylamino, $C_1$-$C_4$ alkythio, halo, $CF_3$, or phenyl.

In another aspect, the invention provides compounds of formula 18-4, i.e., compounds of formula 18-3 where, $R_{30}$ is H, or $C_1$-$C_6$ alkyl. In another embodiment, $R_{30}$ is phenyl. In still another embodiment, when the $R_{30}$ group is attached to a carbon, $R_{30}$ is $C_1$-$C_4$ alkoxy, $C_1$-$C_4$ alkythio, halo, $CF_3$, or phenyl. In yet another embodiment, $R_{30}$ is H.

In another aspect, the invention provides compounds of formula 18-5, i.e., compounds of formula 18-4, where $R_{30}$ is amino, $C_1$-$C_4$ alkylamino, $C_1$-$C_4$ dialkylamino.

In another aspect, unless defined to the contrary, the invention provides compounds according to any of the above formulas where both $R_3$ and $R_{3a}$ are H.

In another aspect, the invention provides compounds selected from:

5-(4-chlorophenylsulfonyl)-4,6-dicyclopropyl-4,5,6,7-tetrahydro-1H-pyrazolo[4,3-c]pyridine;

cis-(5-(4-chlorophenylsulfonyl)-4-ethyl-4,5,6,7-tetrahydro-1H-pyrazolo[4,3-c]pyridin-6-yl)methanol;

5-(4-chlorophenylsulfonyl)-6-(pyrimidin-5-yl)-5,6-dihydro-1H-pyrazolo[4,3-c]pyridin-7(4H)-one;

5-(4-chlorophenylsulfonyl)-4-(pyrimidin-5-yl)-5,6-dihydro-1H-pyrazolo[4,3-c]pyridin-7(4H)-one;

5-(4-chlorophenylsulfonyl)-6-cyclopropyl-6,7-dihydro-1H-pyrazolo[4,3-c]pyridin-4(5H)-one;

4-(pyrimidin-5-yl)-5-(4-(trifluoromethyl)phenylsulfonyl)-4,5,6,7-tetrahydro-1H-pyrazolo[4,3-c]pyridine;

6-methyl-4-(pyrimidin-5-yl)-5-(4-(trifluoromethyl)phenylsulfonyl)-4,5,6,7-tetrahydro-1H-pyrazolo[4,3-c]pyridine;

4,6-dimethyl-5-(4-(trifluoromethyl)phenylsulfonyl)-5,6-dihydro-1H-pyrazolo[4,3-c]pyridin-7(4H)-one;

(4-(pyrimidin-5-yl)-5-(4-(trifluoromethyl)phenylsulfonyl)-4,5,6,7-tetrahydro-1H-pyrazolo[4,3-c]pyridin-6-yl)methanol;

5-(4-chlorophenylsulfonyl)-6-methyl-4-(pyrimidin-5-yl)-4,5,6,7-tetrahydro-1H-pyrazolo[4,3-c]pyridine;

5-(4-chlorophenylsulfonyl)-6-cyclopropyl-4-(pyrimidin-5-yl)-4,5,6,7-tetrahydro-1H-pyrazolo[4,3-c]pyridine;

5-(4-fluorophenylsulfonyl)-4,6-dimethyl-5,6-dihydro-1H-pyrazolo[4,3-c]pyridin-7(4H)-one;

4,6-dimethyl-5-(pyridin-2-ylsulfonyl)-5,6-dihydro-1H-pyrazolo[4,3-c]pyridin-7(4H)-one;

5-(4-chlorophenylsulfonyl)-4,6-bis(,1-difluoroethyl)-4,5,6,7-tetrahydro-1H-pyrazolo[4,3-c]pyridine;

5-(4-chlorophenylsulfonyl)-4,6-bis(difluoromethyl)-4,5,6,7-tetrahydro-1H-pyrazolo[4,3-c]pyridine;

1,1'-(5-(4-chlorophenylsulfonyl)-4,5,6,7-tetrahydro-1H-pyrazolo[4,3-c]pyridine-4,6-diyl)diethanone;

5-(4-chlorophenylsulfonyl)-4,6-bis(2,2-difluorovinyl)-4,5,6,7-tetrahydro-1H-pyrazolo[4,3-c]pyridine;

5-(4-chlorophenylsulfonyl)-4,6-bis(2,2-difluoroethyl)-4,5,6,7-tetrahydro-1H-pyrazolo[4,3-c]pyridine;

5-(4-chlorophenylsulfonyl)-4,6-bis(fluoromethyl)-4,5,6,7-tetrahydro-1H-pyrazolo[4,3-c]pyridine;

5-(4-chlorophenylsulfonyl)-4,6-bis(difluoro(methoxy)methyl)-4,5,6,7-tetrahydro-1H-pyrazolo[4,3-c]pyridine;

5-(4-chlorophenylsulfonyl)-4,6-bis((trifluoromethoxy)methyl)-4,5,6,7-tetrahydro-1H-pyrazolo[4,3-c]pyridine;

5-(4-chlorophenylsulfonyl)-4,6-bis(2,2,2-trifluoroethyl)-4,5,6,7-tetrahydro-1H-pyrazolo[4,3-c]pyridine;

5-(4-chlorophenylsulfonyl)-4,6-diisopropyl-4,5,6,7-tetrahydro-1H-pyrazolo[4,3-c]pyridine;

5'-(4-chlorophenylsulfonyl)-1',5',6',7'-tetrahydrospiro[cyclopropane-1,4'-pyrazolo[4,3-c]pyridine];

6-methyl-4-(pyrimidin-5-yl)-5-(4-(trifluoromethyl)phenylsulfonyl)-5,6-dihydro-1H-pyrazolo[4,3-c]pyridin-7(4H)-one;

6-methyl-4-(pyridin-3-yl)-5-(4-(trifluoromethyl)phenylsulfonyl)-5,6-dihydro-1H-pyrazolo[4,3-c]pyridin-7(4H)-one;

6-methyl-4-(pyridin-4-yl)-5-(4-(trifluoromethyl)phenylsulfonyl)-5,6-dihydro-1H-pyrazolo[4,3-c]pyridin-7(4H)-one;

5-(4-chlorophenylsulfonyl)-4,6-diethyl-5,6-dihydro-1H-pyrazolo[4,3-c]pyridin-7(4H)-one O-methyl oxime;

5-(4-chlorophenylsulfonyl)-4,6-diethyl-N,N-dimethyl-4,5,6,7-tetrahydro-1H-pyrazolo[4,3-c]pyridin-7-amine;

5-(4-chlorophenylsulfonyl)-4,6-diethyl-4,5,6,7-tetrahydro-1H-pyrazolo[4,3-c]pyridin-7-amine;

5-(4-chlorophenylsulfonyl)-4,6-diethyl-4,5,6,7-tetrahydro-1H-pyrazolo[4,3-c]pyridin-7-ol;

5-(4-chlorophenylsulfonyl)-4,6-diethyl-7-fluoro-4,5,6,7-tetrahydro-1H-pyrazolo[4,3-c]pyridine;

5-(4-chlorophenylsulfonyl)-4,6-diethyl-7,7-difluoro-4,5,6,7-tetrahydro-1H-pyrazolo[4,3-c]pyridine;

6-methyl-4-(thiazol-2-yl)-5-(4-(trifluoromethyl)phenylsulfonyl)-5,6-dihydro-1H-pyrazolo[4,3-c]pyridin-7(4H)-one;

4-(1H-imidazol-5-yl)-6-methyl-5-(4-(trifluoromethyl)phenylsulfonyl)-5,6-dihydro-1H-pyrazolo[4,3-c]pyridin-7(4H)-one;

4-(1H-imidazol-2-yl)-6-methyl-5-(4-(trifluoromethyl)phenylsufonyl)-5,6-dihydro-1H-pyrazolo[4,3-c]pyridin-7(4H)-one;

5-(4-chlorophenylsulfonyl)-4,6-bis(trifluoromethyl)-4,5,6,7-tetrahydro-1H-pyrazolo[4,3-c]pyridine;

5-(4-chlorophenylsulfonyl)-4-isopropyl-5,6-dihydro-1H-pyrazolo[4,3-c]pyridin-7(4H)-one;

5-(4-chlorophenylsulfonyl)-6-phenyl-4,5,6,7-tetrahydro-1H-pyrazolo[4,3-c]pyridine;

6-benzyl-5-(4-chlorophenylsulfonyl)-4,5,6,7-tetrahydro-1H-pyrazolo[4,3-c]pyridine;

5-(4-chlorophenylsulfonyl)-6-isopropyl-4,5,6,7-tetrahydro-1H-pyrazolo[4,3-c]pyridine;

5-(4-chlorophenylsulfonyl)-6-(4-fluorophenyl)-4,5,6,7-tetrahydro-1H-pyrazolo[4,3-c]pyridine;

6-(4-chlorophenyl)-5-(4-chlorophenylsulfonyl)-4,5,6,7-tetrahydro-1H-pyrazolo[4,3-c]pyridine;

5-(4-chlorophenylsulfonyl)-6-(3,5-difluorophenyl)-4,5,6,7-tetrahydro-1H-pyrazolo[4,3-c]pyridine;

4-(4-chlorophenyl)-5-(4-chlorophenylsulfonyl)-6-ethyl-4,5,6,7-tetrahydro-1H-pyrazolo[4,3-c]pyridine;

6-(4-chlorophenyl)-5-(4-chlorophenylsulfonyl)-3-(trifluoromethyl)-4,5,6,7-tetrahydro-1H-pyrazolo[4,3-c]pyridine;

6-(4-chlorophenyl)-5-(4-chlorophenylsulfonyl)-4-ethyl-4,5,6,7-tetrahydro-1H-pyrazolo[4,3-c]pyridine;

5-(4-chlorophenylsulfonyl)-4,6-dimethyl-4,5,6,7-tetrahydro-1H-pyrazolo[4,3-c]pyridine;

5-(4-chlorophenylsulfonyl)-6-(pyridin-3-yl)-4,5,6,7-tetrahydro-1H-pyrazolo[4,3-c]pyridine;

5-(4-chlorophenylsulfonyl)-6-(pyridin-4-yl)-4,5,6,7-tetrahydro-1H-pyrazolo[4,3-c]pyridine;

5-(4-chlorophenylsulfonyl)-4,6-diethyl-4,5,6,7-tetrahydro-1H-pyrazolo[4,3-c]pyridine;

5-(4-chlorophenylsulfonyl)-6-(pyrimidin-5-yl)-4,5,6,7-tetrahydro-1H-pyrazolo[4,3-c]pyridine;

5-(4-Chloro-benzenesulfonyl)-4-pyrimidin-5-yl-4,5,6,7-tetrahydro-1H-pyrazolo[4,3-c]pyridine;

ethyl 5-(4-chlorophenylsulfonyl)-4,5,6,7-tetrahydro-1H-pyrazolo[4,3-c]pyridine-4-carboxylate;

ethyl 5-(4-chlorophenylsulfonyl)-4,5,6,7-tetrahydro-1H-pyrazolo[4,3-c]pyridine-6-carboxylate;

5-(4-chlorophenylsulfonyl)-6-ethyl-6,7-dihydro-1H-pyrazolo[4,3-c]pyridin-4(5H)-one;

(5-(4-chlorophenylsulfonyl)-4,5,6,7-tetrahydro-1H-pyrazolo[4,3-c]pyridin-6-yl)methanol;

5-(4-chlorophenylsulfonyl)-4,6-diethyl-5,6-dihydro-1H-pyrazolo[4,3-c]pyridin-7(4H)-one;

diethyl 5-(4-chlorophenylsulfonyl)-4,5,6,7-tetrahydro-1H-pyrazolo[4,3-c]pyridine-4,6-dicarboxylate;

5-(4-chlorophenylsulfonyl)-4,5,6,7-tetrahydro-1H-pyrazolo[4,3-c]pyridine-4,6-diyl)dimethanol;

(5-(4-chlorophenylsulfonyl)-4,5,6,7-tetrahydro-1H-pyrazolo[4,3-c]pyridin-4-yl)methyl dimethylcarbamate, 5-(4-chlorophenylsulfonyl)-4,6-diethyl-5,6-dihydro-1H-pyrazolo[4,3-c]pyridin-7(4H)-one;

(5-(4-chlorophenylsulfonyl)-1-(dimethylcarbamoyl)-4,5,6,7-tetrahydro-1H-pyrazolo[4,3-c]pyridin-4-yl)methyl dimethylcarbamate;

4,6-diethyl-5-(pyridin-2-ylsulfonyl)-4,5,6,7-tetrahydro-1H-pyrazolo[4,3-c]pyridine;

4-(1H-benzoimidazol-2-yl)-5-(4-chloro-benzenesulfonyl)-4,5,6,7-tetrahydro-1H pyrazolo[4,3-c]pyridine;

5-(4-chlorophenylsulfonyl)-4,6-diethyl-5,6-dihydro-1H-pyrazolo[4,3-c]pyridin-7(4H)-one oxime;
ethyl 5-(4-chlorophenylsulfonyl)-6-ethyl-4,5,6,7-tetrahydro-1H-pyrazolo[4,3-c]pyridine-4-carboxylate;
4,6-diethyl-5-(4-fluorophenylsulfonyl)-4,5,6,7-tetrahydro-2H-pyrazolo[4,3-c]pyridine;
5-(4-chlorophenylsulfonyl)-6-ethyl-4,5,6,7-tetrahydro-1H-pyrazolo[4,3-c]pyridin-4-yl)methyl dimethylcarbamate;
5-(4-chlorophenylsulfonyl)-4-ethyl-4,5,6,7-tetrahydro-1H-pyrazolo[4,3-c]pyridin-6-yl)methyl dimethylcarbamate;
2-(5-(4-chlorophenylsulfonyl)-4,5,6,7-tetrahydro-2H-pyrazolo[4,3-c]pyridin-6-yl)thiazole;
2-(5-(4-chlorophenylsulfonyl)-4,5,6,7-tetrahydro-2H-pyrazolo[4,3-c]pyridin-4-yl)thiazole;
5-(4-chlorophenylsulfonyl)-4-ethyl-4,5,6,7-tetrahydro-1H-pyrazolo[4,3-c]pyridin-6-yl)methanol;
4,6-diethyl-5-(pyridin-2-ylsulfonyl)-4,5,6,7-tetrahydro-2H-pyrazolo[4,3-c]pyridine;
4,6-diethyl-5-(pyridin-2-ylsulfonyl)-4,5,6,7-tetrahydro-2H-pyrazolo[4,3-c]pyridine;
4,6-dimethyl-5-(4-(trifluoromethyl)phenylsulfonyl)-5,6-dihydro-2H-pyrazolo[4,3-c]pyridin-7(4H)-one;

and stereoisomers, tautomers, mixtures of stereoisomers and/or tautomers or pharmaceutically acceptable salts thereof.

In another aspect, the invention provides a method of treating Alzheimer's disease comprising administering a therapeutically effective amount of a compound or salt of formula I to a patient in need of such treatment.

In another aspect, the invention provides a method of treating Alzheimer's disease comprising administering a therapeutically effective amount of a compound or salt of formula Ia to a patient in need of such treatment In still another aspect, the invention provides a composition comprising a compound or salt of formula 1 and at least one pharmaceutically acceptable solvent, adjuvant, excipient, carrier, binder or disintegrant.

In still another aspect, the invention provides a composition comprising a compound or salt of formula I and at least one pharmaceutically acceptable solvent, adjuvant, excipient, carrier, binder or disintegrant.

In still another aspect, the invention provides a composition comprising a compound or salt of either formula Ia and at least one pharmaceutically acceptable solvent, adjuvant, excipient, carrier, binder or disintegrant.

In still another aspect, the invention provides a method of treating Alzheimer's disease comprising administering a therapeutically effective amount of a compound or salt of formula I to a patient in need of such treatment.

In still another aspect, the invention provides a method of treating Alzheimer's disease comprising administering a therapeutically effective amount of a compound or salt of formula Ia to a patient in need of such treatment.

In another aspect, the compounds of the invention have minimal interaction or preferably, no interaction with Notch.

Definitions

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different. It will be understood by those skilled in the art with respect to any group containing one or more substituents that such groups are not intended to introduce any substitution or substitution patterns that are sterically impractical and/or synthetically non-feasable.

APP, amyloid precursor protein, is defined as any APP polypeptide, including APP variants, mutations, and isoforms, for example, as disclosed in U.S. Pat. No. 5,766,846. A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkanoyl" is meant an acyl radical Alk-C(O)—, wherein Alk is an alkyl radical as defined herein. Examples of alkanoyl include acetyl, propionyl, butyryl, isobutyryl, valeryl, isovaleryl, 2-methyl-butyryl, 2,2-dimethylpropionyl, valeryl, hexanoyl, heptanoyl, octanoyl and the like.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons. The term also includes substituted alkyl groups, and refers to an alkyl group in which 1 or more hydrogen atoms is replaced by a substituent independently selected from the group: acyl, acyloxy, alkoxy, amino (wherein the amino group may be a cyclic amine), aryl, heteroaryl, heterocyclyl, carboxyl, oxo, amido, cyano, cycloalkyl, cycloalkenyl, halogen, hydroxyl, nitro, sulfamoyl, sulfanyl, sulfinyl, sulfonyl, and sulfonic acid.

By "alkylene" is meant a diradical alkyl group, whereby alkyl is as defined above By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like. The term also includes substituted alkenyl groups, and refers to an alkenyl group in which 1 or more hydrogen atoms is replaced by a substituent independently selected from the group: acyl, acyloxy, alkoxy, amino (wherein the amino group may be a cyclic amine), aryl, heteroaryl, heterocyclyl, carboxyl, oxo, amido, cyano, cycloalkyl, cycloalkenyl, halogen, hydroxyl, nitro, sulfamoyl, sulfanyl, sulfinyl, sulfonyl, and sulfonic acid, for example 1H-pyrrol-2-ylmethylene "Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like. The term also includes substituted alkynyl groups, and refers to an alkynyl group in which 1 or more hydrogen atoms is replaced by a substituent independently selected from the group: acyl, acyloxy, alkoxy, amino (wherein the amino group may be a cyclic amine), aryl, heteroaryl, heterocyclyl, carboxyl, oxo, amido, cyano, cycloalkyl, cycloalkenyl, halogen, hydroxyl, nitro, sulfamoyl, sulfanyl, sulfinyl, sulfonyl, and sulfonic acid. By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or substituted in one or more substitutable positions with various groups. For example, such aryl groups may be optionally substituted with, for example, $C_1$-$C_6$ alkyl, $C_1$-$C_6$ alkoxy, halogen, hydroxyl, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "arylalkyl" or "aralkyl" is meant the group-alkylene-aryl, wherein alkylene and aryl are defined herein.

By "aryloxy" is meant the group —O-aryl wherein the term aryl is as defined herein.

By "arylalkyloxy" or "aralkyloxy" is meant the group —O—$C_{1-4}$-alkylene-aryl wherein the terms aryl and alkylene are as defined herein. An example of arylakyloxy is benzyloxy (or —O—$CH_2$-phenyl).

By "cycloalkyl" is meant a saturated carbocyclic radicals having three to twelve carbon atoms. The cycloalkyl can be monocyclic, a polycyclic fused system, or a bi or polycyclic bridged system, such as adamantyl or bicyclo[2.2.1]heptyl. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or substituted in one or more substitutable positions with various groups. For example, such cycloalkyl groups may be optionally substituted with, for example, $C_1$-$C_6$ alkyl, $C_1$-$C_6$ alkoxy, halogen, hydroxyl, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino-($C_1$-$C_6$)alkyl.

By the term "halogen" or "halo" in the present invention is meant fluorine, bromine, chlorine, and/or iodine.

By "haloalkyl" is meant an alkyl radical having the meaning as defined above wherein one or more hydrogens are replaced by a halogen. Examples of such haloalkyls include chloromethyl, 1-bromoethyl, fluoromethyl, difluoromethyl, trifluoromethyl, 1,1,1-trifluoroethyl and the like.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Heteroaryl groups of the present invention include pyridyl, pyrimidyl, quinolinyl, benzothienyl, indolyl, indolinyl, pryidazinyl, pyrazinyl, isoindolyl, isoquinolyl, quinazolinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, benzothienyl, indolyl, pryidazinyl, pyrazinyl, isoindolyl, isoquinolyl, quinazolinyl, quinoxalinyl, imidazolyl, isoxazolyl, pyrazolyl, oxazolyl, thiazolyl, benzothiazolyl, benzimidazolyl, benzofuranyl, furanyl, thienyl, and pyrrolyl. More preferred heteroaryl groups include pyridyl, pyrimidyl, thienyl, pyrazolyl, oxazolyl, thiazolyl, and pyrrolyl. Still more preferred are pyridyl, pyrimidyl, thienyl, pyrrolyl and thiazolyl, The heteroaryl groups herein are unsubstituted or substituted in one or more substitutable positions with various groups. For example, such heteroaryl groups may be optionally substituted with, for example, $C_1$-$C_6$ alkyl, $C_1$-$C_6$ alkoxy, halogen, hydroxyl, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidyl, dihydrofuryl, dihydropyranyl, tetrahydrothienyl S-oxide, tetrahydrothienyl S,S-dioxide and homothiomorpholinyl S-oxide. More preferred are piperidinyl, piperazinyl, pyrrolidinyl, morpholinyl, thiomorpholinyl, thiomorpholinyl S,S-dioxide, tetrahydrofuranyl, or imidazolidinyl. The heterocycle groups herein are unsubstituted or substituted in one or more substitutable positions with various groups. For example, such heterocycle groups may be optionally substituted with, for example, $C_1$-$C_6$ alkyl, $C_1$-$C_6$ alkoxy, halogen, hydroxyl, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl, di($C_1$-$C_6$)alkylamino($C_1$-$C_6$)alkyl or =O.

By "hydroxyalkyl" is meant an alkyl substituted with a hydroxyl, such as hydroxymethyl, 1-hydroxypropyl, 2-hydroxyethyl, 3-hydroxyethyl, or 3-hydroxybutyl.

Most compounds were named using Autonom 2000 4.01.305, which is available from Beilstein Information Systems, Inc, Englewood, Colo., or ChemDraw v. 9.0.1 or 10.0, (available from Cambridgesoft at 100 Cambridge Park Drive, Cambridge, Mass. 02140). Alternatively, the names were generated based on the IUPAC rules.

The term "rel" is used to denote the relative configuration of any asymmetric center with respect to another stereocenter within the same molecule or, alternatively, to denote the relative configuration of any asymmetric center in one molecule with respect to the same stereocenter in its enantiomer when the absolute configurations have not been determined.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

The term "acid prodrug group" denotes a moiety that is converted in vivo into an active carboxylic acid compound of formula I. Such prodrug groups are generally known in the art and include ester forming groups, to form an ester prodrug, such as benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$) alkoxy optionally substituted by N-morpholino and amide-forming groups such as di($C_1$-$C_6$)alkylamino. Preferred prodrug groups include $C_1$-$C_6$ alkoxy forming an ester, and O−M+ where M+ represents a cation to form a salt of the acid. Preferred cations include sodium, potassium, and ammonium. Other cations include magnesium and calcium. Further preferred prodrug groups include $O^-M^{++}$ where $M^{++}$ is a divalent cation such as magnesium or calcium.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa buffer and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make tip the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used.

These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this document of all articles and references, including patents, are incorporated herein by reference in their entirety.

The invention is illustrated further by the following examples, which are not to be construed as limiting the invention in scope or spirit to the specific procedures described in them.

The starting materials and various intermediates may be obtained from commercial sources, prepared from commercially available compounds, and/or prepared using known synthetic methods.

General Synthetic Procedures

The compounds of the invention can be prepared using methods known in the art of organic synthesis. For example, the compounds of the invention, as well as all intermediates, can be synthesized by known processes using either solution or solid phase techniques, as shown below. Representative procedures for preparing compounds of the invention are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

Certain abbreviations used throughout the specification have the following meanings:

BiNAP refers to 2,2'-bis-diphenylphosphanyl-[1,1']binaphthalenyl.
conc. refers to concentrated.
DBU refers to 1,8-diazabicyclo[5.4.0]undec-7-ene.
DCM refers to dichloromethane.
DDC refers to dicyclohexylcarbodiimide.
DIEA refers to N,N-diisopropylamine.
DMA refers to N,N-dimethylacetamide.
DMAP refers to dimethylaminopyridine.
DMF refers to dimethyl formamide.
DMF-DMA refers to dimethyl formamide dimethylacetal.
DMSO refers to dimethylsulfoxide.
EDC refers to 1-(3-dimethylaminopropyl)-3-ethylcarbodiimide, hydrochloride.
$Et_2O$ or ether refers to diethyl ether.
EtOAc refers to ethyl acetate.
HATU refers to O-(7-Azabenzotriazol-1-yl)-N,N,N',N'-tetramethyluroniumhexafluorophosphate.
HBTU refers to 1-hydroxybenztriazolyltetramethyl-uronium.
HPLC refers to high pressure liquid chromatography.
$IC._{50}$ refers to the molar concentration of a drug, which produces 50% of the maximum possible inhibition for that drug.
LCMS refers to liquid chromatography/mass spectrometer.
MeOH refers to methanol.
MMNG refers to 1-methyl-3-nitro-1-nitrosoguanidine.
MP-TsOH refers to macroporous polystyrene backbone crosslinked (10-25%) with divinylbenzene that has been functionalized with a sulfonic acid group.
MS stands for mass spectrum.
m/z refers to mass to charge ratio.
NMR refers to nuclear magnetic resonance.
RT refers to room temperature.
sat. refers to saturated.
THF refers to tetrahydrofuran.
TMS refers to tetramethylsilane.
TMS-Cl refers to trimethylchlorosilane.

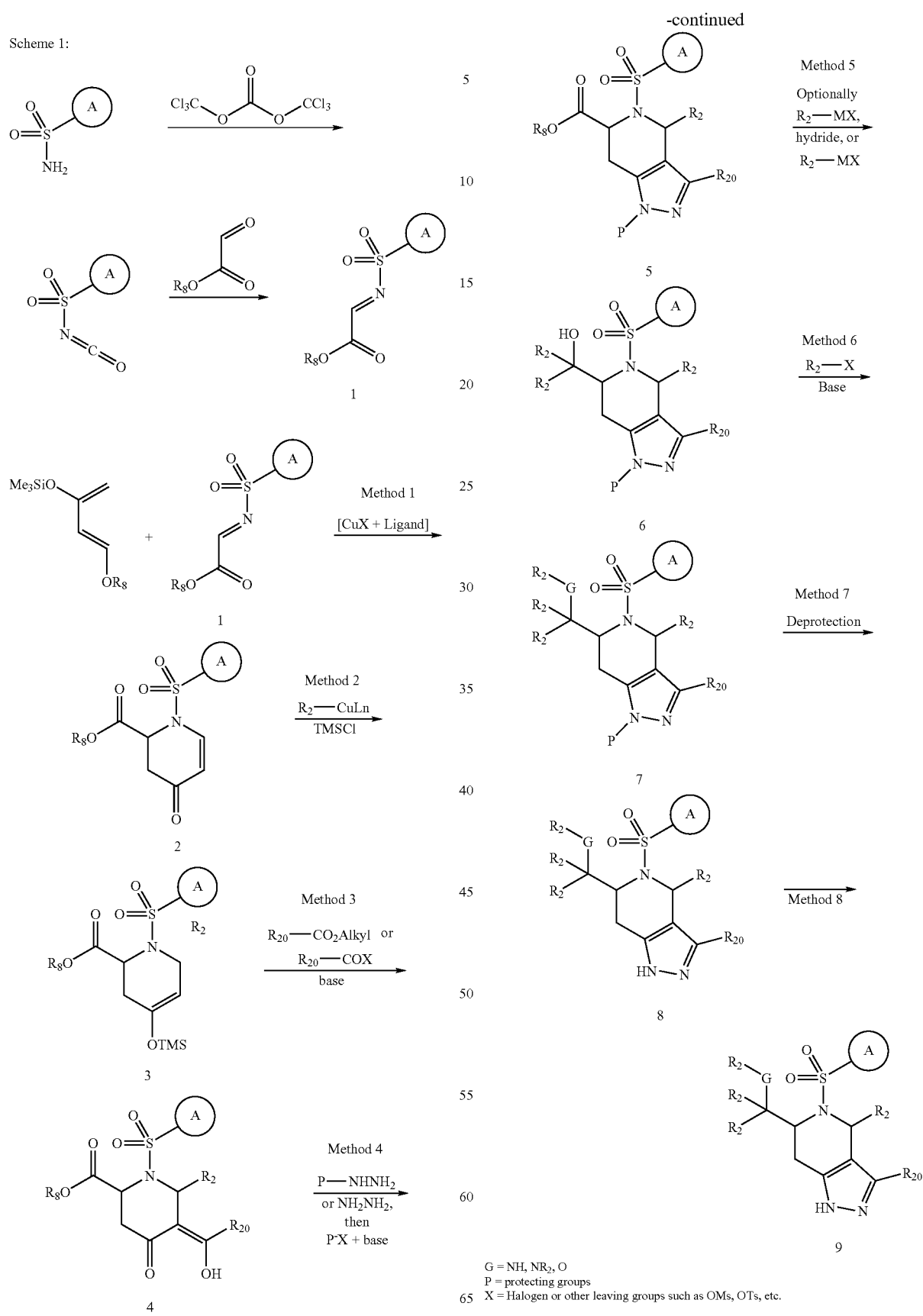

In the above scheme, each of the variables independently contains the definitions as described above, One of ordinary skill in the art will appreciate that the above scheme can be used to selectively produce a single diastereomer and/or a single enantiomer.

Method 1.

Sulfonyl glyoxaldehyde imines 1 (prepared according to Lit: *Synlett*, (1991), pp. 29-30.) was condensed with Danishefsky's diene in a refluxing solvent (e.g. 50-250° C. in toluene, xylene, etc.), or at lower temperature (−78 to 50° C.) in a solvent (tetrahydrofuran, dichloromethane, acetonitrile, etc.) with a metal catalyst and ligand (e.g. Cu(ClO4)(MeCN)4 and S-di(p-tolyl)BiNAP). The reaction can be worked up and purified according to literature to provide the ester enone sulfonamides 2.

Method 2.

Reaction of the ester enones 2 with an organocopper or organocuprate (e.g. vinyl(Me)CuCN example in Lit: *J. Am. Chem. Soc.* (2003), Vol. 68, pp. 8867-8878 or *J. Org. Chem.* (1996), Vol. 61, 4594-4599) at low temperature (−100 to 250° C.) gives the enolate which may be trapped as an enol ether using TMS-Cl or other electrophile. After quenching the reaction, the product enol ethers 3 are isolated after a typical workup.

Method 3.

The enol ethers 3 can generate the enolate by addition of methyllithium or other nucleophile in a solvent such as tetrahydrofuran. The enolate may be reacted with various electrophiles including ethyl formate, formyl pivalate, ethyl trifluoroacetate, pyruvonitrile and others to yield enol ketones 4 upon typical workup and purification.

Method 4.

The enol-ketones 4 was condensed with hydrazine or a substituted hydrazine (free hydrazine solution or salt) in a single solvent or combination of ethanol, acetic acid, tetrahydrofuran, toluene or others with our without added base such as sodium acetate. After a typical workup, the product pyrazoles 5 may be purified by chromatography or crystallization.

Method 5.

The ester group of pyrazoles 5 (or alternatively, the acid of pyrazole 5 which is formed by hydrolysis of the ester), under typical polar solvent (tetrahydrofuran, tetrahydropyran, etc.) and low temperature conditions (−100 to 250° C.) may be optionally reacted with one or more nucleophiles, sequentially either with or without intermediate workup. Nucleophiles such as lithium tri-s-butylborohydride, lithium tri-t-butoxyaluminum hydride, alkyl or aryl magnesium or lithium reagents, organocerium or organozinc reagents may react to yield the secondary or tertiary alcohol products 6 after workup and purification.

Alternatively, the acid of pyrazole 5 may be converted into a Weinreb amide and be further elaborated to generate, for example, a ketone from the acid.

Alternatively, the acid of pyrazole 5 may be reacted with some other coupling or activating reagent (such as DCC, EDC, HATU, HBTU, etc) to generate a species that can further elaborated to generate, for example, an amide from the acid.

Method 6.

The alcohol pyrazole products 6 may be alkylated at the O—H position using various electrophilic reagents such alkyl halides, benzylic halides and heterosubstituted alkyl and arylalkyl halides using a typical solvent (acetonitrile, etc.) and base (triethylamine, 4-dimethylaminopyridine, cesium carbonate, silver(I) oxide, etc.), or using activation and displacement conditions (i.e., Mitsunobu conditions with an acidic nucleophilic group like a sulfonamide, acylated amine, etc.). The alcohols 6 may also be acylated using typical conditions (acylation Lit. WO 2003/014075 or US 20050085506). After typical workup and purification by chromatography or crystallization the ether or amine substituted pyrazoles 7 may be obtained.

Method 7.

In the case of pyrazole products 7 with a protecting group on one of the pyrazole nitrogens, this group may be removed by common acidic, nucleophilic, oxidative or reductive conditions common to the protecting group to yield the free NH pyrazoles 8.

Method 8.

In the case of pyrazole products 7 or 8 without a carbon substituent ($R_{20}$=H), this C—H position may be halogenated by reagents such as N-chlorosuccinimide, bromine, etc. (bromination Lit. WO 2003/066634). After typical workup and purification by chromatography or crystallization the halogenated pyrazoles 9 may be further substituted at this position by nucleophiles or palladium mediated couplings.

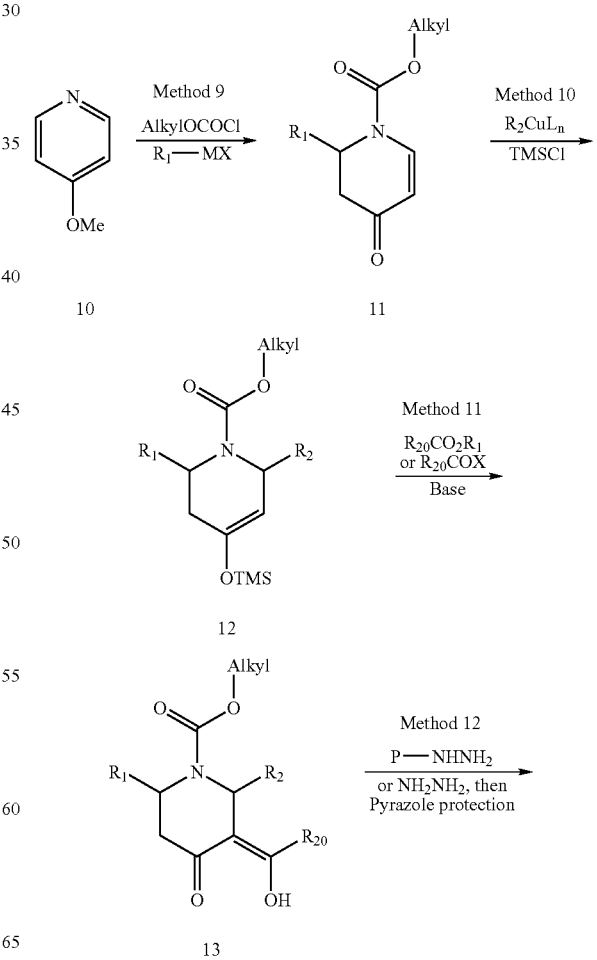

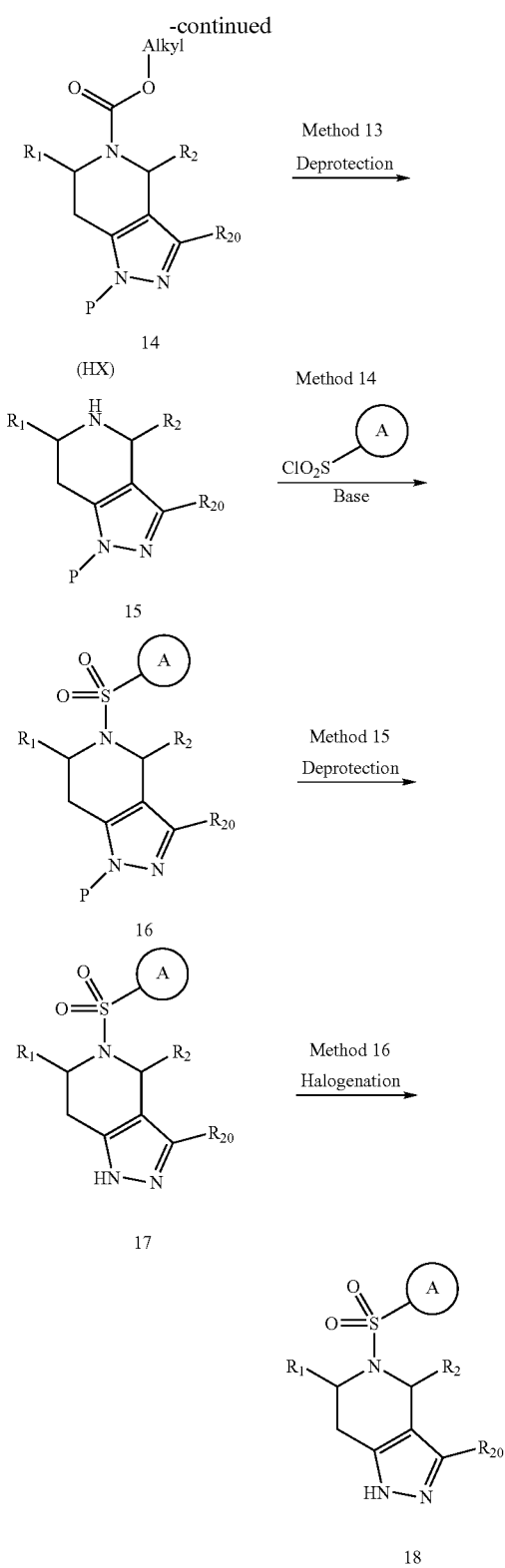

In the above scheme, each of the variables independently contains the definitions as described above, while alk is a $C_1$-$C_6$ alkyl group. One of ordinary skill in the art will appreciate that the above scheme can be used to selectively produce a single diastereomer and/or a single enantiomer.

Method 9.

4-Methoxypyridine 10 may be reacted according to Lit. (*Tetrahedron Lett.*, (1986), Vol. 27 (38), pp. 4549-4552 or *J. Am. Chem. Soc.* (2003), Vol. 68, pp. 8867-8878.) with a organomagnesium reagent and a chloroformate (e.g. benzylchloroformate or phenyl chloroformate) at lower temperature (−78 to 50° C.) in a solvent (tetrahydrofuran, dichloromethane, acetonitrile, etc.). The reaction can be worked up and purified according to Lit, to provide the enone carbamate 11.

Method 10.

Reaction of the enone carbamate 11 according to Method 2 provides the product enol ether carbamate 12.

Method 11.

The enol ether 12 can generate the enolate by addition of methyllithium or other nucleophile as in Method 3 and reacted to generate the enol ketone 13. Alternatively the enol ether 12 may be reacted with various electrophiles (e.g. dichloromethyl methyl ether, trimethylorthoformate, etc.) and a Lewis acid (tin chloride, titanium chloride, etc.) to yield an enol-ketone 13 upon typical workup and purification.

Method 12.

The enol-ketone 13 may be treated as in Method 4 to yield the pyrazole carbamate 14 which may be purified by chromatography or crystallization.

Method 13.

The pyrazole carbamate 14 may be deprotected by standard means as appropriate for the protection utilized (treatment with trimethylsilyl iodide, catalytic hydrogenation, sodium alkoxide, etc.) as described in Greene, Theodora W.; Wuts, Peter G. M. *Protective Groups in Organic Synthesis.* 2nd Ed. (1991), p. 473. After typical workup and optional purification by chromatography or crystallization, the pyrazole piperidine 15 may be obtained as the free amine or as a salt form.

Method 14.

The pyrazole piperidine 15 may be sulfonylated with a sulfonyl chloride and organic or inorganic base (e.g. triethylamine, pyridine, aqueous sodium hydroxide, etc.) with or without a solvent such as dichloromethane or tetrahydrofuran at temperatures from 0 to 25° C. After typical workup and optional purification by chromatography or crystallization, the pyrazole sulfonamide 16 may be obtained.

Method 15.

In the case of pyrazole products 16 with a protecting group on one of the pyrazole nitrogens, this group may be removed by common acidic, nucleophilic, oxidative or reductive conditions common to the protecting group to yield the free NH pyrazole 17.

Method 16.

In the case of pyrazole products 17 without a carbon substituent ($R_{20}$=H), this C—H position may be halogenated by reagents such as N-chlorosuccinimide, bromine, etc. (bromination Lit. WO 2003/066634.) After typical workup and purification by chromatography or crystallization the halogenated pyrazole 18 may be further substituted at this position by nucleophiles or palladium mediated couplings.

Scheme 3:

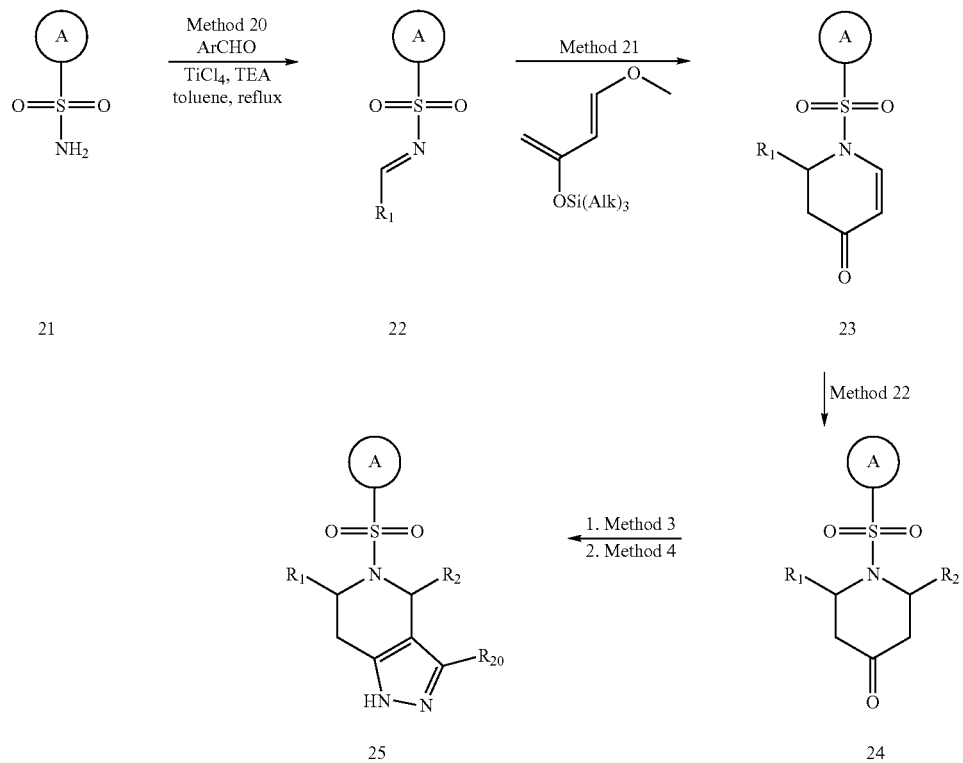

In the above scheme, each of the variables independently contains the definitions as described above, while each alk is independently $C_1$-$C_6$ alkyl (preferably, methyl, ethyl, isopropyl, or tert-butyl). One of ordinary skill in the art will appreciate that the above scheme can be used to selectively produce a single diastereomer and/or a single enantiomer.

Method 20.

Aryl imines 22 are prepared by refluxing 21 with a suitable aryl aldehyde and a Lewis acid such as $TiCl_4$ in a suitable solvent such as toluene, benzene, etc. according to the procedure: W. Brian Jennings, et Al., *Tetrahedron* (1991), Vol 47, No. 29, pp. 5561-5568.

Method 21.

Compounds 23 are prepared from compounds 22 by the Diels Alder reaction according to the literature procedure: Geoffrey R. Heintzelman, et al., *J. Org. Chem.*, (1996), Vol. 61, pp. 4594-4599.

Method 22.

Compounds 24 are prepared from Compounds 23 by hydrogenation with $H_2$ and a suitable catalyst such as Pd on Carbon in a suitable solvent such as methanol or ethanol etc. Compounds 24 can also be prepared using L-selectride by the procedure: Williams, Alfred L.; Abad Grillo, Teresa; Comins, Daniel L. Department of Chemistry, North Carolina State University, Raleigh, N.C., USA. *Journal of Organic Chemistry* (2002), No. 67 (6), pp. 1972-1973. Alternatively, Compounds 24 can be prepared according to Method 2 above, or Method 32 as outlined below.

Compounds 25 can be prepared by subjecting Compounds 24 to Method 3 and Method 4 as outlined above.

Scheme 4:

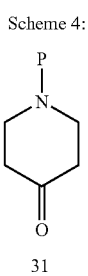

31

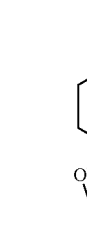

32

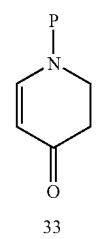

33

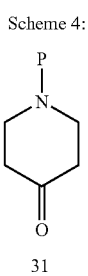

34

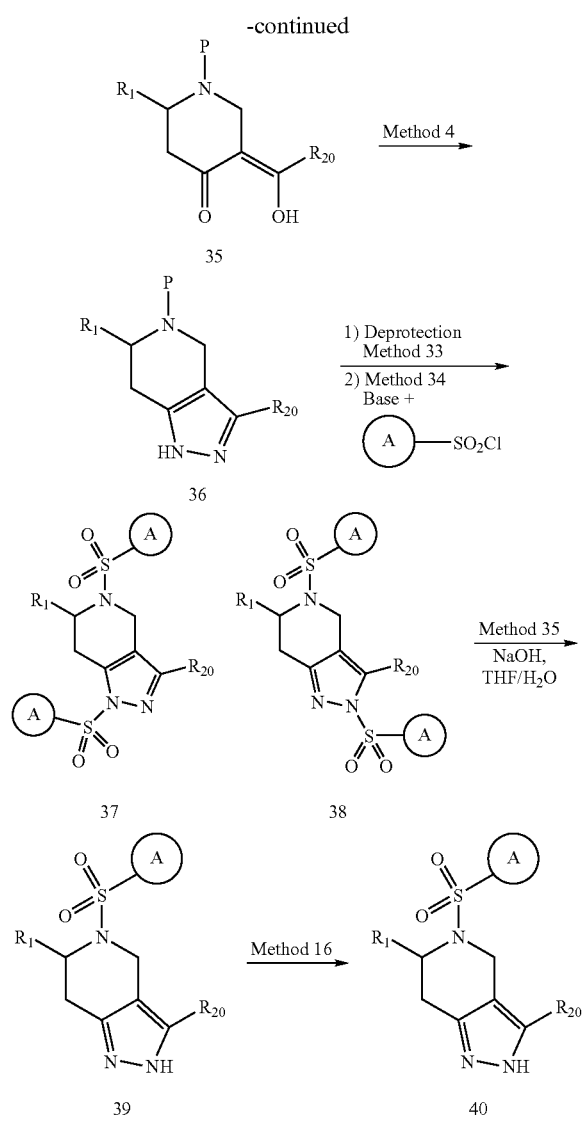

In the above scheme, each of the variables independently contains the definitions as described above, while P is a protecting group. One of ordinary skill in the art will appreciate that the above scheme can be used to selectively produce a single diastereomer and/or a single enantiomer.

Method 30.

Benzyl 4-oxo-1-piperidinecarboxylate 31 (purchased from Aldrich, St. Louis, Mo.) was treated with bromine in ethylene glycol to yield compound 32.

Method 31.

Elimination of compounds 32 with a base such as DBU, DIEA, etc. in a suitable solvent such as DMSO DMF, DMA, etc. followed by hydrolysis gives compounds 33.

Method 32.

1,4-addition of aryl Grignard reagents to 33 with an in-situ formed $BF_3$ $OEt_2$/organo copper complex led to compounds 34. Alternatively, Compounds 34 can be prepared according to method 2 above. Alternatively, compounds 34 can be prepared asymmetrically by the rhodium catalyzed 1-4 addition of organozinc reagents to compounds 33 as described by Hayashi JACS. (2004), Vol. 125, pp. 6240-41. Alternatively, compounds 34 can be prepared asymmetrically by the rhodium/phosphoramidite catalyzed conjugate addition of arylboronic acids to compounds 33 as described by de Vries, Feringa, and Minnaard. Org. Lett. (2005), Vol. 7, pp. 2433-35.

Compounds 36 are prepared by formylation or acylation of ketones 34 using method 3 and method 4.

Method 33.

Compounds 36 may be deprotected by standard means appropriate to the type of protection utilized as described in Greene, Theodora W.; Wuts, Peter G. M. Protective Groups in Organic Synthesis. 2nd Ed. (1991), 473 pp. (treatment with trimethylsilyl iodide, catalytic hydrogenation, sodium alkoxide, etc.)

Method 34.

Sulfonylation is performed with a sulfonyl chloride and organic or inorganic base (e.g. triethylamine, pyridine, aqueous sodium hydroxide, DIEA, etc.) with or without a solvent such as dichloromethane or tetrahydrofuran at temperatures from 0 to 25° C. After typical workup and optional purification by chromatography or crystallization, the di-sulfonylated products 37, and 38 are obtained.

Method 35.

The di-sulfonylated products 37, and 38 were selectively cleaved hydrolytically with a base such as NaOH, NaOMe, etc. in a suitable solvent such as THF, MeOH, Dioxane, $H_2O$, etc. to afford the products 39.

EXPERIMENTAL PROCEDURES

Certain compounds of this invention are prepared from other compounds of this invention via-known reactions and functional group transformations. Examples of such transformations are ester hydrolysis, amide formation, and reductive alkylation; with examples of these are described in the preparations below. Starting materials are obtained from commercial sources or prepared by known methods as described in the examples below.

Compounds included in this invention are exemplified by the following examples, which should not be construed as limiting the scope of this disclosure. Analogous structures and alternative synthetic routes within the scope of the invention will be apparent to those skilled in the art.

Reagents and solvents obtained from commercial suppliers were used without further purification unless otherwise stated. Thin layer chromatography was performed on pre-coated 0.25 mm silica gel plates (E. Merck, silica gel 60, F254). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. 1H NMR spectra were recorded on either a Varian Gemini 300 MHz spectrometer or a Bruker Avance 300 MHz spectrometer. Chemical shifts are reported in ppm (δ) and were calibrated using the undeuterated solvent resonance as internal standard. Mass spectra were recorded on an Agilent series 1100 mass spectrometer connected to an Agilent series 1100 HPLC.

Purity of compounds were determined by HPLC/MS analysis by a variety of analytical methods:

[1]=20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[2]: An isocratic gradient employing 10-20% EtOH or isopropanol in hexane on a Chiralcel OD or Chiralcel OJ 2 cm×25 cm column, 220 nm detection at rt.

EXAMPLE 1

Preparation of 5-(4-chlorophenylsulfonyl)-6-phenyl-4,5,6,7-tetrahydro-2H-pyrazolo[4,3-c]pyridine (55)

of the piperidin-4-one (50) (442 mg, 1.61 mmol) and 75 mg of NaH (60% suspension in mineral oil, 1.77 mmol) in 10 ml of benzene were added 1.3 ml of ethyl formate and 40 µl of methanol. The mixture was stirred at room temperature overnight. Water (5 ml) was added and the organic layer was separated. NaHSO$_4$ (10% Aq) was added to the aqueous layer to adjust pH to the range of 3-4 and then extracted with EtOAc twice (2×10 ml). Combined organic layers were washed with brine (5 ml) once, and dried (MgSO$_4$). After evaporation of

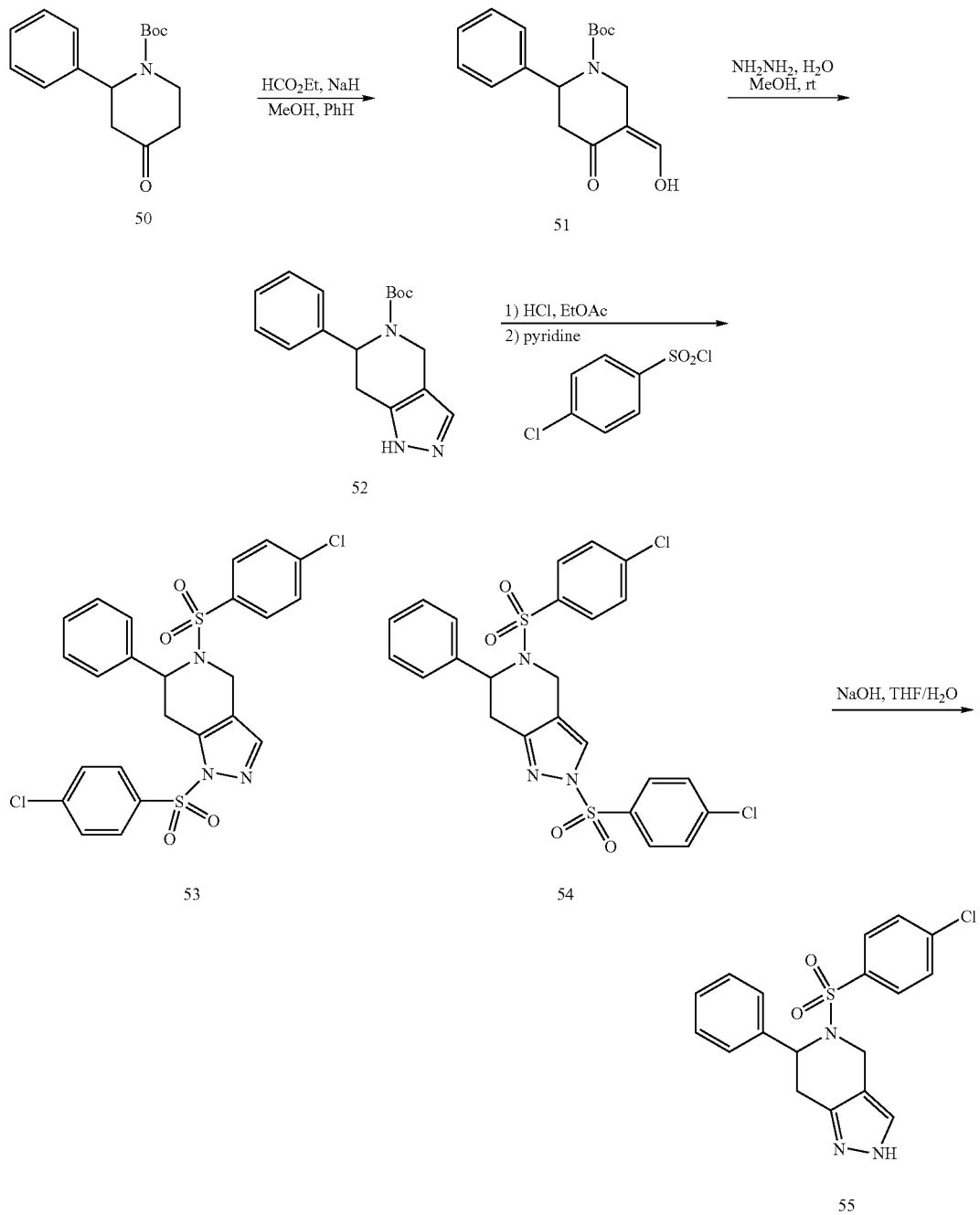

Synthesis of 5-hydroxymethylene-4-oxo-2-phenyl-piperidine-1-carboxylic acid tert-butyl ester (51). To a suspension solvent, the yellow oil was used for the next reaction without further purification LCMS 326.1 (M+23)

Synthesis of 6-phenyl-1,4,6,7-tetrahydro-pyrazolo[4,3-c]pyridine-5-carboxylic acid tert-butyl ester (52). Compound 51 (310 mg, 1.02 mmol) from the previous step was dissolved in MeOH (3 ml). Hydrazine monohydrate (0.1 ml, 2.04 mmol) was added to the solution and then stirred at room temperature for 1 hour. Solvent was removed under reduced pressure to afford a yellow gel as the desired product. LCMS 300.2 (M+1)

Synthesis of 1,5-bis-(4-chloro-benzenesulfonyl)-6-phenyl-4,5,6,7-tetrahydro-1H-pyrazolo[4,3-c]pyridine (53) and its regioisomer (54). Compound 52 from the previous step (1.1 g, 3.67 mmol) was dissolved in ethyl acetate (15 ml). HCl (g) was bubbled into the solution for 5 minutes. Solvent was removed under reduced pressure and the residue was re-dissolved in pyridine (15 ml). 4-chlorophenylsulfonyl chloride (1.55 g, 2.2 eq.) was added to the solution at zero degrees. The mixture was stirred at zero degrees and slowly raised to room temperature upon stirring overnight. Ethyl acetate (100 ml) was added to the reaction mixture, and the solution was washed with sat. NaHCO$_3$ (2×25 ml), 10% HCl solution (2×25 ml) and brine (10 ml). Sample dried over (MgSO$_4$), and solvent was removed under reduced pressure. The crude product was purified via flash chromatography, eluted with EtOAc/hexane (15:85) to give a white solid as the mixture of two regioisomers. LCMS 569.9 (M+23)

Synthesis of 5-(4-chloro-benzenesulfonyl)-6-phenyl-4,5,6,7-tetrahydro-2H-pyrazolo[4,3-c]pyridine (55). Regioisomers 53 and 54 from the previous step (197 mg, 0.36 mmol) were dissolved in a mixture of THF and water (2:1, 4.5 ml). NaOH (1.1 ml, 1.0 M) was added to the solution and the mixture was stirred at 75° C. for 3 hours. After cooling to room temperature, ethyl acetate (50 ml) was added and mixture was washed with brine twice. Solvent was removed under reduced pressure to give an off-white solid as the pure product. LCMS 374.0 (M+1)

$^1$H NMR (CDCl$_3$) δ 7.72 (d, J=7.5 Hz, 2H), 7.38 (d, J=7.5 Hz, 2H), 7.29-7.19 (m, 6H), 5.61 (d, J=6.9 Hz, 1H), 4.77(d, J=16.2 Hz, 1H), 3.84 (d, J=16.2 Hz, 1H), 3.24 (d, J=16.8 Hz, 1H), 2.92 (dd, J=16.8, 6.9 Hz, 1H).

The isomers were separated into chiral isomers using HPLC Method [2]

Enantiomer A: $^1$H NMR (CDCl$_3$) δ 7.72 (d, J=7.5 Hz, 2H), 7.38 (d, J=7.5 Hz, 2H), 7.29-7.19 (m, 6H), 5.61 (d, J=6.9 Hz, 1H), 4.77(d, J=16.2 Hz, 1H), 3.84 (d, J=16.2 Hz, 1H), 3.24 (d, J=16.8 Hz, 1H), 2.92 (dd, J=16.8, 6.9 Hz, 1H). Enantiomer B: $^1$H NMR (CDCl$_3$) δ 7.72 (d, J=7.5 Hz, 2H), 7.38 (d, J=7.5 Hz, 2H), 7.29-7.19 (m, 6H), 5.61 (d, J=6.9 Hz, 1H), 4.77(d, J=16.2 Hz, 1H), 3.84 (d, J=16.2 Hz, 1H), 3.24 (d, J=16.8 Hz, 1H), 2.92 (dd, J=16.8, 6.9 Hz, 1H).

EXAMPLE 2

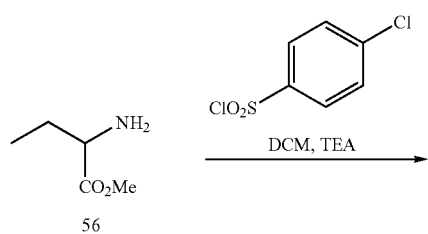

56

-continued

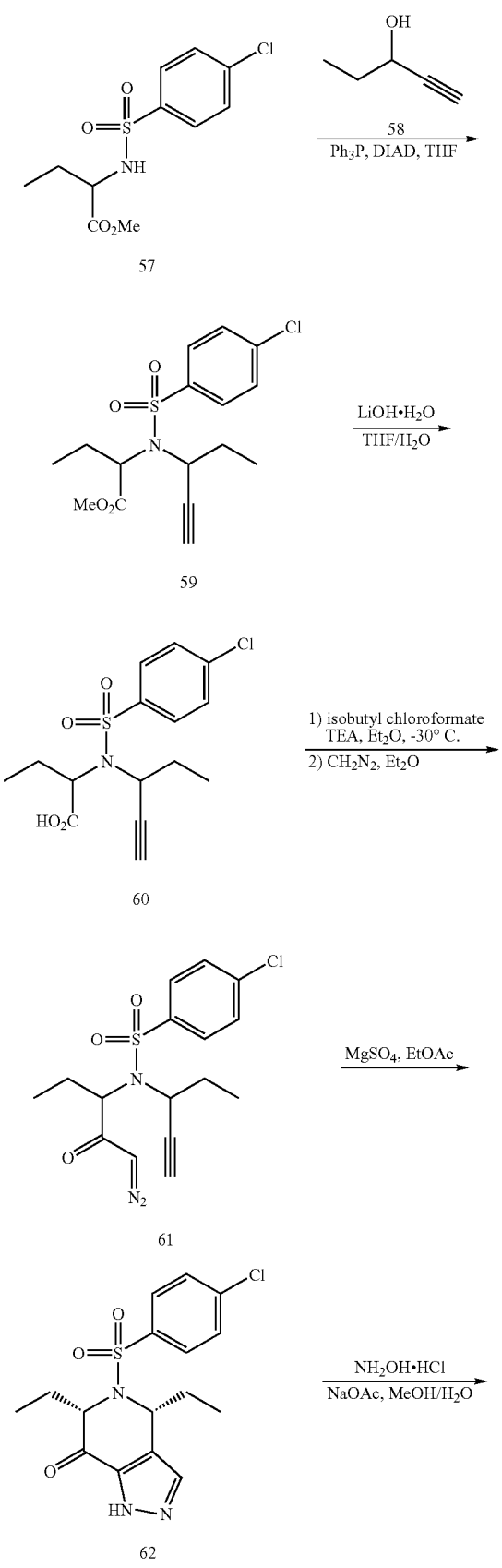

-continued

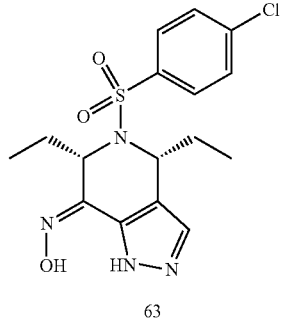

63

Synthesis of methyl 2-(4-chlorophenylsulfonamido)butanoate (57). Methyl 2-aminobutanoate hydrochloride 56 (25 g, 0.163 mol) was suspended in $CH_2Cl_2$ (100 mL) and triethylamine (50 mL) and 4-chlorobenzenesulfonyl chloride (37.8 g, 1.1 eq) were added to the mixture. The mixture was stirred at room temperature overnight. Diluted with 200 mL of $CH_2Cl_2$ and washed with water (3×50 mL), sat. $NaHCO_3$ (2×50 mL), brine (50 mL) and dried ($MgSO_4$). The solvent was removed by rotary evaporation to give the product 57 as a yellow oil. LCMS 292.0 (M+H).

Synthesis of methyl 2-(4-chloro-N-(pent-1-yn-3-yl)phenylsulfonamido)butanoate (59). To a cooled, dry flask was added compound 57 (5.0 g, 17.14 mmol), triphenylphosphine (4.25 g, 16.34 mmol) and THF (50 mL). The flask was cooled to 0° C. and 1-pentyl-3-ol 58 (1.35 mL, 15.59 mmol) in THF (50 mL) was added to the above solution. Diisopropylazodicarboxylate (3.2 mL, 16.24 mmol) was then added and the reaction mixture was warmed up to room temperature and stirred over a weekend, The solvent was removed by rotary evaporation and the residue was redissolved in EtOAc, washed with water, sat. $NaHCO_3$, brine and dried ($MgSO_4$). After concentration in vacuo, the crude material was purified by flash chromatography to give the product 59 as a white solid. LCMS 380.0 (M+23).

Synthesis of 2-(4-chloro-N-(pent-1-yn-3-yl)phenylsulfonamido)-butanoic acid (60). The compound 59 (584 mg, 163 mmol) was dissolved in THF (10 mL). Lithium hydroxide monohydrate (134 mg, 2.0 eq) was added followed by 10 mL of water. The mixture was stirred at room temperature overnight. The solvent was removed and the solution was adjusted to pH 3-4 using 3N HCl, The mixture was then extracted with EtOAc (4×20 mL). The combined organic layers were washed with brine and dried ($MgSO_4$). After removal of the solvent a white solid was obtained as the product 60. LCMS 366.0 (M+23).

Synthesis of 4-chloro-N-(1-diazo-2-oxopentan-3-yl)-N-(pent-1-yn-3-yl)benzenesulfonamide (61). To a solution of the compound 60 (498 mg, 1.45 mmol) in 7.5 mL of $Et_2O$ were added sequentially 0.24 mL of triethylamine (1.2 eq), 0.23 mL of isobutyl chloroformate (1.2 eq) at −30° C. After being stirred at −30° C. for 15 min, diazomethane (prepared by mixing MNNG and KOH in diethyl ether) (excess) was added to the above mixture at 0° C. and stirred there for 5 hours. Glacial HOAc (1.5 mL) was added to destroy the excess diazomethane and the solution was extracted with EtOAc. The organic phase was washed with sat $NaHCO_3$, water, brine and dried ($MgSO_4$). LCMS 368.1 (M+1).

Synthesis of (4R,6S)-5-(4-chlorophenylsulfonyl)-4,6-diethyl-5,6-dihydro-1H-pyrazolo[4,3-c]pyridin-7(4H)-one (62). The above solution of 61 was stirred at room temperature for four days. The cis isomer underwent 2+3 cycloaddition to give the desired product, which was separated from the trans uncyclized product by flash chromatography.

$^1$H NMR ($CDCl_3$) δ 7.58 (d, J=7.5 Hz, 2H), 7.54 (s, 1H), 7.25 (d, J=8.2 Hz, 2H), 5.09 (t, J=7.5 Hz, 1H), 4.50 (dd, J=6.6, 9.9 Hz, 1H), 2.11-1.75 (m, 4H), 1.27-1.15 (m, 6H); MS (m/z) 368.1 (M+H)$^+$.

Synthesis of (4R,6S,Z)-5-(4-chlorophenylsulfonyl)-4,6-diethyl-5,6-dihydro-1H-pyrazolo[4,3-c]pyridin-7(4H)-one oxime (63). To a solution of compound 62 (67 mg, 0.17 mmol) in a mixture of $MeOH/H_2O$ (5:1, 9 mL) was added NaOAc (141 mg, 1.7 mmol) followed by hydroxylamine hydrochloride (131.6 mg, 1.9 mmol). The resulting solution was stirred at room temperature for a weekend. The solvent was removed by rotary evaporation and the residue was taken up in EtOAc. The organic phase was washed with water, brine and dried ($MgSO_4$). After removal of the solvent under reduced pressure, the crude product was purified by flash chromatography to give a white solid as the product 63 $^1$H NMR ($CDCl_3$) δ 10.28 (bs, 1H), 7.56 (d, J=9.0 Hz, 2H), 7.45 (s, 1H), 7.20 (d, J=9.0 Hz, 2H), 5.48 (dd, J=4.5, 10.5 Hz, 1H), 4.97 (t, J=7.5 Hz, 1H), 2.06-1.96 (m, 1H), 1.91-1.77 (m, 2H), 1.68-1.57 (m, 1H), 1.22 (t, J=6.9 Hz, 3H), 114 (t, J=7.2 Hz, 3H); MS (m/z) 383.0 (M+H)$^+$.

EXAMPLE 3

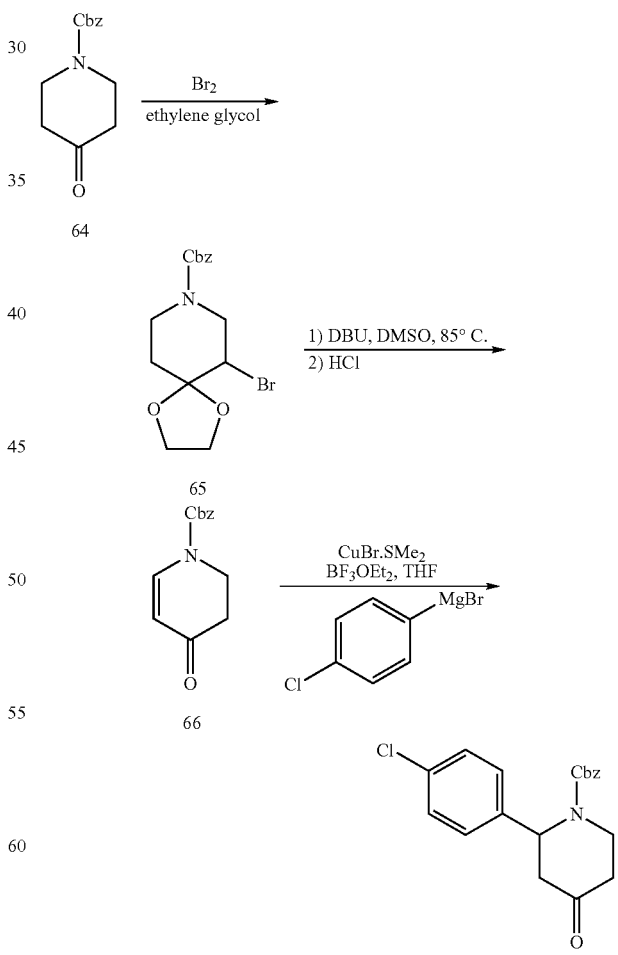

Synthesis of benzyl 6-bromo-1,4-dioxa-8-azaspiro[4.5]decane-8-carboxylate (65). A stirred solution of compound 64 (5.0 g, 21.43 mmol) in 40 mL of dry ethylene glycol was treated with bromine (27 mL, 52 mmol) in small portion over 3 hours at 35-40° C. under a nitrogen filled balloon. Bromine was added at a rate that was sufficient to maintain a red-orange color. The resulting mixture was stirred for an additional 2 hours. Anhydrous potassium carbonate (4.15 g, 21.43 mmol) was added to the reaction mixture, and stirring was continued until bubbling ceased. The mixture was diluted with water (40 mL) and extracted with diethyl ether (5×100 mL). The combined organic layers were dried over MgSO$_4$, filtered and concentrated by rotary evaporation. Chromatography of the residue on silica gel with 20% EtOAc/hexanes gave the desired product 65.

Synthesis of benzyl 4-oxo-3,4-dihydropyridine-1(2H)-carboxylate (66). The compound 65 from the previous step (2.1 g, 5.8 mmol) was dissolved in DMSO (30 mL). Under a nitrogen atmosphere, DBU (0.98 mL, 1.14 eq.) was added and the mixture was heated at 80° C. for overnight. Water was added and the mixture was extracted with diethyl ether (5×60 mL). The combined organic layers were washed with brine and dried (MgSO$_4$). The solvent was removed by rotary evaporation and the white oil was purified by flash chromatography to give the product 67 as a white oil.

Synthesis of benzyl 2-(4-chlorophenyl)-4-oxopiperidine-1-carboxylate (67). CuBr.SMe$_2$ complex (1.49 g, 7.26 mmol) was added to 25 mL of anhydrous THF and cooled to −78° C. 4-Chlorophenylmagnesium bromide (7.26 mL, 1.0 M in THF, 7.26 mmol) was added slowly via syringe. Stirring at −78° C. for 1 hour produced an orange then green-like suspension. Boron trifluoride dimethyl etherate (0.92 mL, 7.26 mmol) was added and stirred for 5 minutes. To the newly formed complex was then added over 1 hour a solution of the compound 66 (1.0 g, 4.32 mmol) in 15 mL of anhydrous THF. After stirring 2 hours at −78° C., 16 mL of aq. 20% NH$_4$Cl/conc. NH$_4$OH (1:1) was added, and the mixture was allowed to warm-up to room temperature. EtOAc was used to extract (3×100 mL) and the combined organic layers were washed with brine and dried (MgSO$_4$). Solvent was removed by rotary evaporation and the residue was purified by flash chromatography to give the product 67 as a colorless oil.

EXAMPLE 4

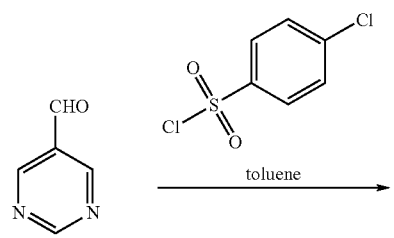

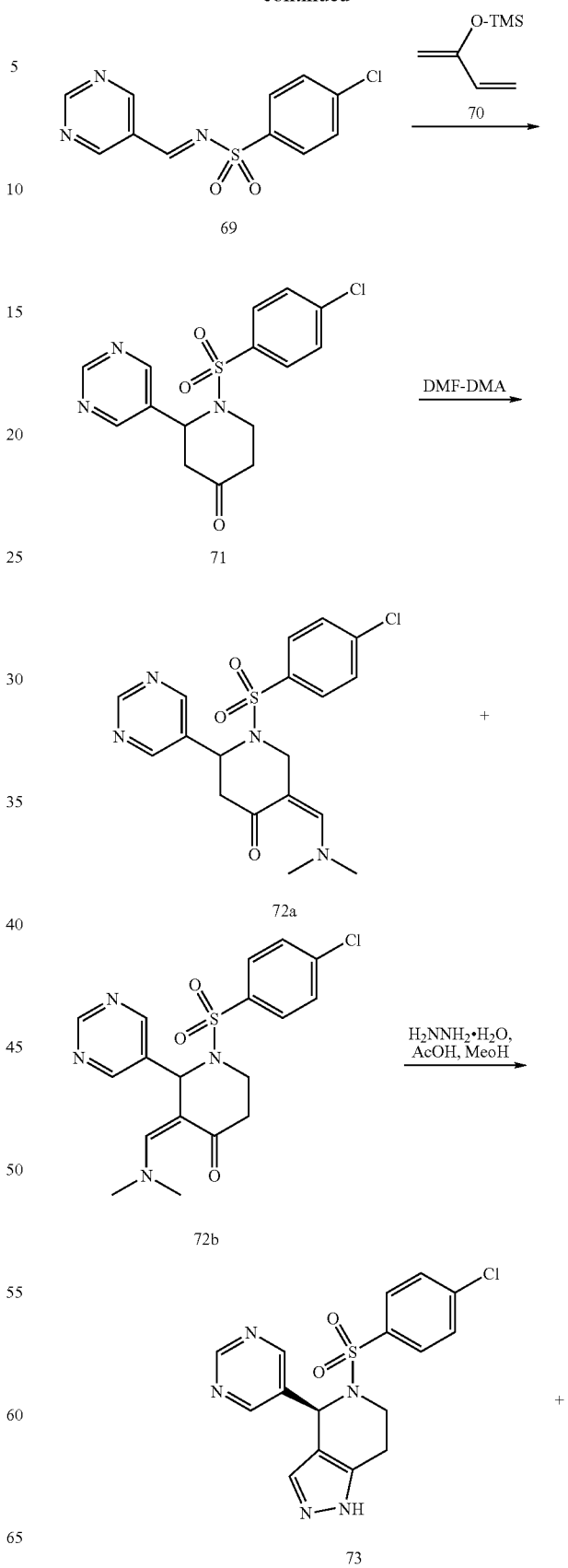

-continued

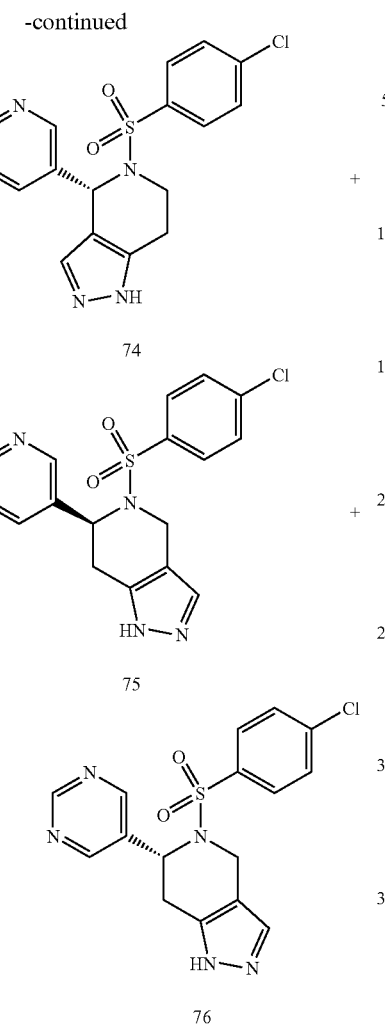

74

75

76

Synthesis of (E)-4-chloro-N-(pyrimidin-5-ylmethylene)benzenesulfonamide (69). To a solution of 5-formyl pyrimidine (68, 1.0 g, 9.3 mmol) and 4-chlorobenzene sulfonamide (1.95 g, 10.2 mmol) in toluene (20 mL) was added 4 Å molecular sieves (1.0 g) and MP-TsOH (1.0 g). Dean-stark apparatus with reflux condenser was affixed to reaction vessel and reaction was heated at reflux for 18 hours. The reaction mixture was cooled to room temperature and concentrated in vacuo. The residue was taken up in EtOAc and filtered through Celite. The filtrate was concentrated in vacuo to yield 2.12 g (81%) 69 as a light brown solid, $^1$H NMR (CDCl$_3$) δ 9.42 (s, 1H), 9.25 (s, 2H), 9.15 (s, 1H), 7.98 (d, 2H), 7.57 (d, 2H).

Synthesis of 1-(4-chlorophenylsulfonyl)-2-(pyrimidin-5-yl)piperidin-4-one (71). To a solution of 69 (2.12 g, 7.5 mmol) in THF (15 mL) was added 2-(trimethylsilyl)-1,3-butadiene (70, 2.18 g, 15 mmol). The reaction was heated at reflux for 36 hours. The reaction mixture was cooled to room temperature and concentrated in vacuo to yield 3.33 g crude material. The residue was purified by flash chromatography (3:1 hexanes/EtOAc) to yield 1.05 g (40%) 71 as a yellow solid. $^1$H NMR (CDCl$_3$) δ 9.16 (s, 1H), 8.63 (s, 2H), 7.85 (d, 2H), 7.55 (d, 2H), 5.65 (d, 1H), 4.11-4.04 (m, 1H), 3.24-3.14 (m, 1H), 2.96-2.82 (m, 2H), 2.55-2.49 (m, 1H), 2.40-2.34 (m, 1H).

Synthesis of 1-(4-chlorophenylsulfonyl)-5-((dimethylamino)methylene)-2-(pyrimidin-5-yl)piperidin-4-one and 1-(4-chlorophenylsulfonyl)-3-((dimethylamino)methylene)-2-(pyrimidin-5-yl)piperidin-4-one (72a, 72b). The compound 71 (0.20 g, 0.57 mmol) was dissolved in DMF-DMA (1 mL) and heated at 70° C. for 4 hours. The reaction mixture was concentrated in vacuo to yield 230 mg (99%) 72 as a yellow oil that was used without further purification. MS (m/z) 407. (M+H)$^+$.

Synthesis of (rel S)-5-(4-chlorophenylsulfonyl)-4-(pyrimidin-5-yl)-4,5,6,7-tetrahydro-1H-pyrazolo[4,3-c]pyridine, (rel R)-5-(4-chlorophenylsulfonyl)-4-(pyrimidin-5-yl)-4,5,6,7-tetrahydro-1H-pyrazolo[4,3-c]pyridine, (rel S)-5-(4-chlorophenylsulfonyl)-6-(pyrimidin-5-yl)-4,5,6,7-tetrahydro-1H-pyrazolo[4,3-c]pyridine and (rel R)-5-(4-chlorophenylsulfonyl)-6-(pyrimidin-5-yl)-4,5,6,7-tetrahydro-1H-pyrazolo[4,3-c]pyridine (73, 74, 75, 76). A flask was charged with compound 72 (230 mg, 0.55 mmol) and dissolved in acetic acid (2 mL) and methanol (1 mL). Hydrazine hydrate (0.083 mL, 1.7 mmol) was added and the reaction was stirred at room temperature for 18 hours. The reaction mixture was concentrated in vacuo and the residue was taken up in EtOAc. The organic layer was washed with sat. NaHCO$_3$, brine, dried over Na$_2$SO$_4$, filtered, and concentrated in vacuo to yield 0.17 g crude material as a mixture of regioisomers. The residue was purified by chromatography using Method [2] to yield four separate compounds.

5-(4-Chlorophenylsulfonyl)-4-(pyrimidin-5-yl)-4,5,6,7-tetrahydro-1H-pyrazolo[4,3-c]pyridine (Enantiomers A and B)

$^1$H NMR (CD$_3$OD) δ 9.09 (s, 1H), 8.71 (s, 2H), 7.83 (d, J=8.7 Hz, 2H), 7.47 (d, J=8.7 Hz, 2H), 6.49 (s, 1H), 4.16 (dd, J=14.9, 6.1 Hz, 1H) 3.24-3.16 (m, 1H), 2.62 (dd, J=16.4, 4.4 Hz, 1H), 2.50-2.40 (m, 1H); MS (m/z) 376.0 (M+H)$^+$.

5-(4-Chlorophenylsulfonyl)-6-(pyrimidin-5-yl)-4,5,6,7-tetrahydro-1H-pyrazolo[4,3-c]pyridine (Enantiomers A and B)

$^1$H NMR (CD$_3$OD) δ 9.03 (s, 1H), 8.59 (d, J=4.5 Hz, 2H), 7.88 (d, J=8.7 Hz, 2H), 7.54 (d, J=35=8.4 Hz, 2H), 7.43 (bs, 1H), 5.78 (d, J=6.0 Hz, 1H), 3.96-3.91 (m, 1H), 2.93 (dd, J=16.8, 6.3 Hz, 1H); MS (m/z) 376.0 (M+H)$^+$.

EXAMPLE 5

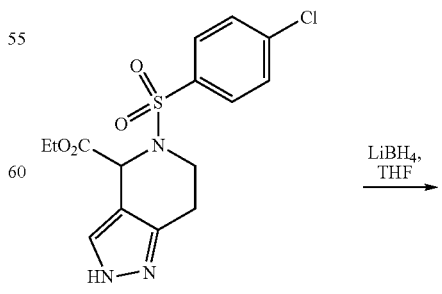

77

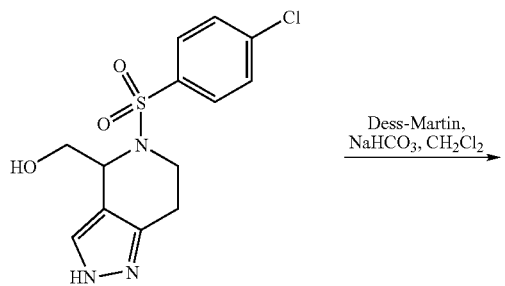

78

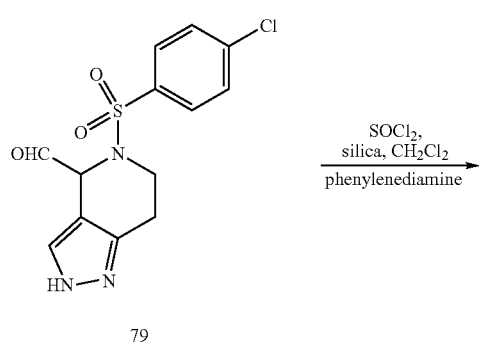

79

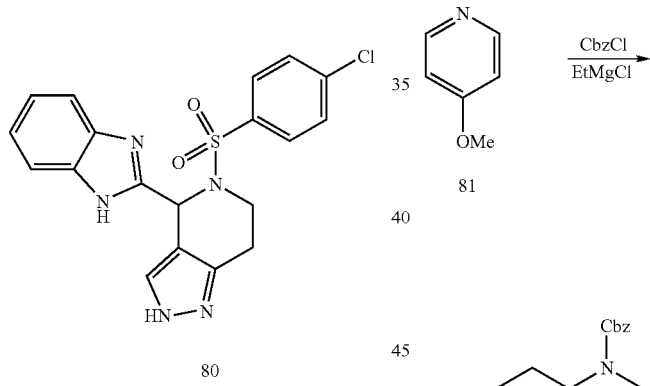

80

Synthesis of (5-(4-chlorophenylsulfonyl)-4,5,6,7-tetrahydro-2H-pyrazolo[4,3-c]pyridin-4-yl)methanol (78). Compound 77 (1.22 g, 3.3 mmol) was dissolved in THF (25 mL). Lithium borohydride (5.3 mmol) was added slowly and the reaction stirred at room temperature for 18 hours. The reaction was quenched with water (25 mL) and Rochelle's salt (2.0 g). The mixture was stirred at room temperature for 1 hour. The mixture was extracted with EtOAc and the combined organic layers were washed with brine. The organic layer was dried over $Na_2SO_4$, filtered, and concentrated in vacuo to yield 0.9 g of 78 as a white foam (83%). $^1$H NMR ($CD_3OD$) δ 7.81 (m, 2H), 7.46 (m, 3H), 5.09-5.07 (m, 1H), 4.11-4.06 (m, 2H), 3.72-3.63 (m, 2H), 3.52-3.25 (m, 1H), 2.50-2.37 (m, 2H); MS (m/z) 328, (M+H)$^+$.

Synthesis of 5-(4-chlorophenylsulfonyl)-4,5,6,7-tetrahydro-2H-pyrazolo[4,3-c]pyridine-4-carbaldehyde (79). Compound 78 (0.50 g, 1.5 mmol) was dissolved in $CH_2Cl_2$ (5 mL). $NaHCO_3$ (0.3 g, 3.6 mmol) was added, followed by Dess-Martin periodinane (0.78 g, 1.8 mmol). The reaction stirred at room temperature for two hours and was quenched with sat. $NaHCO_3$ (10 mL) and 10% w/v sodium bisulfite (10 mL). The mixture was stirred at room temperature for 30 minutes. The reaction mixture was extracted with $CH_2Cl_2$ and the combined organic layers were washed with brine. The organic layer was dried over $Na_2SO_4$, filtered, and concentrated in vacuo to yield 0.4 g of 79 as a white solid that was used without further purification.

Synthesis of 4-(1H-benzo[d]imidazol-2-yl)-5-(4-chlorophenylsulfonyl)-4,5,6,7-tetrahydro-2H-pyrazolo[4,3-c]pyridine (80). A flask was charged with silica (0.06 g) and $CH_2Cl_2$ (5 mL). Thionyl chloride (0.015 mL) was added dropwise. After the addition was complete, the reaction stirred at room temperature for 1 hour. Compound 79 (0.05 g, 0.15 mmol) was added, followed by phenylenediamine (0.017 g, 0.15 mmol). The reaction stirred at room temperature for 18 hours. The mixture was diluted with EtOH and the resulting suspension was filtered. The filtrate was concentrated in vacuo and the resulting residue was purified by preparative HPLC using Method [1] to yield 7.8 mg (13%) 80 as a white powder. $^1$H NMR ($CD_3OD$) δ 9.13 (s, 1H), 8.33 (s, 1H), 8.05-8.01 (m, 2H), 7.85-7.73 (m, 2H), 7.66 (d, J=8.7 Hz, 2H), 7.39 (d, J=9.0 Hz), 3.42-3.34 (m, 3H); MS (m/z) 414.0 (M+H)$^+$.

EXAMLE 6

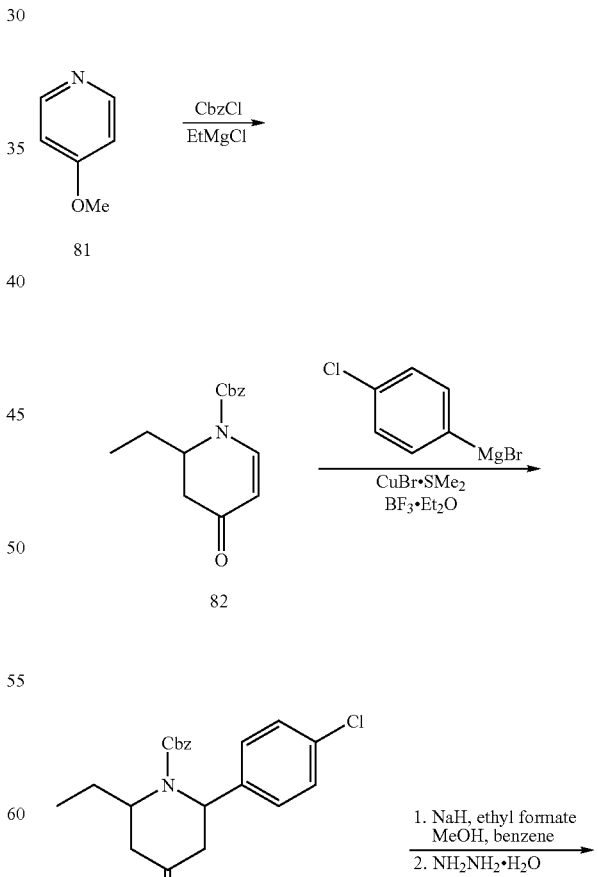

-continued

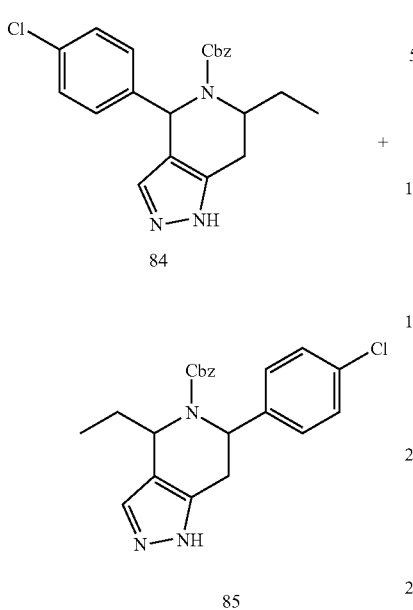

Synthesis of benzyl 2-ethyl-4-oxo-3,4-dihydropyridine-1(2H)-carboxylate (82). To a solution of 4-methoxylpyridine 81 (4.41 g, 40.5 mmol) in toluene (200 mL) at −20° C. was added CbzCl (5.7 ml, 40.5 mmol) in toluene (200 mL) dropwise. After 15 min, ethylmagnesium bromide (23 mL, 2M in THF, 46 mmol) was added dropwise. After 1 hr, 10% aqueous HCl (100 mL) was added and the mixture stirred overnight. The mixture was separated and the organic layer was washed with sat. NaHCO$_3$ and brine. It was dried and concentrated to afford 82 (9 g, 36.4 mmol, 89.9%) that was used directly in the next reaction.

Synthesis of benzyl 2-(4-chlorophenyl)-6-ethyl-4-oxopiperidine-1-carboxylate (83). CuBr.SMe$_2$ (5.6 g, 27.2 mmol) was added to dry THF (64 mL). It was cooled to −78° C. 4-Chlorophenylmagnesium bromide (27.2 mL, 1 M in THF, 27.2 mmol) was added to the mixture slowly over 1 hr at −78° C. Then BF$_3$.Et$_2$O (3.44 mL, 27.2 mmol) was added and the mixture was stirred for 5 min. Then ketone 82 (4 g, 8.1 mmol) in THF (55 mL) was added slowly over 1 hr at −78° C. After 2 hr stirring at −78° C., an aqueous solution of NH$_4$Cl/conc. NH$_4$OH (1:1, 20%, 60 mL) was added. The mixture was warmed to rt and extracted with EtOAc (200 mL×3). The combined organic layers were washed with brine, dried and concentrated to a residue and purified by silica gel chromatography (0-40% EtOAc/hexanes) to afford pure 83 (1 g, 2.7 mmol, 33%) as a mixture of cis stereoisomers.

Synthesis of benzyl 4-(4-chlorophenyl)-6-ethyl-6,7-dihydro-1H-pyrazolo[4,3-c]pyridine-5(4H)-carboxylate and benzyl 6-(4-chlorophenyl)-4-ethyl-6,7-dihydro-1H-pyrazolo[4,3-c]pyridine-5(4H)-carboxylate (84, 85). To compound 83 (0.91 g, 2.4 mmol) in benzene (24 mL) at rt was added NaH (193 mg, 60% in mineral oil, 4.8 mmol) and MeOH (10 □L). Ethyl formate (0.44 mL, 5.5 mmol) was added and the reaction was stirred for 3 hr. TLC showed the consumption of 83. The mixture was partitioned between aqueous citric acid (20%, 20 mL) and EtOAc (20 mL). The organic layer was washed with brine. It was dried and concentrated to a residue. The residue was dissolved in MeOH (20 mL). Hydrazine hydrate (0.24 mL, 4.9 mmol) was added and the mixture was stirred overnight at rt. The mixture was concentrated to a residue and purified by silica gel chromatography (10% to 50% EtOAc/Hexanes) to afford compounds 84 (0.2 g, 0.5 mmol, 22%) and 85 (0.5 g, 1.3 mmol, 54%).

EXAMPLE 7

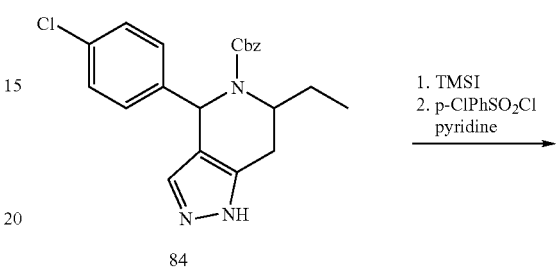

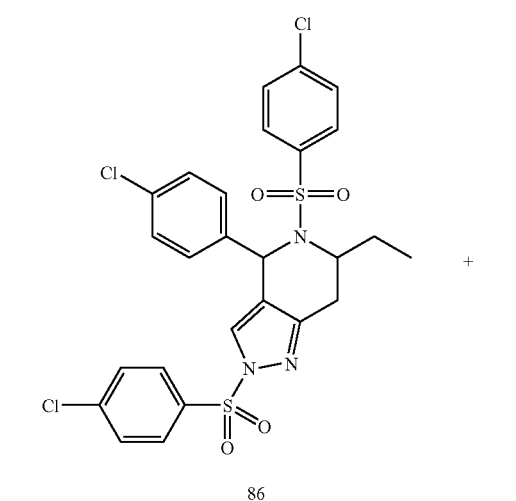

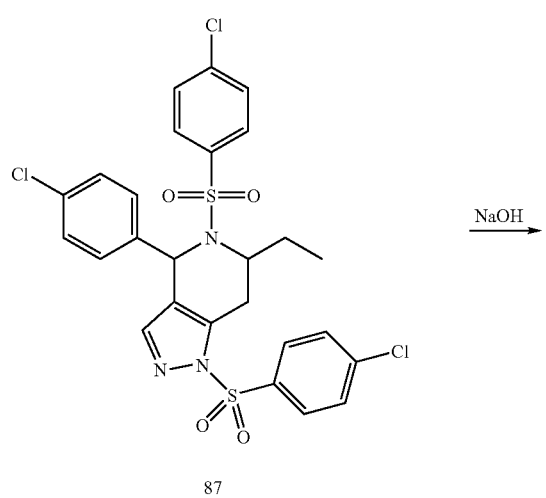

-continued

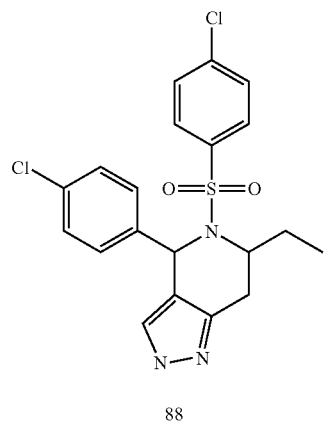

88

Synthesis of 4-(4-chlorophenyl)-2,5-bis(4-chlorophenylsulfonyl)-6-ethyl-4,5,6,7-tetrahydro-2H-pyrazolo[4,3-c]pyridine and 4-(4-chlorophenyl)-1,5-bis(4-chlorophenylsulfonyl)-6-ethyl-4,5,6,7-tetrahydro-1H-pyrazolo[4,3-c]pyridine (86, 87). To compound 84 (0.2 g, 0.5 mmol) in $CH_3CN$ (3 mL) at −10° C. in the dark was added TMSI (0.17 mL, 1.2 mmol). The solution was stirred in dark while warmed up to rt for 1 hr. It was stirred at rt for 3 hr. The reaction mixture was cooled to −10° C. again and HCl in MeOH (1.25 M, 1.7 mL, 2.1 mmol) was added and the reaction was warmed to rt while stirring for 1.5 hr. The mixture was evaporated to dryness then EtOAc (5 mL) was added. It was sonicated for 30 min and the solvent was decanted. This process was repeated another 2 times. The solid was dried and dissolved in pyridine (2 mL). p-Chlorophenylsulfonyl chloride (0.27 g, 1.3 mmol) was added and the mixture was stirred at rt overnight. The pyridine was removed and the residue was partitioned between EtOAc and $H_2O$. The organic layer was washed with 10% citric acid, sat. $NaHCO_3$ and brine. It was dried and concentrated and purified by silica gel chromatography (0% to 40% EtOAc/hexanes) to afford compounds 86 and 87 (70 mg, 0.1 mmol, 20%) as a mixture of cis regioisomers.

Synthesis of 4-(4-chlorophenyl)-5-(4-chlorophenylsulfonyl)-6-ethyl-4,5,6,7-tetrahydro-2H-pyrazolo[4,3-c]pyridine (88). To compounds 86 and 87 (70 mg, 0.1 mmol) in THF (3.4 mL) was added aqueous NaOH (1 M, 1.7 mL, 1.7 mmol) and $H_2O$ (1.7 mL)ᵣ The mixture was heated at 75° C. for 2 hr. The reaction was partitioned between EtOAc and $H_2O$. The organic layer was dried and concentrated and purified by silica gel chromatography (0% to 50% EtOAc/hexanes) to afford compound 88 (50 mg, 0.1 mmol, 100%) as a mixture of cis stereoisomers.

EXAMPLE 8

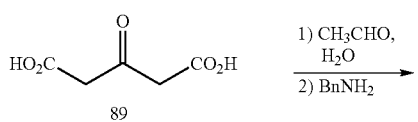

89

-continued

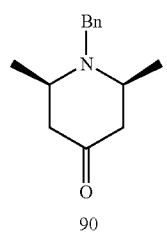 + 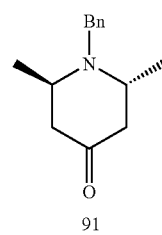

90        91

Synthesis of cis and trans-1-benzyl-2,6-dimethylpiperidin-4-one (90, 91). The 1 L 3-necked roundbottom flask, equipped with mechanical stirrer, reflux condenser, thermometer and addition funnel was charged with the solution of acetone dicarboxylic acid (40 g, 0.28 mol) in water (100 ml). The stirred solution was treated with acetaldehyde (25.3 g. 0.55 mol) at ambient temp. for 10 min., then benzylamine (30 ml, 0.28 mol) was added in small portions over 15 min. Vigorous gas evolution was observed and was moderated by use of a cooling bath (ice-water). The resulting yellow solution was stirred at ambient temperature for 78 hr. The stirred reaction mixture was acidified with aq. 1 N HCl to pH2, stirred for 1 hr then neutralized with aq. sodium bicarbonate to pH7 and extracted with $CH_2Cl_2$ (3×250 ml). Combined extracts were washed with brine and dried with anhydrous $Na_2SO_4$. The solution was filtered and evaporated to give brown liquid, 57 g. The isomeric piperidinones were separated by flash chromatography, eluting with $CH_2Cl_2$-EtOAc (9:1). The yield of the first-eluting compound, identified as the cis-isomer was 20 g. The yield of the second-eluting compound, identified as the trans-isomer was 25 g. A small amount of unresolved material was also collected (ca. 4.7 g).

EXAMPLE 9

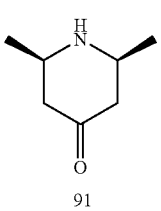

90

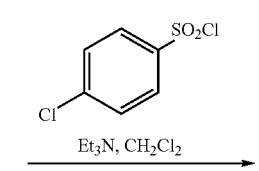

91

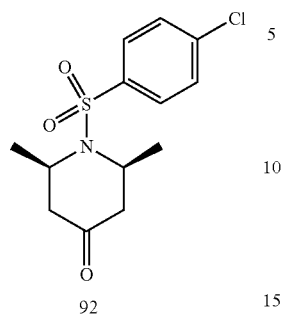

92

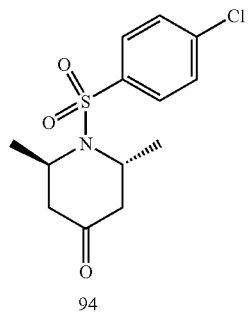

94

Synthesis of cis-2,6-dimethylpiperidin-4-one (91). The cis-N-benzyl-2,6 dimethylpiperidon-4-one 90 (1.85 g) was dissolved in EtOH (15 mL) and catalyst (0.5 g, Pd/C$_5$%) was added. Vigorously stirred slurry was kept under hydrogen atmosphere (60 psi) for 90 hr. The catalyst was removed by filtration through Celite and the filtrate was evaporated at 3 mmHg/40° C. The residue 91 (ca. 1.12 g) was used in next experiment without further purification.

Synthesis of cis-1-(4-chlorophenylsulfonyl)-2,6-dimethylpiperidin-4-one (92). The crude cis-2,6-dimethylpiperidin-4-one 91 from previous experiment (1.1 g, 8.6 mmol) was dissolved in CH$_2$Cl$_2$ (50 mL) and triethylamine (5 mL, 35 mmol) was added. Stirred solution was treated with 4-chlorobenzenesulfonyl chloride (2.2 g, 9.5 mmol). The mixture was stirred for 24 hr then was divided between water (100 mL) and CH$_2$Cl$_2$ (100 mL). Organic layer was washed with 0.2 N citric acid, water, brine and dried over anhydrous Na$_2$SO$_4$. The solution was filtered and evaporated. The residue was purified by flash chromatography, eluting with EtOAc-hexane (1:3) mixture. Yield 60 mg (2% after two steps).

Synthesis of trans-2,6-dimethylpiperidin-4-one (93). trans-N-Benzyl-2,6-dimethylpiperidin-4-one (91; 7.5 g) was dissolved in EtOH (20 mL) and the catalyst (0.8 g, Pd/C$_5$%) was added. The slurry was vigorously stirred and kept under a hydrogen atmosphere (60 psi) for 90 hr. The catalyst was removed by filtration through Celite and the filtrate was evaporated at 3 mmHg/40° C. The residue (ca. 5.2 g) was used without further purification.

Synthesis of trans-1-(4-chlorophenylsulfonyl)-2,6-dimethylpiperidin-4-one (94). trans-2,6-Dimethylpiperidin-4-one (93; 5.2 g, 39 mmol) was dissolved in CH$_2$Cl$_2$ (100 mL) and triethylamine (22 mL, 155 mmol) was added. The solution was stirred and treated with 4-chlorobenzenesulfonyl chloride (9.2 g, 43 mmol). The mixture was stirred for 24 hr and then partitioned between water (300 mL) and CH$_2$Cl$_2$ (300 mL). The organic layer was washed with 0.2 N citric acid, water, brine, dried over Na$_2$SO$_4$, filtered and the solvent evaporated. The residue (6.7 g) was purified by flash chromatography, eluting with EtOAc-hexane (1:3) mixture to yield 3.6 g (35%, 2 steps) of product 94.

EXAMPLE 10

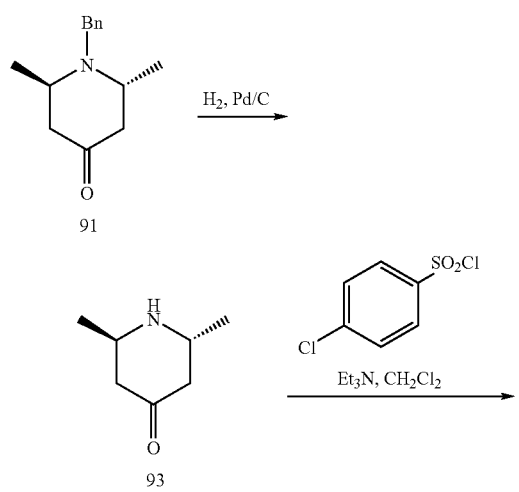

EXAMPLE 11

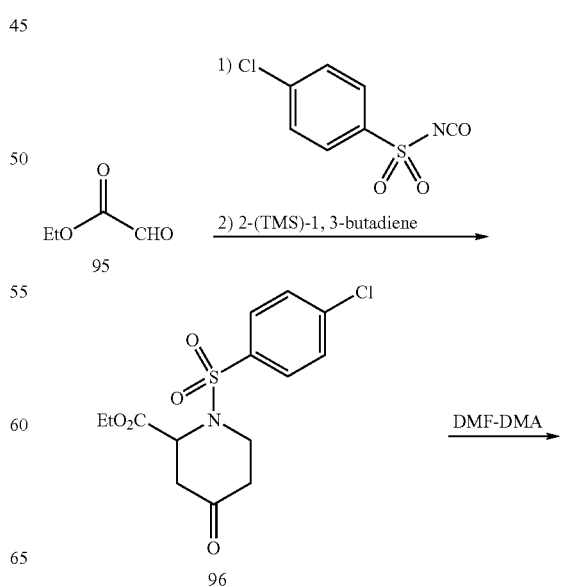

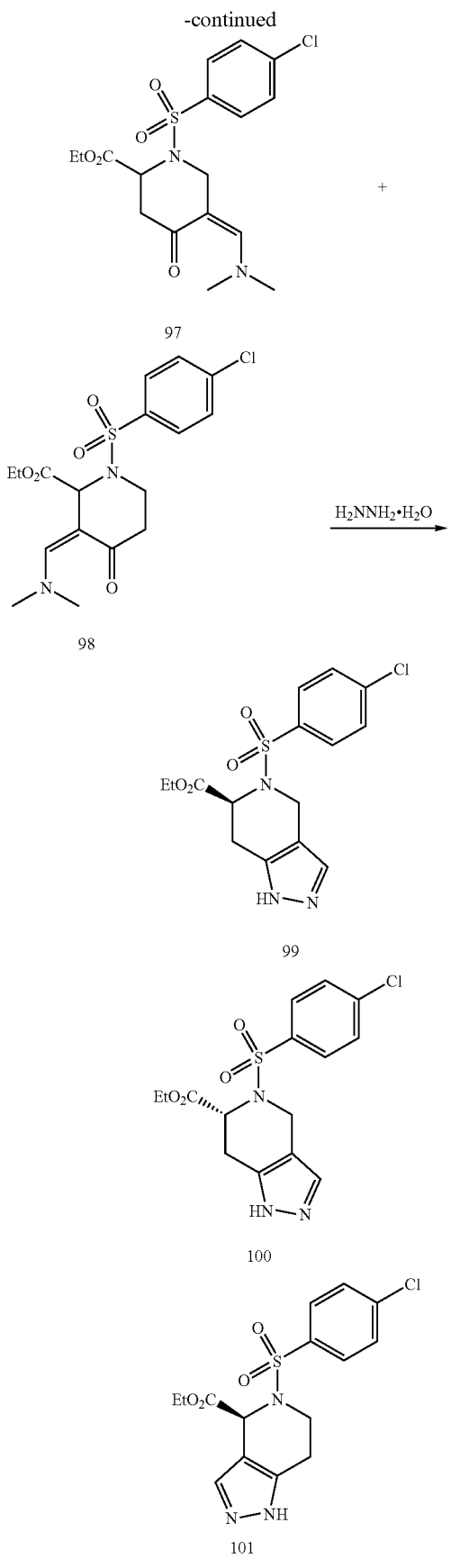

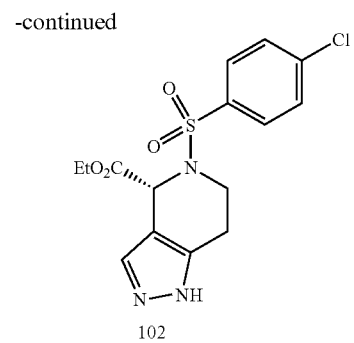

Synthesis of ethyl 1-(4-chlorophenylsulfonyl)-4-oxopiperidine-2-carboxylate (96). A solution of ethyl glyoxalate 95 (4.5 mL, 23 mmol) and 4-chlorobenzene sulfonylisocyanate (5.0 g, 23 mmol) in toluene (60 mL) was heated at reflux for 36 hours. The reaction mixture was cooled to room temperature and 2-(trimethylsilyl)-1,3-butadiene (3.3 g, 23 mmol) was added. The reaction was heated at 50° C. for 18 hours. The reaction mixture was concentrated in vacuo and the residue was purified by flash chromatography (5% EtOAc/hexanes) to yield 1.05 g (13%) 96 as a beige oil. $^1$H NMR (CDCl$_3$) δ 7.73 (d, 2H), 7.46 (d, 2H), 4.87 (d, 1H), 4.76-4.75 (m, 1H), 4.17-3.76 (m, 5H), 2.65-2.52 (m, 1H), 2.48-2.41 (m, 1H), 1.12 (t, 3H).

Synthesis of ethyl 1-(4-chlorophenylsulfonyl)-5-((dimethylamino)methylene)-4-oxopiperidine-2-carboxylate and ethyl 1-(4-chlorophenylsulfonyl)-3-((dimethylamino)methylene)-4-oxopiperidine-2-carboxylate (97, 98). Compound 96 (0.82 g, 2.4 mmol) was dissolved in DMF-DMA (10 mL) and heated at 40° C. for 2 hours. The reaction mixture was concentrated in vacuo to yield 900 mg (94%) of a mixture of compounds 97 and 98 as a yellow oil that was used without further purification.

Synthesis of (rel S)-ethyl 5-(4-chlorophenylsulfonyl)-4,5,6,7-tetrahydro-1H-pyrazolo[4,3-c]pyridine-6-carboxylate, (rel R)-ethyl 5-(4-chlorophenylsulfonyl)-4,5,6,7-tetrahydro-1H-pyrazolo[4,3-c]pyridine-6-carboxylate, (rel S)-ethyl 5-(4-chlorophenylsulfonyl)-4,5,6,7-tetrahydro-1H-pyrazolo[4,3-c]pyridine-4-carboxylate, and (rel R)-ethyl 5-(4-chlorophenylsulfonyl)-4,5,6,7-tetrahydro-1H-pyrazolo[4,3-c]pyridine-4-carboxylate (99, 100, 101, 102). A flask was charged with compounds 97 and 98 (900 mg, 2.24 mmol) in acetic acid (5 mL). Hydrazine hydrate (0.194 mL, 4.0 mmol) was added and the reaction stirred at room temperature for 18 hours. The reaction mixture was concentrated in vacuo and the residue was taken up in EtOAc. The organic layer was washed with sat. aqueous NaHCO$_3$, brine, dried over Na$_2$SO$_4$, filtered, and concentrated in vacuo to yield 0.55 g crude material as a mixture of regioisomers. The residue was purified by HPLC using Method [2] to afford compounds 99, 100, 101, and 102.

Ethyl 5-(4-chlorophenylsulfonyl)-4,5,6,7-tetrahydro-1H-pyrazolo[4,3-c]pyridine-6-carboxylate (Enantiomers A and B) $^1$H NMR (CDCl$_3$) δ 7.78 (d, J=8.4 Hz, 2H), 7.47 (d, J=8.4 Hz, 2H), 7.32 (s, 1H), 5.15 (dd, J=6.6, 1.5 Hz, 1H), 4.76 (d, J=13.8 Hz, 1H), 4.36 (d, J=13.8 Hz, 1H), 4.03-3.85 (m, 2H), 3.36 (d, J=15.6 Hz, 1H), 3.08 (dd, J=15.9, 6.6 Hz, 1H), 1.20 (d, J=6.0 Hz, 1H), 1.04 (t, J=6.9 Hz, 3H); MS (m/z) 376.0 (M+H)$^+$.

Ethyl 5-(4-chlorophenylsulfonyl)-4,5,6,7-tetrahydro-1H-pyrazolo[4,3-c]pyridine-4-carboxylate (Enantiomers A and B)

¹H NMR (CDCl₃) δ 7.78 (d, J=8.6 Hz, 2H), 7.55 (s, 1H), 7.44 (d, J=8.6 Hz, 2H), 5.67 (s, 1H), 4.11-4.06 (m, 3H), 3.57-3.47 (m, 1H), 2.72-2.70 (m, 2H), 1.19 (t, J=7.1 Hz, 3H); MS (m/z) 370.0 (M+H)⁺.

EXAMPLE 12

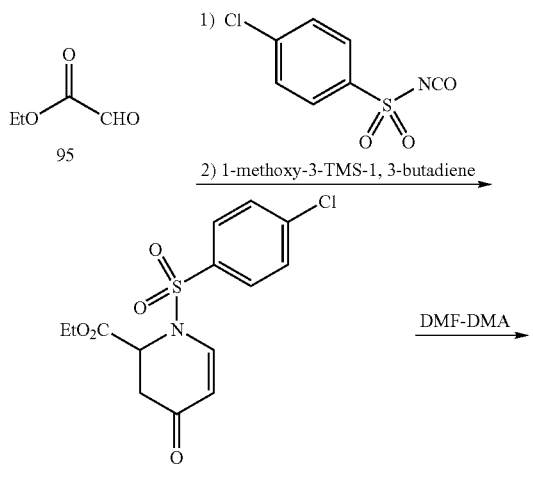

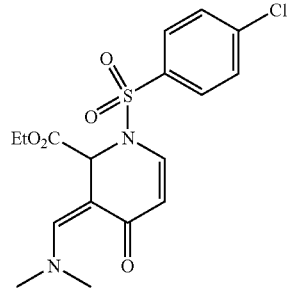

Synthesis of ethyl 1-(4-chlorophenylsulfonyl)-4-oxo-1,2,3,4-tetrahydropyridine-2-carboxylate (103). A solution of ethyl glyoxalate (27 mL, 0.14 mol) and 4-chlorobenzene sulfonylisocyanate (20 mL, 0.14 mol) in toluene (300 mL) was heated at reflux for 60 hours. The reaction mixture was cooled to room temperature and 1-methoxy-3-trimethylsilyl-1,3-butadiene (27 mL, 0.14 mol) was added, The reaction was heated at 50° C. for 18 hours. The reaction mixture was concentrated in vacuo and the residue was purified by flash chromatography (20% EtOAc/hexanes) to yield 16.0 g (34%) of compound 103 as a yellow oil. ¹H NMR (CDCl₃) δ 7.81 (d, 2H), 7.67 (dd, 1H), 7.55 (d, 2H), 5.40 (d, 1H), 5.01-4.97 (m, 1H), 4.13-4.03 (m, 3H), 2.86-2.81 (m, 2H), 1.16 (t, 3H).

Synthesis of ethyl 1-(4-chlorophenylsulfonyl)-3-((dimethylamino)methylene)-4-oxo-1,2,3,4-tetrahydropyridine-2-carboxylate (104). Compound 103 (5.0 g, 15 mmol) was dissolved in DMF-DMA (20 mL) and heated at 100° C. for 30 minutes. The reaction mixture was concentrated in vacuo to yield compound 104 as a yellow oil that was used without further purification.

Synthesis of ethyl 5-(4-chlorophenylsulfonyl)-4,5-dihydro-1H-pyrazolo[4,3-c]pyridine-4-carboxylate (105). A flask was charged with compound 104 (5.8 g, 14.6 mmol), acetic acid (10 mL) and EtOH (10 mL). Hydrazine hydrate (1.4 mL, 30 mmol) was added and the reaction stirred at room temperature for 2 hours. The reaction mixture was concentrated in vacuo and the residue was taken up in EtOAc. The organic layer was washed with sat. aq. NaHCO₃, brine, dried over Na₂SO₄, filtered, and concentrated in vacuo to yield crude material that was purified by flash chromatography (50% EtOAc/hexanes) to yield 1.63 g (30%) of compound 105 as a yellow foam. ¹H NMR (CDCl₃) δ 7.76 (d, J=6.3 Hz, 2H), 7.48-7.41 (m, 3H), 6.90-6.87 (m, 1H), 5.96-5.93 (m, 1H), 5.80 (s, 1H), 4.13-4.11 (m, 2H), 1.24-1.18 (m, 3H; MS (m/z) 368.0 (M+H)⁺.

EXAMPLE 13

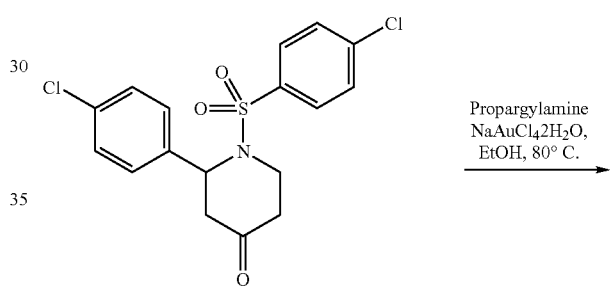

Synthesis of 7-(4-chlorophenyl)-6-(4-chlorophenylsulfonyl)-5,6,7,8-tetrahydro-1,6-naphthyridine and 5-(4-chlorophenyl)-6-(4-chlorophenylsulfonyl)-5,6,7,8-tetrahydro-1,6-naphthyridine (107, 108). A sealed tube was charged with compound 106 (177 mg, 0.46 mmol), propargylamine (59 μL, 0.92 mmol), NaAuCl$_4$·H$_2$O (4.5 mg, 0.012 mmol) and EtOH (2 mL). The reaction mixture was heated at 80° C. for 6.5 hours. The cooled reaction was filtered, concentrated and the residue was taken up in CH$_2$Cl$_2$. The organic portion was washed with 1.0 N HCl (3×10 mL), water (1×10 mL), sat. aq. NaHCO$_3$ (3×10 ml), brine (1×10 mL), dried (MgSO$_4$), filtered and concentrated to give the crude product. Purification by preparative TLC eluting with 2:1 hexanes/EtOAc yielded 37 mg of the less polar regioisomer 107 (TLC: 1:1 EtOAc/hexanes, $R_f$=0.38) and 34 mg of the more polar regioisomer 108 (TLC: 1:1 EtOAc/hexanes, $R_f$=0.25).

5-(4-Chlorophenyl)-6-(4-chlorophenylsulfonyl)-5,6,7,8-tetrahydro-1,6-naphthyridine $^1$H-NMR (CDCl$_3$) δ 8.46-8.44 (m, 1H), 7.59 (d, J=8.80, 2H), 7.31-7.25 (m, 5H), 7.15-7.12 (m, 1H), 7.09 (d, J=8.2 Hz, 2H), 6.21 (s, 1H), 3.98-3.91 (m, 1H), 3.38-3.28 (m, 1H), 2.86-2.81 (m, 2H); MS (m/z) 419.0 (M+H)$^+$.

7-(4-Chlorophenyl)-6-(4-chlorophenylsulfonyl)-5,6,7,8-tetrahydro-1,6-naphthyridine $^1$H-NMR (CDCl$_3$) δ 8.42 (d, J=4.4 Hz, 1H), 7.72 (d, J=8.2 Hz, 2H), 7.39 (d, J=8.8 Hz, 2H), 7.28-7.08 (m, 6H), 5.52 (d, J=5.5 Hz, 1H), 4.73 (d, J=17.0 Hz, 1H), 4.09 (d, J=17.0 Hz, 1H), 3.32 (dd, J=17.4, 2.2 Hz, 1H), 3.13 (dd, J=17.5, 6.6 Hz, 1H); MS (m/z) 419.0 (M+H)$^+$.

EXAMPLE 14

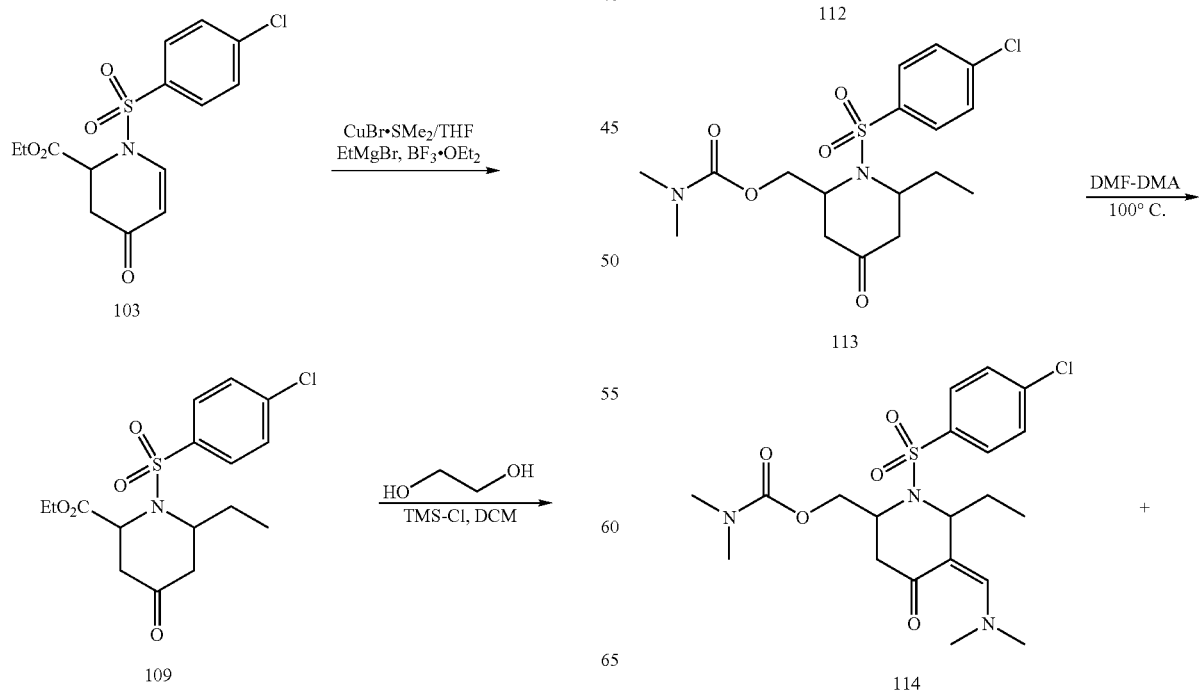

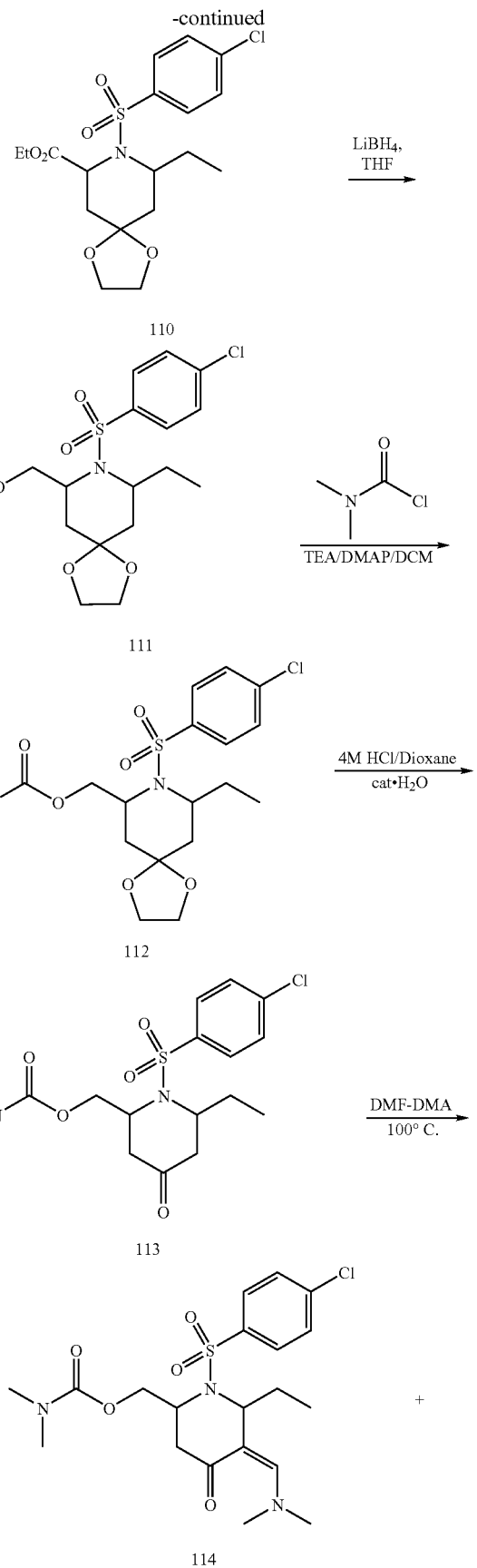

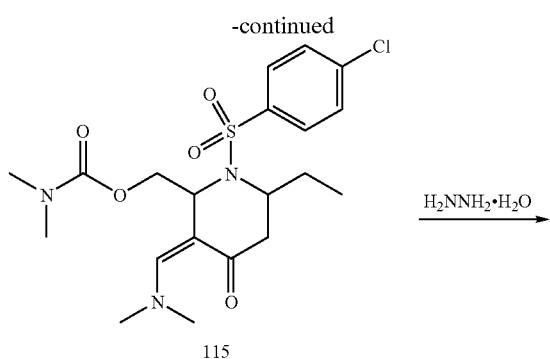

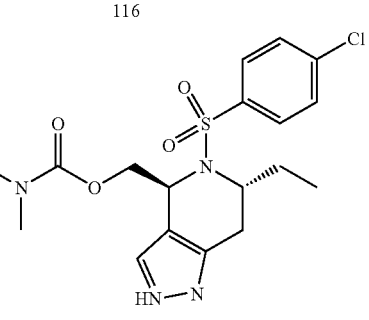

Synthesis of ethyl 1-(4-chlorophenylsulfonyl)-6-ethyl-4-oxopiperidine-2-carboxylate (109). $CuBr_2 \cdot SMe_2$ (19.13 g, 93.1 mmol) was placed into a flame-dried flask along with THF (250 ml). The mixture was cooled to −78° C. and ethylmagnesium bromide (31 ml, 3.0 M in ether, 93.1 mmol) was added slowly. The reaction was stirred for 45 minutes under nitrogen. Boron trifluoride dimethyl etherate was added (11.7 ml, 93,1 mmol) and the mixture stirred for 5 minutes. Ethyl 1-(4-chlorophenylsulfonyl)-4-oxo-1,2,3,4-tetrahydropyridine-2-carboxylate (103; 8.0 g, 23.3 mmol) was added via syringe pump over a 2 hour period while maintaining −78° C. bath temperature. The reaction was stirred for 4 hours and quenched with a 1:1 solution of 2% $NH_4Cl/NH_4OH$. An equal amount of EtOAc and water was added and the mixture was filtered to remove solids. The layers were separated and the aqueous layer was extracted with two more portions of EtOAc. The organic layers were combined and dried over $Na_2SO_4$ and concentrated to yield a colorless oil (7.74 g). The material was purified by column chromatography using EtOAc/hexanes gradients to yield 5.84 g (67%) of a mixture of cis/trans (4:96) isomers.

Synthesis of ethyl 8-(4-chlorophenylsulfonyl)-9-ethyl-1,4-dioxa-8-azaspiro[4.5]decane-7-carboxylate (110). Ethyl 1-(4-chlorophenylsulfonyl)-6-ethyl-4-oxopiperidine-2-carboxylate (109; 5.31 g, 14.2 mmol), TMSCl (5.41 ml, 42.6 mmol), and ethylene glycol (3.96 ml, 71.0 mmol) were added to $CH_2Cl_2$ (50 ml) and refluxed under nitrogen for 3 hours. The reaction mixture was concentrated tinder reduced pressure, and taken up in equal portions of EtOAc and water. The aqueous layer was washed with several more portions of EtOAc, dried over $Na_2SO_4$, and concentrated to give 5.67 g (96%) of a mixture of cis/trans (4:96) isomers as a clear oil which solidified upon standing. The material was used without further purification.

Synthesis of (8-(4-chlorophenylsulfonyl)-9-ethyl-1,4-dioxa-8-azaspiro[4.5]decan-7-yl)methanol (111). Ethyl 8-(4-chlorophenylsulfonyl)-9-ethyl-1,4-dioxa-8-azaspiro[4.5]decane-7-carboxylate (110; 2.47 g, 5.92 mmol) and lithium borohydride (4.7 ml, 2.0 M in THF, 9.48 mmol) were added to THF (15 ml). The mixture was stirred for 18 hours under nitrogen at rt which led to only a 25% conversion to the desired alcohol. Solid lithium borohydride was added in equivalent portions and the reaction monitored until the starting ester was consumed. The reaction mixture was concentrated under reduced pressure, and equal portions of EtOAc and Rochelle's salt were added. The aqueous layer was washed with several more portions of EtOAc, dried with $Na_2SO_4$, and concentrated to give 2.44 g of crude oil. The material was purified by column chromatography using EtOAc/hexanes gradients to yield 1.26 g (57%) of a mixture of cis/trans isomers.

Synthesis of (8-(4-chlorophenylsulfonyl)-9-ethyl-1,4-dioxa-8-azaspiro[4.5]decan-7-yl)methyl dimethylcarbamate (112). (8-(4-Chlorophenylsulfonyl)-9-ethyl-1,4-dioxa-8-azaspiro[4.5]decan-7-yl)methanol (111; 1.19 g, 3.18 mmol) and triethylamine (2.21 ml, 15.9 mmol) were added to $CH_2Cl_2$ (15 mL) in a flame-dried flask and placed tinder $N_2$. DMAP (77.8 mg, 0.637 mmol) was added and the mixture stirred for 5 minutes. Dimethylcarbamoyl chloride (0.88 mL, 1.54 mmol) was added dropwise and the reaction stirred for 18 hours. The reaction mixture was concentrated under reduced pressure, and equal portions of EtOAc and water were added. The aqueous layer was extracted with several more portions of EtOAc. The combined organic layers were washed with a dilute NaOH solution, 10% citric acid, brine, dried over $Na_2SO_4$ and concentrated to yield 940 mg of 112 as a yellow oil. The material was purified by column chromatography using EtOAc/hexanes gradients to yield 836 mg (59%) of a mixture of cis/trans isomers.

Synthesis of (1-(4-chlorophenylsulfonyl)-6-ethyl-4-oxopiperidin-2-yl)methyl dimethylcarbamate (113). (8-(4-Chlorophenylsulfonyl)-9-ethyl-1,4-dioxa-8-azaspiro[4.5]decan-7-yl)methyl dimethylcarbamate (112; 820 mg, 1.83 mmol) was dissolved in 4M HCl in dioxane (4 mL) and stirred for 18 hours. The reaction mixture was concentrated under reduced pressure and compound 113 as a crude oil 113 (715 mg, 97%) was isolated. The material was used without further purification.

Synthesis of (1-(4-chlorophenylsulfonyl)-5-((dimethylamino)methylene)-6-ethyl-4-oxopiperidin-2-yl)methyl dimethylcarbamate and (1-(4-chlorophenylsulfonyl)-3-((dimethylamino)methylene)-6-ethyl-4-oxopiperidin-2-yl) methyl dimethylcarbamate (114, 115). (1-(4-Chlorophenylsulfonyl)-6-ethyl-4-oxopiperidin-2-yl)methyl dimethylcarbamate (113; 0.69 g, 1.71 mmol) was dissolved in DMF-DMA (3.41 mL, 25.6 mmol) and heated to 90° C. for 1 hour. The reaction mixture was concentrated under reduced pressure and used without further purification.

Synthesis of ((rel 4R,6R)-5-(4-chlorophenylsulfonyl)-4-ethyl-4,5,6,7-tetrahydro-1H-pyrazolo[4,3-c]pyridin-6-yl) methyl dimethylcarbamate, ((rel 4R,6S)-5-(4-chlorophenylsulfonyl)-4-ethyl-4,5,6,7-tetrahydro-1H-pyrazolo[4,3-c] pyridin-6-yl)methyl dimethylcarbamate, ((rel 4R,6R)-5-(4-chlorophenylsulfonyl)-6-ethyl-4,5,6,7-tetrahydro-1H-pyrazolo[4,3-c]pyridin-4-yl)methyl dimethylcarbamate, and ((rel 4S,6R)-5-(4-chlorophenylsulfonyl)-6-ethyl-4,5,6,7-tetrahydro-1H-pyrazolo[4,3-c]pyridin-4-yl)methyl dimethylcarbamate (116, 117, 118, 119). Compounds 114 and 115 (780 mg from previous step, 1.71 mmol) were dissolved in EtOH (6 mL) and acetic acid (0.25 mL). Hydrazine hydrate (0.41 mL, 8.55 mmol) was added dropwise and the reaction was stirred for 18 hours at rt. The reaction mixture was concentrated under reduced pressure, and the crude material (600 mg) was purified by HPLC using Method [1] to yield 118 (16.8 mg), 119 (7.6 mg), 116 (49.4 mg), and 117 (5.6 mg).

cis-(5-(4-Chlorophenylsulfonyl)-6-ethyl-4,5,6,7-tetrahydro-1H-pyrazolo[4,3-c]pyridin-4-yl)methyl dimethylcarbamate $^1$H-NMR (CDCl$_3$) δ 7.74 (d, 2H, J=8.7 Hz), 7.56 (s, 1H), 7.44 (d, 2H, J=8.7 Hz), 5.41 (t, 1H, J=6.9 Hz), 4.38 (dd, 1H, J=11.9 Hz), 4.25-4.10 (m, 2H), 3.05 (s, 3H), 2.99 (s, 3H), 2.91 (m, 1H), 2.60 (d, 1H, J=16.4 Hz), 2.29 (d, 1H, J=16.4 Hz), 1.58 (m, 1H, J=7.2 Hz), 1.47 (m, 1H, J=7.2 Hz), 1.02 (t, 3H, J=7.2 Hz); 427.1 cis-(5-(4-Chlorophenylsulfonyl)-4-ethyl-4,5,6,7-tetrahydro-1H-pyrazolo[4,3-c]pyridin-6-yl)methyl dimethylcarbamate $^1$H-NMR (CDCl$_3$) δ 7.74 (d, 2H, J=8.7 Hz), 7.53 (s, 1H), 7.41 (d, 2H, J=8.7 Hz), 5.57 (dd, 1H, J=8.4 Hz), 4.34 (dd, 1H, J=8.4 Hz), 4.21 (dd, 1H, J=5.1 Hz), 3.59 (m, 1H), 2.92 (s, 3H), 2.89 (s, 3H), 2.82 (dd, 1H, J=4.0 Hz), 2.68 (dd, 1H, J=11.0 Hz), 2.11 (m, 1H, J=7.0 Hz), 1.87 (m, 1H, J=7.0 Hz), 0.98 (t, 3H, J=7.0 Hz); MS (m/z) 427.1 (M+H)$^+$.

trans-(5-(4-Chlorophenylsulfonyl)-4-ethyl-4,5,6,7-tetrahydro-1H-pyrazolo[4,3-c]pyridin-6-yl)methyl dimethylcarbamate $^1$H-NMR (CDCl$_3$) δ 7.67 (d, 2H, J=8.7 Hz), 7.51 (s, 1H), 7.37 (d, 2H, J=8.7 Hz), 5.85 (dd, 1H, J=8.4 Hz), 4.32 (dd, 1H, J=8.4 Hz), 4.19 (dd, 1H, J=5.1 Hz), 3.63 (m, 1H), 2.94 (s, 3H), 2.94 (s, 3H), 2.84 (dd, 1H, J=5.0 Hz), 2.70 (dd, 1H, J=10.0 Hz), 1.87 (m, 2H, J=7.0 Hz), 0.85 (t, 3H, J=7.0 Hz); MS (m/z) 427.1 (M+H)$^+$.

trans-(5-(4-Chlorophenylsulfonyl)-6-ethyl-4,5,6,7-tetrahydro-1H-pyrazolo[4,3-c]pyridin-4-yl)methyl dimethylcarbamate $^1$H-NMR (CDCl$_3$) δ 7.77 (s, 1H), 7.64 (d, 2H, J=8.7 Hz), 7.34 (d, 2H, J=8.7 Hz), 7.19 (d, 1H, J=7.1 Hz), 6.49 (br s, 1H), 5.33 (d, 1H, J=7.1 Hz), 3.40 (m, 1H), 3.13 (s, 3H), 3.07 (s, 3H), 2.96-2.79 (m, 2H), 1.57 (m, 2H, J=7.2 Hz), 0.86 (t, 3H, J=7.2 Hz); MS (m/z) 427.0 (M+H)$^+$.

EXAMPLE 15

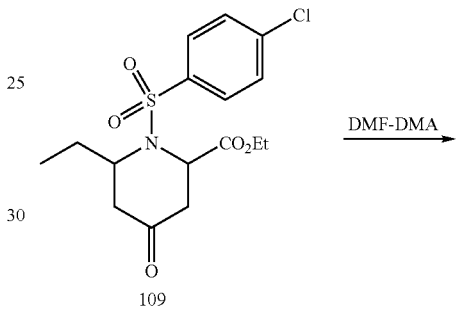

109

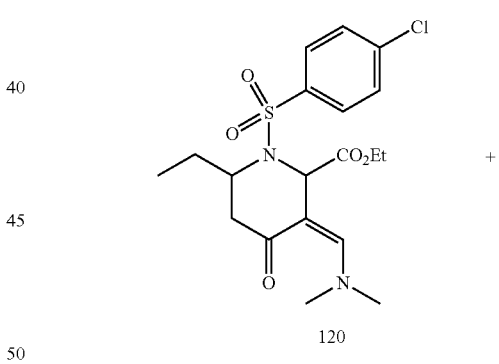

120

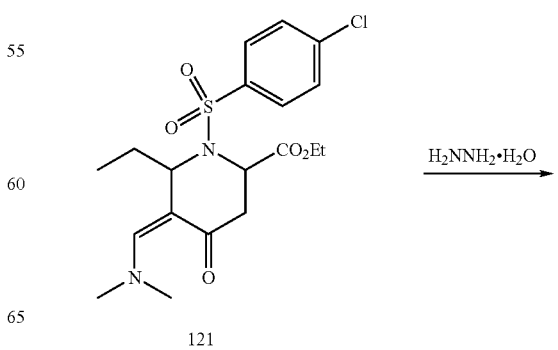

121

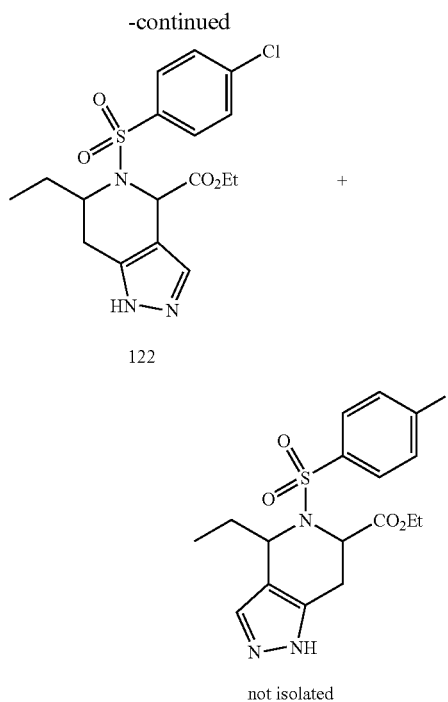

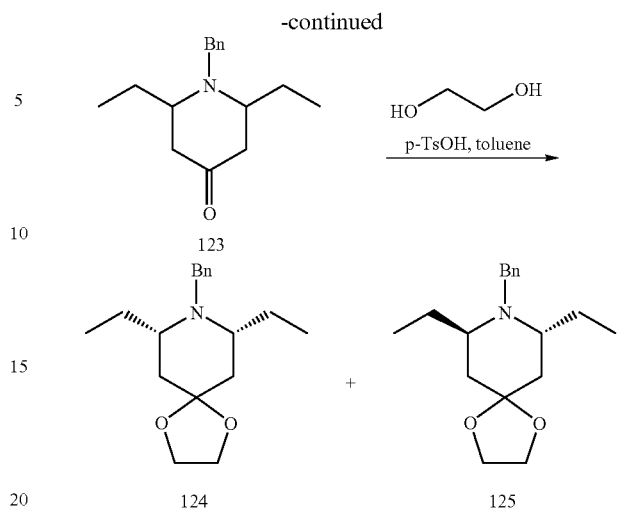

Synthesis of ethyl 1-(4-chlorophenylsulfonyl)-3-((dimethylamino)methylene)-6-ethyl-4-oxopiperidine-2-carboxylate and ethyl 1-(4-chlorophenylsulfonyl)-5-((dimethylamino)methylene)-6-ethyl-4-oxopiperidine-2-carboxylate (120, 121). Ethyl 1-(4-chlorophenylsulfonyl)-6-ethyl-4-oxopiperidine-2-carboxylate (109; 0.32 g, 0.86 mmol) was dissolved into DMF-DMA (1.71 mL, 12.8 mmol) and heated to 90° C. for 1 hour. The reaction mixture was concentrated under reduced pressure to yield a mixture of compounds 120 and 121 that was used without further purification.

Synthesis of ethyl 5-(4-chlorophenylsulfonyl)-6-ethyl-4,5,6,7-tetrahydro-1H-pyrazolo[4,3-c]pyridine-4-carboxylate (122). A mixture of compounds 120 and 121 (352 mg, 0.82 mmol) was dissolved in EtOH (3 mL) and acetic acid (0.25 mL). Hydrazine hydrate (0.20 mL, 4.11 mmol) was added dropwise and the reaction stirred for 18 hours at rt. The reaction mixture was concentrated under reduced pressure, and the crude material was purified by HPLC to yield 78 mg (28%) of compound 122. $^1$H-NMR (CDCl$_3$) δ 7.91 (d, 2H, J=8.4 Hz), 7.63 (s, 1H), 7.59 (d, 2H, J=8.4 Hz), 5.75 (s, 1H), 4.24 (m, 4H), 2.65 (d, 1H, J=15 Hz), 2.42 (dd, 1H, J=6.8 Hz), 1.53 (m, 1H), 1.32 (t, 3H, J=6.8 Hz), 1.25 (m, 1H), 0.90 (t, 3H, J=6.8 Hz); MS (m/z) 398.0 (M+H)$^+$.

EXAMPLE 16

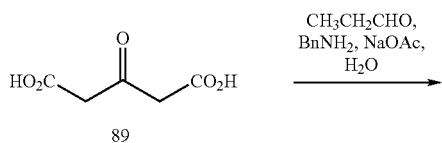

Synthesis of 1-benzyl-2,6-diethylpiperidin-4-one (123). A 1 L, 3-necked round-bottom flask, equipped with a mechanical stirrer, reflux condenser, thermometer and addition funnel was charged with a solution of propionaldehyde (25.3 g, 0.4 mol) in water (150 mL) and stirred. The solution was cooled in an ice-bath to 5° C. The solution was treated with benzylamine hydrochloride (37.2 g, 0.26 mol) and stirred at 5° C. for 30 min. Solid acetone dicarboxylic acid 89 (31.6 g, 0.2 mol) was added at 5° C., followed within 5 min with a solution of sodium acetate (7.65 g, 0.093 mol) in water (60 mL). The reaction mixture was stirred at 5° C. for 1 hour and then allowed to warm up to rt and stirred for 70 hours. CH$_2$Cl$_2$ (350 mL) was added and the pH of the mixture was adjusted to 9 by cautious addition of solid sodium carbonate. The organic layer was separated and the aqueous layer was extracted with CH$_2$Cl$_2$ (300 mL). The combined extracts were washed with sat. aq. sodium bicarbonate (200 mL), water (200 mL), brine (200 mL) and dried over anhydrous Na$_2$SO$_4$. The solution was filtered and evaporated to give a brown liquid, ca. 57 g. This was diluted with CH$_2$Cl$_2$ (100 mL) and filtered through a plug of basic alumina (ca. 3×2 in), washing with CH$_2$Cl$_2$ (1 L). The combined filtrates were evaporated to give the product 123 as a light orange liquid, 50.1 g, which was used without further purification.

Synthesis of (rel 7R,9S)-8-benzyl-7,9-diethyl-1,4-dioxa-8-azaspiro[4.5]decane and (rel 7R,9R)-8-benzyl-7,9-diethyl-1,4-dioxa-8-azaspiro[4.5]decane (124, 125). 1-Benzyl-2,6-diethylpiperidin-4-one (123; 11.5 g, 46.7 mmol) was dissolved in toluene (400 mL) and placed in a 3-necked, 1 L round-bottom flask, equipped with a mechanical stirrer, thermometer, Dean-Stark trap and reflux condenser. The solution was treated with anhydrous ethylene glycol (13.5 mL, 240 mmol) and p-toluenesulfonic acid (9.0 g, 53 mmol). The resulting dark solution was refluxed for 8 hr, while the trap was drained several times. The solution was cooled to rt, diluted with EtOAc (500 mL) and neutralized with sat. aq. sodium carbonate to pH 9. The organic layer was separated and the aqueous layer was extracted with EtOAc (250 mL). The combined extracts were washed with brine (250 mL) and dried over Na$_2$SO$_4$. The solution was filtered and evaporated to give 19 g of a dark-brown liquid. The isomeric products were separated by flash chromatography on silica gel, eluting with EtOAc-hexane (1:9). The first-eluting compound was identified as trans-N-benzyl-7,9-diethyl-1,4-dioxa-8-azaspiro[4.5]decane (125), yield 5.45 g (40%), the second-eluting compound was identified as cis-N-benzyl-7,9-diethyl-1,4-dioxa-8-azaspiro[4.5]decane (124), yield 7.78 g (57%).

EXAMPLE 17

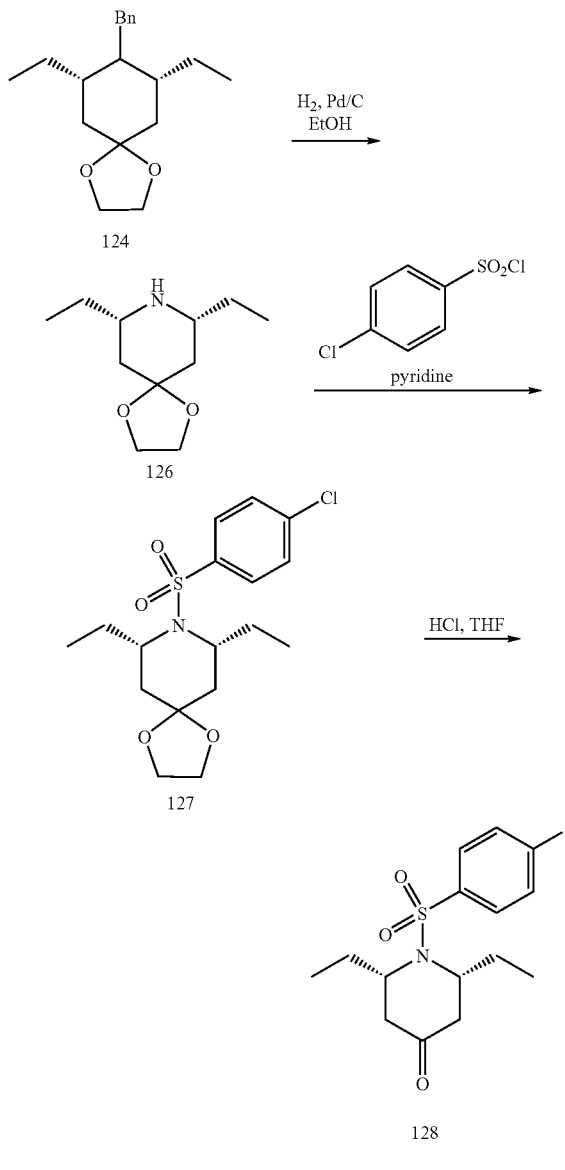

Synthesis of (rel 7R,9S)-7,9-diethyl-1,4-dioxa-8-azaspiro[4.5]decane (126). The cis-N-benzyl-7,9-diethyl-1,4-dioxa-8-azaspiro[4.5]decane (124; 9.1 g, 31 mmol) was dissolved in EtOH (50 mL). Catalyst (Pd/C 5%, 3.0 g) was added and the slurry was vigorously stirred under a hydrogen atmosphere (60 psi) at ambient temperature for 6 hr. The catalyst was removed by filtration through Celite (1×1 in), rinsing with EtOH (250 mL). The combined filtrates were evaporated to dryness to give the product 126 as a pale yellow viscous liquid, 6.1 g (>99% yield) which was used without further purification.

Synthesis of (rel 7R,9S)-8-(4-chlorophenylsulfonyl)-7,9-diethyl-1,4-dioxa-8-azaspiro[4.5]decane (127). The cis-7,9-diethyl-1,4-dioxa-8-azaspiro[4.5]decane 126 (2.48 g, 12.5 mmol) was dissolved in anhydrous pyridine (10 mL). 4-Chorobenzenesulfonyl chloride (8.3 g, 39.3 mmol) was added and the solution was placed in a 20 mL glass vial equipped with a magnetic stirbar, sealed under nitrogen and irradiated in a microwave reactor at 150° C. for 10 min. The products of two identical reactions, as described above, were combined, diluted with EtOAc (400 mL), washed with water (2×200 mL), 0.2N citric acid (2×200 mL), water (200 mL), sat. aq. sodium bicarbonate (200 mL) and dried over anhydrous Na$_2$SO$_4$. The solution was filtered and evaporated. The residue was purified by chromatography on silica gel, eluting with EtOAc-hexane (1:9) mixture to afford 2.16 g (24%) of product 127.

Synthesis of (rel 2S,6R)-1-(4-chlorophenylsulfonyl)-2,6-diethylpiperidin-4-one (128).

The cis-8-(4-chlorophenylsulfonyl)-7,9-diethyl-1,4-dioxa-8-azaspiro[4.5]decane (2.2 g, 5.88 mmol) was dissolved in THF (50 mL) and treated with conc. aq. HCl (8 mL) at ambient for 18 hr. The EtOAc (250 mL) was added, organic layer separated and aqueous extracted with EtOAc (100 mL). Combined extracts were washed with water (100 mL), sat. aq. sodium bicarbonate (100 mL) and dried over anhydrous Na$_2$SO$_4$. The solution was filtered and evaporated to give an oily product that solidified on standing, yield 1.85 g (95%) of compound 128.

EXAMPLE 18

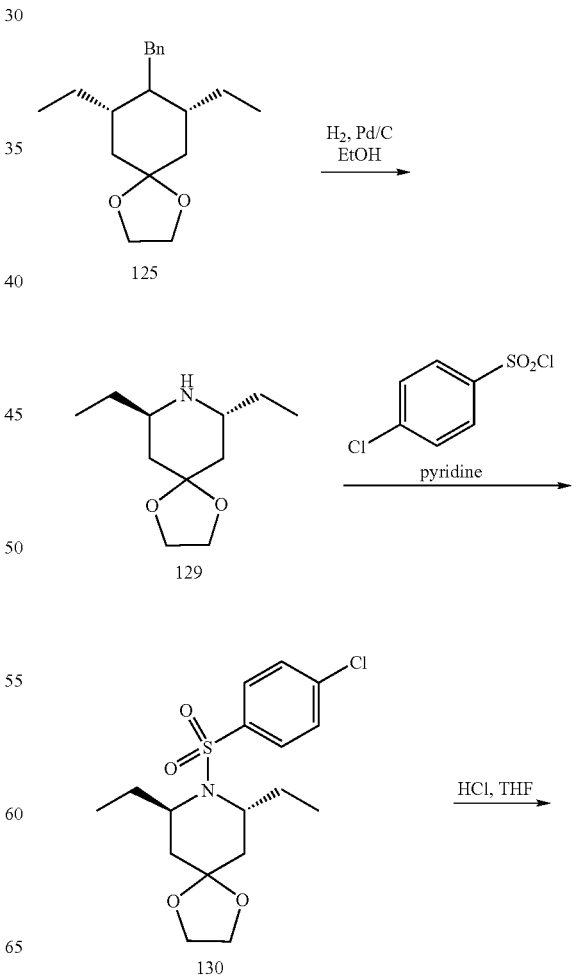

-continued

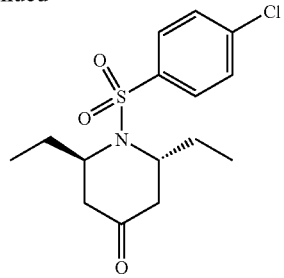

131

Synthesis of (rel 7R,9R)-7,9-diethyl-1,4-dioxa-8-azaspiro[4.5]decane (129). The trans-N-benzyl-7,9-diethyl-1,4-dioxa-8-azaspiro[4.5]decane (125; 6.5 g, 22 mmol) was dissolved in EtOH (50 mL). Catalyst (Pd/C$_5$%, 2.4 g) was added and the slurry was vigorously stirred under a hydrogen atmosphere (60 psi) at ambient temperature for 6 hr. The catalyst was removed by filtration through Celite (1×1 in), rinsing with EtOH (250 mL). The combined filtrates were evaporated to dryness to give the product as a pale yellow viscous liquid, 4.4 g (>99% yield) of xompouns 129, which was used without further purification.

Synthesis of (rel 7R,9R)-8-(4-chlorophenylsulfonyl)-7,9-diethyl-1,4-dioxa-8-azaspiro[4.5]decane (130). The trans-7,9-diethyl-1,4-dioxa-8-azaspiro[4.5]decane (129; 3.6 g, 18 mmol) was dissolved in anhydrous pyridine (15 mL). 4-Chorobenzenesulfonyl chloride (9.8 g, 47 mmol) was added and the solution was placed in a 20 mL glass vial equipped with a magnetic stirbar, sealed under nitrogen and irradiated in a microwave reactor at 150° C. for 10 min. The product was diluted with EtOAc (300 mL), washed with water (2×200 mL), 0.2N citric acid (2×200 mL), water (200 mL), sat. aq. sodium bicarbonate (200 mL) and dried with anhydrous Na$_2$SO$_4$. The solution was filtered and evaporated, the residue was purified by chromatography on silica gel, eluting with EtOAc-hexane (1:9) mixture to afford 3.8 g (57%) of product 130.

Synthesis of (rel 2R,6R)-1-(4-chlorophenylsulfonyl)-2,6-diethylpiperidin-4-one (131). The trans-8-(4-chlorophenylsulfonyl)-7,9-diethyl-1,4-dioxa-8-azaspiro[4.5]decane (130; 3.7 g, 10 mmol) was dissolved in THF (80 mL) and treated with conc. aq. HCl (10 mL) at ambient for 18 hr. The EtOAc (250 mL) was added, organic layer separated and aqueous extracted with EtOAc (100 mL). The combined extracts were washed with water (100 mL), sat. aq. sodium bicarbonate (100 mL) and dried over anhydrous Na$_2$SO$_4$. The solution was filtered and evaporated to give an oily product, that solidified on standing to yield 2.55 g (77%) of product.

EXAMPLE 19

6-Benzyl-5-(4-chlorophenylsulfonyl)-4,5,6,7-tetrahydro-1H-pyrazolo[4,3-c]pyridine Prepared as described for compound 55 in Example 1 using 2-(phenylmethyl)-4-piperidinone.

$^1$H NMR (CDCl$_3$) δ 7.61 (d, J=8.1 Hz, 2H), 7.42 (s, 1H), 7.37 (d, J=8.1 Hz, 2H), 7.28 (m, 3H), 7.10 (m, 2H), 4.86 (d, J=15.6 Hz, 1H), 468 (q, J=6.5 Hz, 1H), 4.25 (d, J=15.6 Hz, 1H), 2.73 (m, 4H), MS (m/z) 388.1 (M+H)$^+$.

EXAMPLE 20

5-(4-Chlorophenylsulfonyl)-6-isopropyl-4,5,6,7-tetrahydro-1H-pyrazolo[4,3-c]pyridine Benzyl 2-isopropyl-4-oxopiperidine-1-carboxylate, prepared as described for compound 67 in Example 3 using isopropylmagnesium chloride, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1.

$^1$H NMR (CDCl$_3$) δ 7.72 (d, J=9.0 Hz, 2H), 7.40 (d, J=9.0 Hz, 2H), 7.34 (s, 1H), 4.84 (d, J=16.6 Hz, 1H), 4.19 (d, J=16.6 Hz, 1H), 3.96 (dd, J=10.5, 6.0 Hz, 1H), 2.85 (d, J=16.2 Hz, 1H), 2.50 (dd, J=16.2, 6.0 Hz, 1H), 1.70 (m, 1H), 1.01 (d, J=6.6 Hz, 3H), 0.95 (d, J=6.6 Hz, 3H), MS (m/z) 340.0 (M+H)$^+$.

EXAMPLE 21

5-(4-Chlorophenylsulfonyl)-6-(4-fluorophenyl)-4,5,6,7-tetrahydro-1H-pyrazolo[4,3-Benzyl 2-(4-fluorophenyl)-4-oxopiperidine-1-carboxylate, prepared as described for compound 67 in Example using 4-fluorophenylmagnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1.

$^1$H NMR (CDCl$_3$) δ 7.74 (d, J=8.7 Hz, 2H), 7.40 (d, J=8.7 Hz, 2H), 7.30 (s, 1H), 7.21 (m, 2H), 6.95 (m, 2H), 5.61 (d, J=6.6 Hz, 1H), 4.78 (d, J=16.2 Hz, 1H), 3.85 (d, J=16.2 Hz, 1H), 3.22 (d, J=16.5 Hz, 1H), 2.92 (dd, J=16.5, 6.6 Hz, 1H), MS (m/z) 392.0 (M+H)$^+$.

EXAMPLE 22

6-(4-Chlorophenyl)-5-(4-chlorophenylsulfonyl)-4,5,6,7-tetrahydro-1H-pyrazolo[4,3-c]pyridine Benzyl 2-(4-chlorophenyl)-4-oxopiperidine-1-carboxylate, 67, was formylated and treated with hydrazine hydrate as described for compounds 50 and 51 in Example 1 to give benzyl 6-(4-chlorophenyl)-6,7-dihydro-1H-pyrazolo[4,3-c]pyridine-5(4H)-carboxylate which was then deprotected and sulfonylated as described for compound 84 in Example 7.

$^1$H NMR (CDCl$_3$) δ 7.71 (d, J=8.7 Hz, 2H), 7.37 (d, J=9.0 Hz, 2H), 7.26 (s, 1H), 7.18 (d, J=8.7 Hz, 2H), 7.12 (d, J=8.7 Hz, 2H), 5.56 (d, J=6.6 Hz, 1H), 4.74 (d, J=16.5 Hz, 1H), 3.82 (d, J=15.90 Hz, 1H), 3.18 (d, J=16.50 Hz, 1H), 2.91 (dd, J=16.50, 6.6 Hz, 1H), MS (m/z) 408.0, (M+H)$^+$.

EXAMPLE 23

6-(4-Chlorophenyl)-5-(4-chlorophenylsulfonyl)-4,5,6,7-tetrahydro-1H-pyrazolo[4,3-c]pyridine (Enantiomers A and B) Benzyl 2-(4-chlorophenyl)-4-oxopiperidine-1-carboxylate, 67, was formylated and treated with hydrazine hydrate as described for compounds 50 and 51 in Example 1 to give benzyl 6-(4-chlorophenyl)-6,7-dihydro-1H-pyrazolo[4,3-c]pyridine-5(4H)-carboxylate which was then deprotected and sulfonylated as described for compound 84 in Example 7. The enantiomers were separated by HPLC using Method [2].

$^1$H NMR (CDCl$_3$) δ 7.71 (d, J=8.7 Hz, 2H), 7.37 (d, J=9.0 Hz, 2H), 7.26 (s, 1H), 7.18 (d, J=8.7 Hz, 2H), 7.12 (d, J=8.7 Hz, 2H), 5.56 (d, J=6.6 Hz, 1H), 4.74 (d, J=16.5 Hz, 1H), 3.82 (d, J=15.90 Hz, 1H), 3.18 (d, J=16.50 Hz, 1H), 2.91 (dd, J=16.50, 6.6 Hz, 1H); MS (m/z) 408.0, (M+H)$^+$.

EXAMPLE 24

5-(4-Chlorophenylsulfonyl)-6-(3,5-difluorophenyl)-4,5,6,7-tetrahydro-1H-pyrazolo[4,3-c]pyridine Benzyl 2-(3,5-difluorophenyl)-4-oxopiperidine-1-carboxylate, prepared as described for compound 67 in Example 3 using 3,5-difluorophenylmagnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1.

$^1$H NMR (CDCl$_3$) δ 7.73 (d, J=8.7 Hz, 2H), 7.41 (d, J=8.4 Hz, 2H), 7.29 (s, 1H), 6.76 (d, J=6.6 Hz, 2H), 6.71-6.65 (m, 1H), 5.56 (d, J=6.0 Hz, 1H), 4.79 (d, J=16.5 Hz, 1H), 3.92 (d, J=15.9 Hz, 1H), 3.17 (d, J=16.5 Hz, 1H), 2.90 (dd, J=16.5, 6.6 Hz, 1H).

EXAMPLE 25

5-(5-Chlorothiophen-2-ylsulfonyl)-6-phenyl-4,5,6,7-tetrahydro-1H-pyrazolo[4,3-c]pyridine Prepared as described in Example 1 using 5-chloro-2-thiophenesulfonyl chloride. MS (m/z) 410.0, (M+H)$^+$.

EXAMPLE 26

5-(4-Chlorophenylsulfonyl)-6-(3,5-difluorophenyl)-4,5,6,7-tetrahydro-1H-pyrazolo[4,3-c]pyridine (Enantiomers A and B) Benzyl 2-(3,5-difluorophenyl)-4-oxopiperidine-1-carboxylate, prepared as described for compound 67 in Example 3 using 3,5-difluorophenylmagnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1. The enantiomers were separated using HPLC Method [2].

$^1$H NMR (CDCl$_3$) δ 7.73 (d, J=6.0 Hz, 2H), 7.41 (d, J=9.0 Hz, 2H), 7.29 (s, 1H), 6.76 (d, J=6.0 Hz, 2H), 6.72-6.65 (m, 1H), 5.56 (d, J=6 Hz, 1H), 4.79 (d, J=18.0 Hz, 1H), 3.92 (d, J=15.0 Hz, 1H), 3.17 (d, J=15.0 Hz, 1H), 2.90 (dd, J=15.0, 6.0 Hz, 1H) MS (m/z) 410.0, (M+H)$^+$.

EXAMPLE 27

5-(4-Chlorophenylsulfonyl)-6-(3-fluorophenyl)-4,5,6,7-tetrahydro-1H-pyrazolo[4,3-c]pyridine Benzyl 2-(3-fluorophenyl)-4-oxopiperidine-1-carboxylate, prepared as described for compound 67 in Example 3 using (3-fluorophenyl)magnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1.

$^1$H NMR (CDCl$_3$) δ 7.73 (d, J=6.0 Hz, 2H), 7.39 (d, J=9.0 Hz, 2H), 7.28 (s, 1H), 7.23-7.18 (m, 1H), 7.02 (d, J=9.0 Hz, 1H), 6.96-6.90 (m, 2H), 5.60 (d, J=6.0 Hz, 1H), 4.79 (d, J=15.0 Hz, 1H), 3.89 (d, J=15.0 Hz, 1H), 3.22 (d, J=15.0 Hz, 1H), 2.92 (dd, J=18.0, 6.0 Hz, 1H); MS (m/z) 392.0, (M+H)$^+$.

EXAMPLE 28

5-(4-Chlorophenylsulfonyl)-6-(4-fluorophenyl)-4,5,6,7-tetrahydro-1H-pyrazolo[4,3-c]pyridine (Enantiomers A and B) Benzyl 2-(4-fluorophenyl)-4-oxopiperidine-1-carboxylate, prepared as described for compound 67 in Example using 4-fluorophenylmagnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1. The enantiomers were separated using HPLC Method [2].

$^1$H NMR (CDCl$_3$) δ 7.74 (d, J=8.7 Hz, 2H), 7.40 (d, J=8.7 Hz, 2H), 7.30 (s, 1H), 7.21 (m, 2H), 6.95 (m, 2H), 5.61 (d, J=6.6 Hz, 1H), 4.78 (d, J=16.2 Hz, 1H), 3.85 (d, J=16.2 Hz, 1H), 3.22 (d, J=16.5 Hz, 1H), 2.92 (dd, J=16.5, 6.6 Hz, 1H); MS (m/z) 392.0 (M+H)$^+$.

EXAMPLE 29

5-(4-Chlorophenylsulfonyl)-6-isopropyl-4,5,6,7-tetrahydro-1H-pyrazolo[4,3-c]pyridine Benzyl 2-isopropyl-4-oxopiperidine-1-carboxylate, prepared as described for compound 67 in Example 3 using isopropylmagnesium chloride, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1. The enantiomers were separated using HPLC Method [2].

$^1$H NMR (CDCl$_3$) δ 7.72 (d, J=9.0 Hz, 2H), 7.41 (d, J=9.0 Hz, 2H), 7.34 (s, 1H), 4.84 (d, J=16.6 Hz, 1H), 4.19 (d, J=16.6 Hz, 1H), 3.96 (dd, J=10.5, 6.0 Hz, 1H), 2.85 (d, J=16.2 Hz, 1H), 2.50 (dd, J=16.2, 6.0 Hz, 1H), 1.70 (m, 1H), 1.01 (d, J=6.6 Hz, 3H), 0.95 (d, J=6.6 Hz, 3H); MS (m/z) 436.1 (M+H)$^+$.

EXAMPLE 30

5-(4-Chlorophenylsulfonyl)-6-(3-fluorophenyl)-4,5,6,7-tetrahydro-1H-pyrazolo[4,3-c]pyridine (Enantiomers A and B)

Benzyl 2-isopropyl-4-oxopiperidine-1-carboxylate, prepared as described for compound 67 in Example 3 using isopropylmagnesium chloride, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1. The enantiomers were separated using HPLC Method [2].

$^1$H NMR (CDCl$_3$) δ 7.72 (d, J=9.0 Hz, 2H), 7.40 (d, J=9.0 Hz, 2H), 7.34 (s, 1H), 4.84 (d, J=16.6 Hz, 1H), 4.19 (d, J=16.6 Hz, 1H), 3.96 (dd, J=10.5, 6.0 Hz, 1H), 2.85 (d, J=16.2 Hz,

1H), 2.50 (dd, J=16.2, 6.0 Hz, 1H), 1.70 (m, 1H), 1.01 (d, J=6.6 Hz, 3H), 0.95 (d, J=6.6 Hz, 3H); MS (m/z) 436.1 (M+H)$^+$.

EXAMPLE 31

5-(4-Chlorophenylsulfonyl)-6-(3-fluorophenyl)-4,5,6,7-tetrahydro-1H-pyrazolo[4,3-c]pyridine (Enantiomers A and B) Benzyl 2-(3-fluorophenyl)-4-oxopiperidine-1-carboxylate, prepared as described for compound 67 in Example 3 using (3-fluorophenyl)magnesium bromide, was formylated and treated with hydrazine hydrate as described for compound 50 in Example 1 to give benzyl 6-isopropyl-6,7-dihydro-1H-pyrazolo[4,3-c]pyridine-5(4H)-carboxylate. This compound was then deprotected and treated with 4-chlorophenylsulfonyl chloride followed by NaOH as described for compound 52 in Example 1. The enantiomers were separated using HPLC Method [2].

$^1$H NMR (CDCl$_3$) δ 7.73 (d, J=8.7 Hz, 2H), 7.39 (d, J=8.4 Hz, 2H), 7.28 (s, 1H), 7.22-7.18 (m, 1H), 7.02 (d, J=7.8 Hz, 1H), 6.95-6.89 (m, 2H), 5.59 (d, J=6.3 Hz, 1H), 4.78 (d, J=15.9 Hz, 1H), 3.88 (d, J=15.9 Hz, 1H), 3.21 (d, J=16.5 Hz, 1H), 2.92 (dd, J=16.8, 6.6 Hz, 1H); MS (m/z) 392.1 (M+H)$^+$.

EXAMPLE 32 cis-6-(4-Chlorophenyl)-5-(4-chlorophenylsulfonyl)-4-ethyl-4,5,6,7-tetrahydro-1H-pyrazolo[4,3-c]pyridine Prepared as described for compound 88 in Example 7 using compound 85.

$^1$H NMR (CDCl$_3$) δ 7.43 (s, 1H), 7.19 (s, 4H), 7.11 (d, J=8.4 Hz, 2H), 7.05 (d, J=8.4 Hz, 2H), 5.30 (t, J=7.5 Hz, 1H), 4.84 (dd, J=10.5, 3.9 Hz, 1H), 3.63 (dd, J=15.5, 10.5 Hz, 1H), 3.05 (dd, J=15.5, 3.9 Hz, 1H), 2.01 (m, 1H), 1.84 (m, 1H), 1.06 (t, J=7.2 Hz, 3H); MS (m/z) 436.0 (M+H)$^+$.

EXAMPLE 33 trans-5-(4-Chlorophenylsulfonyl)-4,6-dimethyl-4,5,6,7-tetrahydro-1H-pyrazolo[4,3-c]pyridine trans-1-(4-Chlorophenylsulfonyl)-2,6-dimethylpiperidin-4-one (94) was treated with DMF-DMA followed by hydrazine hydrate as described for compound 71 in Example 4.
$^1$H-NMR (CD$_3$OD) δ 7.81-7.79 (m, 2H), 7.62 (m, 3H), 5.38 (q, J=7.1 Hz, 1H), 4.20-4.13, (m, 1H), 2.78 (dd, J=16.2, 4.4 Hz, 1H), 2.56-2.48 (m, 1H), 1.54-1.47 (m, 6H); MS (m/z) 326.0 (M+H)$^+$.

EXAMPLE 34 cis-5-(4-Chlorophenylsulfonyl)-4,6-dimethyl-4,5,6,7-tetrahydro-1H-pyrazolo[4,3-c]pyridine cis-1-(4-Chlorophenylsulfonyl)-2,6-dimethylpiperidin-4-one (92) was treated with DMF-DMA followed by hydrazine hydrate as described for compound 71 in Example 4.

$^1$H-NMR (CD$_3$OD) δ 7.88-7.79 (m, 2H), 7.58-7.50 (m, 3H), 5.36 (q, J=6.6 Hz, 1H), 2.76 (dd, J=15.9, 4.4 Hz, 1H), 2.53-2.48 (m, 1H), 1.53-1.47 (m, 6H); MS (m/z) 436.0 (M+H)$^+$.

EXAMPLE 35

5-(4-Chlorophenylsulfonyl)-6-(pyridin-3-yl)-4,5,6,7-tetrahydro-1H-pyrazolo[4,3-c]pyridine and 5-(4-chlorophenylsulfonyl)-4-(pyridin-3-yl)-4,5,6,7-tetrahydro-1H-pyrazolo[4,3-c]pyridine Prepared as described in Example 4 using pyridine-3-carboxaldehyde.

$^1$H NMR (CD$_3$OD) δ 8.93 (s, 1H), 8.68-8.56 (m, 4H), 8.38-8.35 (m, 1H), 8.15 (m, 1H), 7.99-7.98 (m, 1H), 7.86-7.75 (m, 4H), 7.55-7.51 (m, 5H), 7.40-7.30 (m, 2H), 6.56 (s, 0.5H), 5.86-5.83 (m, 1H), 3.98-3.93 (m, 1H), 2.96-2.89 (m, 1H), 2.58-2.42 (m, 1.5H); MS (m/z) 375.0 (M+H)$^+$.

EXAMPLE 36

5-(4-Chlorophenylsulfonyl)-6-(pyridin-4-yl)-4,5,6,7-tetrahydro-1H-pyrazolo[4,3-c]pyridine and 5-(4-chlorophenylsulfonyl)-4-(pyridin-4-yl)-4,5,6,7-tetrahydro-1H-pyrazolo[4,3-c]pyridine Prepared as described in Example 4 using pyridine-4-carboxaldehyde.

$^1$H NMR (CD$_3$OD) δ 8.44 (bs, 3H), 7.88 (d, J=8.5 Hz, 2H), 7.53 (d, J=8.5 Hz, 2H), 7.36-7.30 (m, 3H), 5.71 (d, J=6.0 Hz, 1H), 3.94 (d, 16.3 Hz, 1H), 2.88 (dd, J=16.6, 6.3 Hz, 1H), 2.25 (d, J=21.0 Hz, 1H); MS (m/z) 375.0 (M+H)$^+$.

EXAMPLE 37 cis-5-(4-Chlorophenylsulfonyl)-4,6-diethyl-4,5,6,7-tetrahydro-1H-pyrazolo[4,3-c]pyridine Prepared as described for compound 122 in Example 15 using compound 128.

$^1$H NMR (CDCl$_3$) δ 9.05 (bs, 1H), 7.70 (d, J=8.1 Hz, 2H), 7.46 (s, 1H), 7.39 (d, J=8.1 Hz, 2H), 4.97 (t, J=7.5 Hz, 1H), 4.18 (dd, J=6.9, 14.3 Hz, 1H), 2.55 (d, J=15.9 Hz, 1H), 2.27 (dd, J=6.6, 16.5 Hz, 1H), 1.93 (sept, J=7.5 Hz, 1H), 1.78 (sept, J=6.9 Hz, 1H), 1.58 (sept, J=7.5 Hz, 1H), 1.44 (sept, J=6.9 Hz, 1H), 1.18 (t, J=6.9 Hz, 3H), 0.97 (t, J=7.5 Hz, 3H); MS (m/z) 354.0 (M+H)$^+$.

EXAMPLE 38 cis-5-(4-Chlorophenylsulfonyl)-4,6-diethyl-4,5,6,7-tetrahydro-1H-pyrazolo[4,3-c]pyridine (Enantiomers A and B)

Prepared as described for compound 122 in Example 15 using compound 128 followed by HPLC separation of the enantiomers using Method [2].

$^1$H NMR (CDCl$_3$) δ 9.05 (bs, 1H), 7.70 (d, J=8.1 Hz, 2H), 7.46 (s, 1H), 7.39 (d, J=8.1 Hz, 2H), 4.97 (t, J=7.5 Hz, 1H), 4.18 (dd, J=6.9, 14.3 Hz, 1H), 2.55 (d, J=15.9 Hz, 1H), 2.27 (dd, J=6.6, 16.5 Hz, 1H), 1.93 (sept, J=7.5 Hz, 1H), 1.78 (sept, J=6.9 Hz, 1H), 1.58 (sept, J=7.5 Hz, 1H), 1.44 (sept, J=6.9 Hz, 1H), 1.18 (t, J=6.9 Hz, 3H), 0.97 (t, J=7.5 Hz, 3H); MS (m/z) 354.0 (M+H)$^+$.

EXAMPLE 39 trans-5-(4-Chlorophenylsulfonyl)-4,6-diethyl-4,5,6,7-tetrahydro-1H-pyrazolo[4,3-c]pyridine Prepared as described for compound 122 in Example 15 using compound 131. $^1$H NMR (CDCl3) δ 7.66 (d, J=8.7 Hz, 2H), 7.34-7.30 (m, 3H), 5.11 (t, J=7.5 Hz, 1H), 3.51-3.44 (m, 1H), 2.63 (dd, J=3.9, 15.9 Hz, 1H), 2.40 (dd, J=11.4, 15.9 Hz, 1H), 2.22 (sept, J=7.2 Hz, 1H), 1.85-1.65 (m, 3H), 1.02-0.97 (m, 6H); MS (m/z) 354.0 (M+H)$^+$.

EXAMPLE 40

5-(4-Chlorophenylsulfonyl)-6-ethyl-6,7-dihydro-1H-pyrazolo[4,3-c]pyridin-4(5H)-one Prepared by $CrO_3/H_5IO_6$ oxidation of 5-(4-chlorophenylsulfonyl)-4,6-diethyl-4,5,6,7-tetrahydro-2H-pyrazolo[4,3-c]pyridine. See Yamazaki, S. Org. Left. 1999, 1(13), 2129.
$^1$H NMR (CDCl$_3$) δ 8.04 (d, J=8.7 Hz, 2H), 7.99 (s, 1H), 7.49 (s, J=8.3 Hz, 2H), 5.02-4.94 (m, 1H), 3.20 (dd, J=5.7, 13.5 Hz, 1H), 3.09 (dd, J=1.5, 16.5 Hz, 1H), 1.79-1.68 (m, 1H), 1.66-1.54 (m, 1H), 0.96 (t, J=7.8 Hz, 3H); MS (m/z) 340.0 (M+H)$^+$.

EXAMPLE 41

(5-(4-Chlorophenylsulfonyl)-4,5,6,7-tetrahydro-1H-pyrazolo[4,3-c]pyridin-4-yl)methanol Prepared by reduction of ester 100 as described for compound 110 in Example 14.
$^1$H NMR (CD$_3$OD) δ 7.82 (d, J=8.7 Hz, 2H), 7.48-7.45 (m, 3H), 5.10 (t, J=6.6 Hz, 1H), 4.14 (dd, J=15.0, 5.7 Hz, 1H), 3.75-3.59 (m, 2H), 3.49-3.35 (m, 1H), 2.52 (dd, J=16.2, 3.9 Hz, 1H), 2.43-2.32 (m, 1H), 2.15 (s, 1H), MS (m/z) 328.0 (M+H)$^+$.

EXAMPLE 42 trans-5-(4-Chlorophenylsulfonyl)-4,6-diethyl-4,5,6,7-tetrahydro-1H-pyrazolo[4,3-c]pyridine (Enantiomers A and B)

Prepared as described for compound 122 in Example 15 using compound 131 followed by HPLC separation of the enantiomers using Method [2].
$^1$H NMR (CDCl$_3$) δ 7.66 (d, J=8.7 Hz, 2H), 7.34-7.30 (m, 3H), 5.11 (t, J=7.5 Hz, 1H), 3.51-3.44 (m, 1H), 2.63 (dd, J=3.9, 15.9 Hz, 1H), 2.40 (dd, J=11.4, 15.9 Hz, 1H), 2.22 (sept, J=7.2 Hz, 1H), 1.85-1.65 (m, 3H), 1.02-0.97 (m, 6H); MS (m/z) 354.0 (M+H)$^+$.

EXAMPLE 43 cis-Diethyl 5-(4-chlorophenylsulfonyl)-4,5,6,7-tetrahydro-1H-pyrazolo[4,3-c]pyridine-4,6-dicarboxylate Prepared by sulfonylation of cis-4-oxo-2,6-piperidinedicarboxylic acid dimethyl ester (Hermann, K.; Dreiding, A. S. Helvetica Chimica Acta 1976, 59(2), 626-42) followed by formylation and pyrazole formation as shown in Example 1.
$^1$H NMR (CDCl$_3$) δ 7.90 (d, J=8.4 Hz, 2H), 7.61 (s, 1H), 7.49 (d, J=9.0 Hz, 2H), 5.87 (s, 1H), 5.01 (d, J=6.6 Hz, 1H), 3.68 (s, 3H), 3.54 (s, 3H), 3.18 (d, J=16.2 Hz, 1H), 2.89 (dd, J=6.6, 16.2 Hz, 1H); MS (m/z) 413.9 (M+H)$^+$.

EXAMPLE 44 cis-(5-(4-Chlorophenylsulfonyl)-4,5,6,7-tetrahydro-1H-pyrazolo[4,3-c]pyridine-4,6-diyl)dimethanol Prepared by reduction of cis-diethyl 5-(4-chlorophenylsulfonyl)-4,5,6,7-tetrahydro-1H-pyrazolo[4,3-c]pyridine-4,6-dicarboxylate using LiBH$_4$ as shown in Example 14.
$^1$H NMR (DMSO) δ 12.49 (bs, 1H), 7.81 (d, J=8.4 Hz, 2H), 7.61 (d, J=8.1 Hz, 2H), 7.48 (bs, 1H), 5.12 (t, J=5.0 Hz, 1H), 5.10 (bs, 1H), 4.98-4.79 (m, 1H), 4.24-4.17 (m, 1H), 3.67-3.61 (m, 1H), 3.21-3.10 (m, 3H), 2.72 (d, J=16.3 Hz, 1H), 2.15 (dd, J=5.9, 16.1 Hz, 1H); MS (m/z) 358.1 (M+H)$^+$.

EXAMPLE 45

(5-(4-Chlorophenylsulfonyl)-4,5,6,7-tetrahydro-1H-pyrazolo[4,3-c]pyridin-4-yl)methyl dimethylcarbamate Prepared by treatment of (5-(4-chlorophenylsulfonyl)-4,5,6,7-tetrahydro-1H-pyrazolo[4,3-c]pyridin-4-yl)methanol with dimethylcarbamyl chloride as described for compound 111 in Example 14.
$^1$H-NMR (CD$_3$OD) δ 7.80 (d, 2H, J=8.8 Hz), 7.57 (s, 1H), 7.50 (d, 2H, J=8.8 Hz), 5.41 (dd, 1H, J=4.6, 8.8 Hz), 4.29-4.13 (m, 3H), 3.50 (m, 1H), 2.93 (s, 6H), 2.99 (s, 3H), 2.56 (dd, 1H, J=4.6, 16.3 Hz), 2.32 (m, 1H); MS (m/z) 399.1 (M+H)$^+$.

EXAMPLE 46 cis-5-(4-Chlorophenylsulfonyl)-4,6-diethyl-5,6-dihydro-1H-pyrazolo[4,3-c]pyridin-7(4H)-one (Enantiomers A and B)

Prepared as described in Example 2 followed by separation of the enantiomers using HPLC Method [2].
$^1$H NMR (CDCl$_3$) δ 7.58 (d, J=7.5 Hz, 2H), 7.54 (s, 1H), 7.25 (d, J=8.2 Hz, 2H), 5.09 (t, J=7.5 Hz, 1H), 4.50 (dd, J=6.6, 9.9 Hz, 1H), 2.11-1.75 (m, 4H), 1.27-1.15 (m, 6H); MS (m/z) 368.0 (M+H)$^+$.

EXAMPLE 47 cis-4,6-Diethyl-5-(pyridin-2-ylsulfonyl)-4,5,6,7-tetrahydro-1H-pyrazolo[4,3-c]pyridine Prepared by treatment of 2,6-diethyl-1-(pyridin-2-ylsulfonyl)piperidin-4-one, which was prepared by sulfonylation of compound 126 using pyridine-2-sulfonyl chloride hydrochloride followed by deprotection as shown in Example 17, with DMF-DMA followed by pyrazole formation using hydrazine hydrate as shown in Example 15,
$^1$H-NMR (CDCl$_3$) δ 8.52 (d, J=8.5 Hz, 1H), 7.96 (d, J=7.7 Hz, 1H), 7.82 (t, J=7.8 Hz, 1H), 7.40-7.36 (m, 2H), 4.96 (t, J=7.1 Hz, 1H), 4.45-4.42 (m, 1H), 2.55-2.54 (m, 2H), 2.07-1.98 (m, 1H), 1.82-1.73 (m, 1H), 1.72-1.62 (m, 1H), 1.51-1.42 (m, 1H), 1.17 (t, J=7.1 Hz, 3H), 1.01 (t, J=7.1 Hz, 3H); MS (m/z) 321.1 (M+H)$^+$.

EXAMPLE 48 cis-4,6-Diethyl-5-(4-fluorophenylsulfonyl)-4,5,6,7-tetrahydro-1H-pyrazolo[4,3-c]pyridine Prepared by treatment of 2,6-diethyl-1-(4-fluorophenylsulfonyl)piperidin-4-one, which was prepared by sulfonylation of compound 126 using 4-fluorobenzenesulfonyl chloride followed by deprotection as shown in Example 17, with DMF-DMA followed by pyrazole formation using hydrazine hydrate as shown in Example 15.

$^1$H-NMR (CD$_3$OD) δ 7.81-7.76 (m, 2H), 7.42 (s, 1H), 7.12-7.06 (m, 2H), 4.98 (t, J=6.3 Hz, 1H), 4.21-4.09 (m, 1H), 2.51 (d, J=18.0 Hz, 1H), 2.16 (m, 1H), 1.95-1.93 (m, 1H), 1.81-1.78 (m, 1H), 1.64-1.62 (m, 1H), 1.47-1.42 (m, 1H), 1.21 (t, J=71 Hz, 3H), 1.00 (t, J=7.1 Hz, 3H) MS (m/z) 338.1 (M+H)$^+$.

EXAMPLE 49

2-(5-(4-Chlorophenylsulfonyl)-4,5,6,7-tetrahydro-1H-pyrazolo[4,3-c]pyridin-6-yl)thiazole Prepared as described for compounds 75 and 76 in Example 4 using 2-thiazolecarboxaldehyde.

$^1$H NMR (CDCl$_3$) δ 7.78 (d, J=8.4 Hz, 2H), 7.54 (d, J=2.4 Hz, 1H), 7.45 (d, J=8.4 Hz, 2H), 7.27 (s, 1H), 5.93 (d, J=6.3 Hz, 2H), 4.89 (d, J=15.6 Hz, 1H), 4.20 (d, J=15.9 Hz, 1H), 3.71 (d, J=16.8 Hz, 1H), 3.19-3.11 (m, 1H); MS (m/z) 381.0 (M+H)$^+$.

EXAMPLE 50

2-(5-(4-Chlorophenylsulfonyl)-4,5,6,7-tetrahydro-1H-pyrazolo[4,3-c]pyridin-4-yl)thiazole Prepared as described for compounds 73 and 74 in Example 4 using 2-thiazolecarboxaldehyde. $^1$H NMR (CDCl$_3$) δ 7.80-7.75 (m, 3H), 7.69 (d, J=3.3 Hz, 1H), 7.43 (d, J=8.4 Hz, 2H), 7.31 (d, J=3.3 Hz, 1H), 6.54 (s, 1H), 4.23-4.18 (m, 1H), 3.49-3.39 (m, 1H), 2.80 (s, 2H); MS (m/z) 381.0 (M+H)$^+$.

BIOLOGICAL EXAMPLES

Notch signaling assay for selective inhibitors of gamma secretase.

A convergence of evidence indicates that the gamma secretase complex, comprised of the presenilin subunits, mediates the intra-membrane cleavage of Amyloid precursor protein (APP), and the Notch family of proteins (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22; Mumm, J. S., E. H. Schroeter, M. T. Saxena, A. Griesemer, X. Tian, D. J. Pan, W. J. Ray and R. Kopan (2000). "A ligand-induced extracellular cleavage regulates gamma-secretase-like proteolytic activation of Notch1." Mol Cell 5(2): 197-206; Zhang, Z., P. Nadeau, W. Song, D. Donoviel, M. Yuan, A. Bernstein and B. A. Yankner (2000). "Presenilins are required for gamma-secretase cleavage of beta-APP and transmembrane cleavage of Notch-1." Nat Cell Biol 2(7): 463-5). Cleavage of APP by gamma secretase leads to beta-amyloid synthesis. Cleavage of Notch1 by gamma secretase results in release of the Notch intracellular domain (NICD), which translocates to the nucleus and activates gene expression (Jarriault, S., C. Brou, F. Logeat, E. H. Schroeter, R. Kopan and A. Israel (1995). "Signalling downstream of activated mammalian Notch." Nature 377(6547): 355-8; Kopan, R., E. H. Schroeter, H. Weintraub and J. S. Nye (1996). "Signal transduction by activated Notch: importance of proteolytic processing and its regulation by the extracellular domain." Proc Natl Acad Sci USA 93(4): 1683-8; Schroeter, E. H., J. A, Kisslinger and R. Kopan (1998). "Notch-1 signalling requires ligand-induced proteolytic release of intracellular domain." Nature 393(6683): 382-6). In particular, Notch signaling activates transcription of the mammalian homolog of the Drosophila transcription factor hairy-enhancer of split (Hes). Transcriptional activation of Hes1 is mediated by de-repression of CBF1/RBPJk upon binding by NICD in the nucleus. These facts have been exploited to develop a reporter gene assay for Notch Signaling Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." Mol Cell Biol 16(3): 952-9; Lu, F. M. and S. E. Lux (1996). "Constitutively active human Notch1 binds to the transcription factor CBF1 and stimulates transcription through a promoter containing a CBF1-responsive element." Proc Natl Acad Sci USA 93(11): 5663-7).

Gamma secretase inhibitors have been observed to block NICD formation, and inhibit Notch signaling (De Strooper, B., W. Annaert, P. Cupers, P. Saftig, K. Craessaerts, J. S. Mumm, E. H, Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22). Due to the importance of Notch signaling in cell fate determination, and tissue differentiation during both development and in the adult, inhibition of Notch signaling by gamma secretase inhibitors is postulated to be a limiting factor in their therapeutic utility. In order to identify selective gamma secretase inhibitors, we have employed a reporter gene based Notch signaling assay using a constitutively active rat Notch1 construct (ZEDN1) provided by Dr Gerry Weinmaster, who is at the University of California at Los Angeles (UCLA) as described in Shawber, C., D. Nofziger, J. J. Hsieh, C. Lindsell, O. Bogler, D. Hayward and G. Weinmaster (1996). "Notch signaling inhibits muscle cell differentiation through a CBF1-independent pathway." Development 122(12): 3765-73 in combination with the CBF1 repressible Luciferase reporter gene 4xwtCBF1 Luc (Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." Mol Cell Biol 16(3): 952-9).

When 4xwtCBF1 Luciferase is co-transfected with NotchδE (ZEDN1), gamma-secretase cleavage of NotchδE releases the Notch intracellular domain (NICD), which translocates to the nucleus and de-represses CBF1 mediated transcriptional repression, leading to transcription of the Luciferase reporter gene. Luciferase activity is easily assayed in cell extracts using commercially available kits. The activity of the reporter gene is directly correlated with gamma secretase cleavage of NotchδE, and as such, a reduction in Luciferase activity provides a convenient measure of inhibition of gamma secretase cleavage of NotchδE. A comparison of the IC$_{50}$ values of compounds for inhibition of Notch signaling versus inhibition of beta-amyloid production in 293sw cells is employed to guide in the selection of compounds that have the desired property of potent inhibition of beta-amyloid synthesis with minimal inhibition of Notch Signaling.

Compound 2a has an $IC_{50}$ value of less than 100 nM. Compound 7a has an $IC_{50}$ value of less than 50 nM. Compounds 1a, 3a, 4a, 5a, and 6a have an IC50 value of less than 25 nM.

Gamma-Secretase Assay

The gamma-secretase APP enzyme assay was designed to measure the specific proteolytic cleavage of an APP substrate (MBP-C125 Swe fusion protein) at the Aβ40 site. The assay used a partially purified extract of IMR-32 cell membranes as the gamma-secretase enzyme preparation and a recombinant fusion protein containing the C-terminal 125 amino acids of the Swedish variant of the APP (MBP-C125swe) as the substrate. This assay involved two steps beginning with the enzymatic reaction generating a cleavage product that was captured with an immobilized antibody specific for the neo-epitope Aβ40 site. The captured cleavage product was then detected in a sandwich ELISA assay with a biotinylated reporter antibody that is specific to Aβ (17-28). Streptavidin-linked alkaline phosphatase was then added that would generate a fluorescent signal proportional to the amount of cleavage product. This assay was used to discover small molecule inhibitors of gamma-secretase.

Materials and Methods:

Briefly, a 149 mg/ml solution of BIGCHAP detergent was made with water at 42° C. and then rotated for 30 minutes at the same temperature. This warmed solution of BigCHAPS (N,N-Bis(3-D-gluconamidopropyl)cholamide) detergent was used to dissolve Brain Extract Type-V (lipid containing a minimum of 40% phosphatidylethanolamine) from Sigma (St. Louis, Mo.) to a concentration of 8 mg/ml. This solution containing BigCHAPS and lipid at 8 mg/ml is then diluted to 0.53 mg/ml lipid with a pre-warmed solution of Hepes and sodium chloride. This final solution containing Hepes buffer, sodium chloride, BigCHAPS detergent and lipid is used to create working solutions of both gamma-secretase (25 Units) and the MBP-C125 substrate (0.05 mg/ml).

Gamma-secretase was then added to a 96-well micro-titre plate and then incubated with various concentrations of inhibitor for 30 minutes at 37° C. MBPC125 substrate was then added to initiate the reaction that would run for two hours at 37° C. The reaction was quenched with the addition of SDS to a final concentration of 0.1% and then 100 μl of the reaction mixture was transferred to a capture ELISA plate and incubated overnight at 4° C. Detection of the cleavage product was performed using a standard sandwich ELISA assay and quantified using a six point standard curve.

RESULTS

The following compounds when tested as described above exhibited inhibition with an $IC_{50}$ in a range of 300 nM-150 nM (A), in a range of 150 nM-50 nM (B), or of less than 50 nM (C).

| Structure | Compound Name | γAPP |
|---|---|---|
| 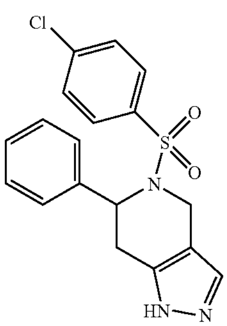 | 5-(4-chlorophenylsulfonyl)-6-phenyl-4,5,6,7-tetrahydro-1H-pyrazolo[4,3-c]pyridine | C |
| | 6-benzyl-5-(4-chlorophenylsulfonyl)-4,5,6,7-tetrahydro-1H-pyrazolo[4,3-c]pyridine | B |
| | 5-(4-chlorophenylsulfonyl)-6-isopropyl-4,5,6,7-tetrahydro-1H-pyrazolo[4,3-c]pyridine | C |
| | 5-(4-chlorophenylsulfonyl)-6-(4-fluorophenyl)-4,5,6,7-tetrahydro-1H-pyrazolo[4,3-c]pyridine | C |
| 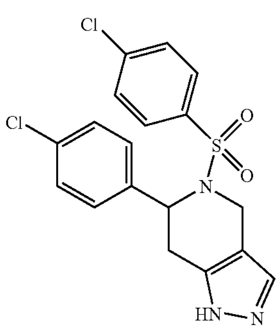 | 6-(4-chlorophenyl)-5-(4-chlorophenylsulfonyl)-4,5,6,7-tetrahydro-1H-pyrazolo[4,3-c]pyridine | C |
| | Enantiomer A | A |
| | Enantiomer B | C |
| | 5-(4-chlorophenylsulfonyl)-6-(3,5-difluorophenyl)-4,5,6,7-tetrahydro-1H-pyrazolo[4,3-c]pyridine | C |

| Structure | Compound Name | γAPP |
|---|---|---|
| | 5-(5-chlorothiophen-2-ylsulfonyl)-6-phenyl-4,5,6,7-tetrahydro-1H-pyrazolo[4,3-c]pyridine | C |
| | 5-(4-chlorophenylsulfonyl)-6-(3-fluorophenyl)-4,5,6,7-tetrahydro-1H-pyrazolo[4,3-c]pyridine | C |
| | 5-(4-chlorophenylsulfonyl)-6-(4-fluorophenyl)-4,5,6,7-tetrahydro-1H-pyrazolo[4,3-c]pyridine | |
| (structure) | (4R,6S)-4-(4-chlorophenyl)-5-(4-chlorophenylsulfonyl)-6-ethyl-4,5,6,7-tetrahydro-1H-pyrazolo[4,3-c]pyridine | C |
| | 6-(4-chlorophenyl)-5-(4-chlorophenylsulfonyl)-3-(trifluoromethyl)-4,5,6,7-tetrahydro-1H-pyrazolo[4,3-c]pyridine | A |
| | (4R,6R)-6-(4-chlorophenyl)-5-(4-chlorophenylsulfonyl)-4-ethyl-4,5,6,7-tetrahydro-1H-pyrazolo[4,3-c]pyridine | C |
| | (4S,6S)-5-(4-chlorophenylsulfonyl)-4,6-dimethyl-4,5,6,7-tetrahydro-1H-pyrazolo[4,3-c]pyridine | C |
| (structure) | (4R,6S)-5-(4-chlorophenylsulfonyl)-4,6-dimethyl-4,5,6,7-tetrahydro-1H-pyrazolo[4,3-c]pyridine | C |
| | 7-(4-chlorophenyl)-6-(4-chlorophenylsulfonyl)-5,6,7,8-tetrahydro-1,6-naphthyridine | A |
| | 5-(4-chlorophenyl)-6-(4-chlorophenylsulfonyl)-5,6,7,8-tetrahydro-1,6-naphthyridine | C |
| | 5-(4-chlorophenylsulfonyl)-6-(pyridin-3-yl)-4,5,6,7-tetrahydro-1H-pyrazolo[4,3-c]pyridine | B |
| | 5-(4-chlorophenylsulfonyl)-6-(pyridin-4-yl)-4,5,6,7-tetrahydro-1H-pyrazolo[4,3-c]pyridine | A |
| | (4R,6S)-5-(4-chlorophenylsulfonyl)-4,6-diethyl-4,5,6,7-tetrahydro-1H-pyrazolo[4,3-c]pyridine | C |
| (structure) | (4S,6R)-5-(4-chlorophenylsulfonyl)-4,6-diethyl-4,5,6,7-tetrahydro-1H-pyrazolo[4,3-c]pyridine | B |

-continued

| Structure | Compound Name | γAPP |
|---|---|---|
| | 5-(4-chlorophenylsulfonyl)-6-(pyrimidin-5-yl)-4,5,6,7-tetrahydro-1H-pyrazolo[4,3-c]pyrdine and 5-(4-Chloro-benzenesulfonyl)-4-pyrimidin-5-yl-4,5,6,7-tetrahydro-1H-pyrazolo[4,3-c]pyridine | A |
| | 5-(4-chlorophenylsulfonyl)-6-(pyrimidin-5-yl)-4,5,6,7-tetrahydro-1H-pyrazolo[4,3-c]pyridine Enantiomer A  Enantiomer B | C  C |
| | 5-(4-Chloro-benzenesulfonyl)-4-pyrimidin-5-yl-4,5,6,7-tetrahydro-1H-pyrazolo[4,3-c]pyridine Enantiomer A  Enantiomer B | A  C |
| | ethyl 5-(4-chlorophenylsulfonyl)-4,5,6,7-tetrahydo-1H-pyrazolo[4,3-c]pyridine-4-carboxylate Enantiomer A  Enantiomer B | A  C |
| 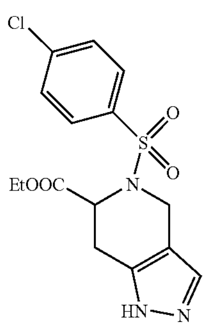 | ethyl 5-(4-chlorophenylsulfonyl)-4,5,6,7-tetrahydro-1H-pyrazolo[4,3-c]pyridine-6-carboxylate | |
| | (4S,6S)-5-(4-chlorophenylsulfonyl)-4,6-diethyl-4,5,6,7-tetrahydro-1H-pyrazolo[4,3-c]pyridine | A |
| | 5-(4-chlorophenylsulfonyl)-6-ethyl-6,7-dihydro-1H-pyrazolo[4,3-c]pyridin-4(5H)-one | A |
| | (5-(4-chlorophenylsulfonyl)-4,5,6,7-tetrahydro-1H-pyrazolo[4,3-c]pyridin-6-yl)methanol | A |
| | (4S,6S)-5-(4-chlorophenylsulfonyl)-4,6-diethyl-4,5,6,7-tetrahydro-1H-pyrazolo[4,3-c]pyridine | C |
| | 5-(4-chlorophenylsulfonyl)-6-ethyl-6,7-dihydro-1H-pyrazolo[4,3-c]pyridin-4(5H)-one | C |
| | (4R,6S)-5-(4-chlorophenylsulfonyl)-4,6-diethyl-5,6-dihydro-1H-pyrazolo[4,3-c]pyridin-7(4H)-one | C |
| | (4S,6R)-diethyl 5-(4-chlorophenylsulfonyl)-4,5,6,7-tetrahydro-1H-pyrazolo[4,3-c]pyridine-4,6-dicarboxylate | B |
| | ((4S,6R)-5-(4-chlorophenylsulfonyl)-4,5,6,7-tetrahydro-1H-pyrazolo[4,3-c]pyridine-4,6-diyl)dimethanol | A |

-continued

| Structure | Compound Name | γAPP |
|---|---|---|
| | (S)-(5-(4-chlorophenylsulfonyl)-4,5,6,7-tetrahydro-1H-pyrazolo[4,3-c]pyridin-4-yl)methyl dimethylcarbamate | A |
| | (4R,6S)-5-(4-chlorophenylsulfonyl)-4,6-diethyl-5,6-dihydro-1H-pyrazolo[4,3-c]pyridin-7(4H)-one | C |
| (structure shown) | (4S,6R)-5-(4-chlorophenylsulfonyl)-4,6-diethyl-5,6-dihydro-1H-pyrazolo[4,3-c]pyridin-7(4H)-one | A |
| (structure shown) | (S)-(5-(4-chlorophenylsulfonyl)-1-(dimethylcarbamoyl)-4,5,6,7-tetrahydro-1H-pyrazolo[4,3-c]pyridin-4-yl)methyl dimethylcarbamate | A |
| | (4R,6S)-4,6-diethyl-5-(pyridin-2-ylsulfonyl)-4,5,6,7-tetrahydro-1H-pyrazolo[4,3-c]pyridine | B |
| (structure shown) | 4-(1H-Benzoimidazol-2-yl)-5-(4-chloro-benzenesulfonyl)-4,5,6,7-tetrahydro-1H-pyrazolo[4,3-c]pyridine | A |
| | (4R,6S,Z)-5-(4-chlorophenylsulfonyl)-4,6-diethyl-5,6-dihydro-1H-pyrazolo[4,3-c]pyridin-7(4H)-one oxime | B |
| | ethyl 5-(4-chlorophenylsulfonyl)-6-ethyl-4,5,6,7-tetrahydro-1H-pyrazolo[4,3-c]pyridine-4-carboxylate | C |
| | (4R,6S)-4,6-diethyl-5-(4-fluorophenylsulfonyl)-4,5,6,7-tetrahydro-2H-pyrazolo[4,3-c]pyridine | C |
| | ((4S,6S)-5-(4-chlorophenylsulfonyl)-6-ethyl-4,5,6,7-tetrahydro-1H-pyrazolo[4,3-c]pyridin-4-yl)methyl dimethylcarbamate | A |

-continued

| Structure | Compound Name | γAPP |
|---|---|---|
| | ((4S,6S)-5-(4-chlorophenylsulfonyl)-4-ethyl-4,5,6,7-tetrahydro-1H-pyrazolo[4,3-c]pyridin-6-yl)methyl dimethylcarbamate | C |
| | ((4R,6S)-5-(4-chlorophenylsulfonyl)-4-ethyl-4,5,6,7-tetrahydro-1H-pyrazolo[4,3-c]pyridin-6-yl)methyl dimethylcarbamate | A |
| | ((4S,6R)-5-(4-chlorophenylsulfonyl)-6-ethyl-4,5,6,7-tetrahydro-1H-pyrazolo[4,3-c]pyridin-4-yl)methyl dimethylcarbamate | A |
| | 2-(5-(4-chlorophenylsulfonyl)-4,5,6,7-tetrahydro-2H-pyrazolo[4,3-c]pyridin-6-yl)thiazole | A |
| | 2-(5-(4-chlorophenylsulfonyl)-4,5,6,7-tetrahydro-2H-pyrazolo[4,3-c]pyridin-4-yl)thiazole | C |
| 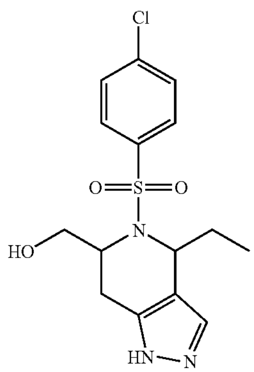 | 5-(4-chlorophenylsulfonyl)-4-ethyl-4,5,6,7-tetrahydro-1H-pyrazolo[4,3-c]pyridin-6-yl)methanol | C |
| 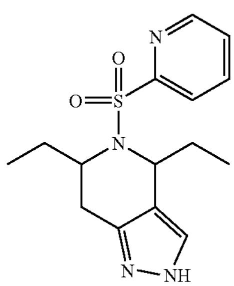 | 4,6-diethyl-5-(pyridin-2-ylsulfonyl)-4,5,6,7-tetrahydro-2H-pyrazolo[4,3-c]pyridine (enantiomer A) | B |
| | 4,6-diethyl-5-(pyridin-2-ylsulfonyl)-4,5,6,7-tetrahydro-2H-pyrazolo[4,3-c]pyridine (enantiomer B) | C |

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. Compounds of the formula:

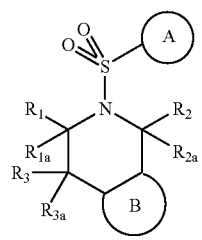

(Formula I)

stereoisomers, tautomers, mixtures of stereoisomers and/or tautomers or pharmaceutically acceptable salts thereof, wherein the A-ring is phenyl or pyridyl, where each ring is optionally substituted at a substitutable position with $R_{10}$, $R_{11}$, $R_{12}$, $R_{13}$, or $R_{14}$,
wherein $R_{10}$, $R_{11}$, $R_{12}$, $R_{13}$, and $R_{14}$ are independently selected from halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxyl, hydroxyalkyl, CN, —SO$_2$—(C$_1$-C$_6$ alkyl), —NR'R", $C_1$-$C_6$ alkanoyl, $C_0$-$C_3$alkyl-C(O)OR', —SO$_2$—NR'R", where each R' and R" is independently H or $C_1$-$C_6$ alkyl;

the B-ring is a pyrazolyl ring which is optionally substituted with one $R_{20}$ group,
wherein $R_{20}$ is $C_1$-$C_6$ alkyl, $C_2$-$C_6$ alkenyl, $C_2$-$C_6$ alkynyl, $C_1$-$C_6$ alkoxy, —S(O)$_{0-2}$R', hydroxyl, hydroxyalkyl, halo, $C_1$-$C_2$ haloalkyl, $C_1$-$C_2$ haloalkoxy, —NR'SO$_2$R", —C(O)R', —CO$_2$R', —C(O)alkylOC(O)R', —C(O)NR'R", CN, or $C_0$-$C_1$alkylaryl; and $R_1$ is halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkylC$_1$-C$_6$ alkyl, aryl, arylC$_1$-C$_6$ alkyl, heteroaryl, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, aryloxyC$_1$-C$_6$ alkyl, heteroaryloxy $C_1$-$C_6$ alkyl, —C$_0$-C$_6$ alkyl-OC(O)NR'R", —C$_0$-C$_6$ alkyl-NR'R", hydroxyl, or —C$_0$-C$_6$ alkyl-OC(O)-heterocycloalkyl, wherein each aryl, heteroaryl, and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, or —C(O)OR';

$R_{1a}$, $R_2$, and $R_{2a}$ are independently hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkylC$_1$-C$_6$ alkyl, aryl, arylC$_1$-C$_6$ alkyl, heteroaryl, —CO$_2$R', CONR'R", $C_1$-$C_6$ haloalkyl, where the haloalkyl group is optionally substituted with $C_1$-$C_4$ alkoxy; $C_1$-$C_4$ haloalkoxyalkyl, hydroxy $C_1$-$C_6$ alkyl, $C_2$-$C_6$ alkanoyl, aryloxyC$_1$-C$_6$ alkyl, heteroaryloxy C$_1$-C$_6$ alkyl, —C$_0$-C$_6$ alkyl-OC(O)NR'R", —C$_0$-C$_6$ alkyl-NR'R", hydroxyl, or —C$_0$-C$_6$ alkyl-OC(O)-heterocycloalkyl, wherein each aryl, heteroaryl, and heterocycloalkyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—(CH$_2$)$_{1-2}$—O—, —C(O)OR';

$R_3$, and $R_{3a}$ are independently hydrogen, halogen, or $C_1$-$C_6$ alkyl, $R_1$, and $R_{1a}$, or $R_3$ and $R_{3a}$ combined form =N—OR, where R is hydrogen, $C_1$-$C_6$ alkyl, aryl or arylalkyl; or $R_1$, and $R_{1a}$, or $R_2$ and $R_{2a}$ or $R_3$ and $R_{3a}$ together with the carbon to which they are attached form $C_3$-$C_6$ cycloalkyl group and wherein said ring may be optionally substituted with $C_1$-$C_6$ alkyl.

2. Compounds or salts according to claim 1, where the B-ring is pyrazolyl which is optionally substituted with one $R_{20}$ group,
wherein $R_{20}$ is $C_1$-$C_6$ alkyl, $C_1$-$C_6$ alkoxy, $C_1$-$C_6$ alkylthio, halo, $C_1$-$C_2$ haloalkyl, $C_1$-$C_2$ haloalkoxy, or $C_0$-$C_1$alkyl phenyl, are optionally substituted with 1 to 5 groups that are independently halogen, hydroxyl, $C_1$-$C_6$ alkyl, $C_1$-$C_6$ alkoxy, $C_1$-$C_4$ haloalkyl, $C_1$-$C_4$haloalkoxy, $C_1$-$C_6$ alkanoyl, —NR'R", —CO$_2$R', CN or NO$_2$.

3. Compounds or salts according to claim 2, where
$R_1$ is $C_1$-$C_6$ alkyl, $C_3$-$C_6$ cycloalkyl, $C_3$-$C_6$ cycloalkyl $C_1$-$C_6$ alkyl, phenyl, biphenyl, phenyl$C_1$-$C_6$ alkyl, pyridyl, benzofuranyl, benzothienyl, benzimidazolyl, quinolinyl, isoquinolinyl, quinoxalinyl, quinazolinyl, tetrazolyl, oxazolyl, thiazolyl, imidazolyl, oxadiazolyl, thiazolyl, pyrimidyl, —CO$_2$R, —CONR'R', $C_1$-$C_6$ haloalkyl, hydroxy $C_1$-$C_6$ alkyl, $C_1$-$C_6$ alkoxy, phenyloxyC$_1$-C$_6$ alkyl, naphthyloxyC$_1$-C$_6$ alkyl, pyridyloxy $C_1$-$C_6$ alkyl, benzofuranyloxy $C_1$-$C_6$ alkyl, benzothienyloxy $C_1$-$C_6$ alkyl, quinolinyloxy $C_1$-$C_6$ alkyl, isoquinolinyloxy $C_1$-$C_6$ alkyl, quinoxalinyloxy $C_1$-$C_6$ alkyl, quinazolinyloxy $C_1$-$C_6$ alkyl, —C$_0$-C$_6$ alkyl-OC(O)NR'R", —C$_0$-C$_6$ alkyl-NR'R", —C$_1$-C$_6$ alkyl-OC(O)-piperidinyl, —C$_1$-C$_6$ alkyl-OC(O)-pyrrolidinyl, —C$_1$-C$_6$ alkyl-OC(O)-morpholinyl, wherein each aryl, heteroaryl, and heterocycloalkyl group is optionally substituted with one or more groups that are independently halogen, $C_1$-$C_6$ alkyl, $C_1$-$C_6$ alkoxy, halo $C_1$-$C_4$ alkyl, halo $C_1$-$C_4$ alkoxy, $C_1$-$C_6$ alkanoyl, —C(O)NR'R", —NR'R", —O—(CH$_2$)$_{1-2}$—O—, or —O$_2$R'.

4. Compounds or salts according to claim 3, having the following formula:

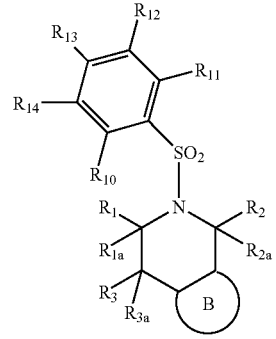

Formula 6 wherein, $R_{12}$ is H, halogen, $C_1$-$C_6$ alkyl, $C_1$-$C_6$ alkoxy, $C_1$-$C_6$ haloalkyl, or CN;

$R_{13}$ is H, halogen, $C_1$-$C_6$ alkyl, $C_1$-$C_3$ alkyl-CO$_2$—(C$_1$-C$_6$ alkyl), $C_1$-$C_6$ alkoxy, $C_1$-$C_6$ haloalkyl, $C_1$-$C_6$ haloalkoxy, CN, —SO$_2$—(C$_1$-C$_6$ alkyl), —NR'R", $C_1$-$C_6$ alkanoyl, pyridyl, or phenyl; or $R_{14}$ is H, $C_1$-$C_4$ alkyl, —SO$_2$—NR'R", or halogen;

where R' and R" are independently H or $C_1$-$C_6$ alkyl; or $R_{10}$ and $R_{11}$ at each occurrence are independently H, halogen, or $C_1$-$C_6$ alkyl, where the alkyl is optionally substituted with a phenyl, where the phenyl is optionally substituted with 1 to 5 groups that are independently halogen, hydroxyl, $C_1$-$C_6$ alkyl, $C_1$-$C_6$ alkoxy, $C_1$-$C_4$ haloalkyl, $C_1$-$C_4$ haloalkoxy, CN or NO$_2$.

5. Compounds or salts according to claim 4, where the B-ring has the following formula:

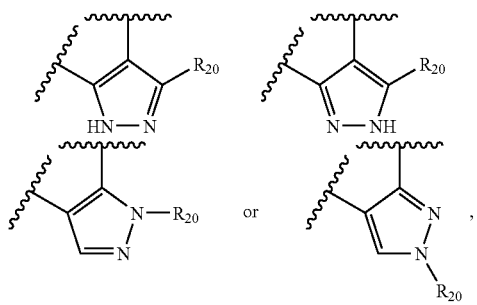

wherein $R_{20}$ is H, $C_1$-$C_6$ alkyl, $C_1$-$C_6$ alkoxy, —SR', halo, $CF_3$, or phenyl, where R' is $C_1$-$C_6$ alkyl.

6. Compounds or salts according to claim 4, wherein $R_1$ is $C_1$-$C_6$ alkyl, $C_3$-$C_6$cycloalkyl, $C_3$-$C_6$cycloalkylalkyl, phenyl, biphenyl, phenyl$C_1$-$C_6$ alkyl (such as benzyl or phenethyl), phenyloxy$C_1$-$C_6$ alkyl, or naphthyloxy$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, halo $C_1$-$C_4$ alkyl, halo $C_1$-$C_4$ alkoxy, —C(O)NR'R", —NR'R", hydroxyl, —O—$(CH_2)_{1-2}$—O—, or —$CO_2$R'; and $R_{1a}$, $R_{2a}$, $R_3$ and $R_{3a}$ are H.

7. A composition comprising a compound or salt of claim 1 and at least one pharmaceutically acceptable solvent, adjuvant, excipient, carrier, binder or disintegrant.

8. Compounds according to claim 1 that are
5-(4-chlorophenylsulfonyl)-4,6-dicyclopropyl-4,5,6,7-tetrahydro-1H-pyrazolo[4,3-c]pyridine;
cis-(5-(4-chlorophenylsulfonyl)-4-ethyl-4,5,6,7-tetrahydro-1H-pyrazolo[4,3-c]pyridin-6-yl)methanol;
6-methyl-4-(pyrimidin-5-yl)-5-(4-(trifluoromethyl)phenylsulfonyl)-4,5,6,7-tetrahydro-1H-pyrazolo[4,3-c]pyridine;
(4-(pyrimidin-5-yl)-5-(4-(trifluoromethyl)phenylsulfonyl)-4,5,6,7-tetrahydro-1H-pyrazolo[4,3-c]pyridin-6-yl)methanol;
5-(4-chlorophenylsulfonyl)-6-methyl-4-(pyrimidin-5-yl)-4,5,6,7-tetrahydro-1H-pyrazolo[4,3-c]pyridine;
5-(4-chlorophenylsulfonyl)-6-cyclopropyl-4-(pyrimidin-5-yl)-4,5,6,7-tetrahydro-1H-pyrazolo[4,3-c]pyridine;
5-(4-chlorophenylsulfonyl)-4,6-bis(1,1-difluoroethyl)-4,5,6,7-tetrahydro-1H-pyrazolo[4,3-c]pyridine;
5-(4-chlorophenylsulfonyl)-4,6-bis(difluoromethyl)-4,5,6,7-tetrahydro-1H-pyrazolo[4,3-c]pyridine;
1,1'-(5-(4-chlorophenylsulfonyl)-4,5,6,7-tetrahydro-1H-pyrazolo[4,3-c]pyridine-4,6-diyl)diethanone;
5-(4-chlorophenylsulfonyl)-4,6-bis(2,2-difluorovinyl)-4,5,6,7-tetrahydro-1H-pyrazolo[4,3-c]pyridine;
5-(4-chlorophenylsulfonyl)-4,6-bis(2,2-difluoroethyl)-4,5,6,7-tetrahydro-1H-pyrazolo[4,3-c]pyridine;
5-(4-chlorophenylsulfonyl)-4,6-bis(fluoromethyl)-4,5,6,7-tetrahydro-1H-pyrazolo[4,3-c]pyridine;
5-(4-chlorophenylsulfonyl)-4,6-bis(difluoro(methoxy)methyl)-4,5,6,7-tetrahydro-1H-pyrazolo[4,3-c]pyridine;
5-(4-chlorophenylsulfonyl)-4,6-bis((trifluoromethoxy)methyl)-4,5,6,7-tetrahydro-1H-pyrazolo[4,3-c]pyridine;
5-(4-chlorophenylsulfonyl)-4,6-bis(2,2,2-trifluoroethyl)-4,5,6,7-tetrahydro-1H-pyrazolo[4,3-c]pyridine;
5-(4-chlorophenylsulfonyl)-4,6-diisopropyl-4,5,6,7-tetrahydro-1H-pyrazolo[4,3-c]pyridine;
5-(4-chlorophenylsulfonyl)-4,6-diethyl-N,N-dimethyl-4,5,6,7-tetrahydro-1H-pyrazolo[4,3-c]pyridin-7-amine;
5-(4-chlorophenylsulfonyl)-4,6-diethyl-4,5,6,7-tetrahydro-1H-pyrazolo[4,3-c]pyridin-7-amine;
5-(4-chlorophenylsulfonyl)-4,6-diethyl-4,5,6,7-tetrahydro-1H-pyrazolo[4,3-c]pyridin-7-ol;
5-(4-chlorophenylsulfonyl)-4,6-diethyl-7-fluoro-4,5,6,7-tetrahydro-1H-pyrazolo[4,3-c]pyridine;
5-(4-chlorophenylsulfonyl)-4,6-diethyl-7,7-difluoro-4,5,6,7-tetrahydro-1H-pyrazolo[4,3-c]pyridine;
5-(4-chlorophenylsulfonyl)-4,6-bis(trifluoromethyl)-4,5,6,7-tetrahydro-1H-pyrazolo[4,3-c]pyridine;
5-(4-chlorophenylsulfonyl)-6-phenyl-4,5,6,7-tetrahydro-1H-pyrazolo[4,3-c]pyridine;
6-benzyl-5-(4-chlorophenylsulfonyl)-4,5,6,7-tetrahydro-1H-pyrazolo[4,3-c]pyridine;
5-(4-chlorophenylsulfonyl)-6-isopropyl-4,5,6,7-tetrahydro-1H-pyrazolo[4,3-c]pyridine;
5-(4-chlorophenylsulfonyl)-6-(4-fluorophenyl)-4,5,6,7-tetrahydro-1H-pyrazolo[4,3-c]pyridine;
6-(4-chlorophenyl)-5-(4-chlorophenylsulfonyl)-4,5,6,7-tetrahydro-1H-pyrazolo[4,3-c]pyridine;
5-(4-chlorophenylsulfonyl)-6-(3,5-difluorophenyl)-4,5,6,7-tetrahydro-1H-pyrazolo[4,3-c]pyridine;
4-(4-chlorophenyl)-5-(4-chlorophenylsulfonyl)-6-ethyl-4,5,6,7-tetrahydro-1H-pyrazolo[4,3-c]pyridine;
6-(4-chlorophenyl)-5-(4-chlorophenylsulfonyl)-3-(trifluoromethyl)-4,5,6,7-tetrahydro-1H-pyrazolo[4,3-c]pyridine;
6-(4-chlorophenyl)-5-(4-chlorophenylsulfonyl)-4-ethyl-4,5,6,7-tetrahydro-1H-pyrazolo[4,3-c]pyridine;
5-(4-chlorophenylsulfonyl)-4,6-dimethyl-4,5,6,7-tetrahydro-1H-pyrazolo[4,3-c]pyridine;
5-(4-chlorophenylsulfonyl)-6-(pyridin-3-yl)-4,5,6,7-tetrahydro-1H-pyrazolo[4,3-c]pyridine;
5-(4-chlorophenylsulfonyl)-6-(pyridin-4-yl)-4,5,6,7-tetrahydro-1H-pyrazolo[4,3-c]pyridine;
5-(4-chlorophenylsulfonyl)-4,6-diethyl-4,5,6,7-tetrahydro-1H-pyrazolo[4,3-c]pyridine;
5-(4-chlorophenylsulfonyl)-6-(pyrimidin-5-yl)-4,5,6,7-tetrahydro-1H-pyrazolo[4,3-c]pyridine;
ethyl 5-(4-chlorophenylsulfonyl)-4,5,6,7-tetrahydro-1H-pyrazolo[4,3-c]pyridine-6-carboxylate;
(5-(4-chlorophenylsulfonyl)-4,5,6,7-tetrahydro-1H-pyrazolo[4,3-c]pyridin-6-yl)methanol;
diethyl 5-(4-chlorophenylsulfonyl)-4,5,6,7-tetrahydro-1H-pyrazolo[4,3-c]pyridine-4,6-dicarboxylate;
5-(4-chlorophenylsulfonyl)-4,5,6,7-tetrahydro-1H-pyrazolo[4,3-c]pyridine-4,6-diyl)dimethanol;
4,6-diethyl-5-(pyridin-2-ylsulfonyl)-4,5,6,7-tetrahydro-1H-pyrazolo[4,3-c]pyridine;
ethyl 5-(4-chlorophenylsulfonyl)-6-ethyl-4,5,6,7-tetrahydro-1H-pyrazolo[4,3-c]pyridine-4-carboxyl ate;
4,6-diethyl-5-(4-fluorophenylsulfonyl)-4,5,6,7-tetrahydro-2H-pyrazolo[4,3-c]pyridine;
5-(4-chlorophenylsulfonyl)-6-ethyl-4,5,6,7-tetrahydro-1H-pyrazolo[4,3-c]pyridin-4-yl)methyl dimethylcarbamate;
5-(4-chlorophenylsulfonyl)-4-ethyl-4,5,6,7-tetrahydro-1H-pyrazolo[4,3-c]pyridin-6-yl)methyl dimethylcarbamate;
2-(5-(4-chlorophenylsulfonyl)-4,5,6,7-tetrahydro-2H-pyrazolo[4,3-c]pyridin-6-yl)thiazole;
5-(4-chlorophenylsulfonyl)-4-ethyl-4,5,6,7-tetrahydro-1H-pyrazolo[4,3-c]pyridin-6-yl )methanol;
4,6-diethyl-5-(pyridin-2-ylsulfonyl)-4,5,6,7-tetrahydro-2H-pyrazolo[4,3-c]pyridine;

and stereoisomers, tautomers, mixtures of stereoisomers and/or tautomers or pharmaceutically acceptable salts thereof.

9. Compounds or salts according to claim 5, wherein the B-ring has the formula:

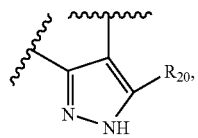

wherein $R_{20}$ is H, $C_1$-$C_4$ alkyl, $C_1$-$C_4$ alkoxy, —S R', halo, $CF_3$, or phenyl, where R' is $C_1$-$C_4$ alkyl.

10. Compounds or salts according to claim 4, wherein $R_2$ is hydrogen, halogen, $C_1$-$C_6$ alkyl, $C_2$-$C_6$ alkenyl, where the alkenyl group is optionally substituted with one or more halogens; $C_2$-$C_6$ alkynyl, $C_3$-$C_6$cycloalkyl, $C_3$-$C_6$cycloalkyl$C_1$-$C_6$ alkyl, phenyl, naphthyl, phenyl$C_1$-$C_6$ alkyl, naphthyl$C_1$-$C_6$ alkyl, wherein each aryl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, —O—$(CH_2)_{1-2}$—O—, or —C(O)OR'.

11. Compounds or salts according to claim 5, wherein $R_1$ is H, $C_1$-$C_4$ alkyl, benzyl, phenethyl, or phenyl, where the phenyl portions of $R_1$ are optionally substituted with 1, 2, or 3 groups that are independently halogen, $C_1$-$C_4$ alkyl, or $C_1$-$C_4$ alkoxy; $R_2$ is H or $C_1$-$C_4$ alkyl, and $R_{1a}$ and $R_{2a}$ are both H.

12. Compounds or salts according to claim 11, wherein $R_2$ is H, and $R_1$ is phenyl substituted with one or two halogens.

13. Compounds or salts according to claim 11, wherein $R_2$ is methyl or ethyl, and $R_1$ is phenyl substituted with one or two halogens.

14. Compounds or salts according to claim 4, wherein $R_{10}$, $R_{11}$, $R_{12}$, $R_{13}$, and $R_{14}$ are independently of each other H, halo, $CF_3$, $CHF_2$ or methyl.

15. Compounds or salts according to claim 9, wherein $R_{10}$, $R_{11}$, $R_{12}$, $R_{13}$, and $R_{14}$ are independently of each other H, halo, $CF_3$, $CHF_2$ or methyl.

16. Compounds or salts according to claim 9, wherein $R_{13}$ is H, halogen, $C_1$-$C_6$ alkyl, $C_1$-$C_3$ alkyl-$CO_2$—($C_1$-$C_6$ alkyl), $C_1$-$C_6$ alkoxy, $CF_3$, $OCF_3$, or CN.

17. Compounds or salts according to claim 16, wherein $R_{12}$, $R_{14}$, $R_{10}$, and $R_{11}$ are H.

18. Compounds or salts according to claim 4, wherein $R_3$ and $R_{3a}$ are H.

19. A compound that is:
5-(4-chlorophenylsulfonyl)-6-(pyrimidin-5-yl)-5,6-dihydro-1H-pyrazolo[4,3-c]pyridin-7(4H)-one;
5-(4-chlorophenylsulfonyl)-4-(pyrimidin-5-yl)-5,6-dihydro-1H-pyrazolo[4,3-c]pyridin-7(4H)-one;
4,6-dimethyl-5-(4-(trifluoromethyl)phenylsulfonyl)-5,6-dihydro-1H-pyrazolo[4,3-c]pyridin-7(4H)-one;
5-(4-fluorophenylsulfonyl)-4,6-dimethyl-5,6-dihydro-1H-pyrazolo[4,3-c]pyridin-7(4H)-one;
4,6-dimethyl-5-(pyridin-2-ylsulfonyl)-5,6-dihydro-1H-pyrazolo[4,3-c]pyridin-7(4H)-one;
6-methyl-4-(pyrimidin-5-yl)-5-(4-(trifluoromethyl)phenylsulfonyl)-5,6-dihydro-1H-pyrazolo[4,3-c]pyridin-7(4H)-one;
6-methyl-4-(pyridin-3-yl)-5-(4-(trifluoromethyl)phenylsulfonyl)-5,6-dihydro-1H-pyrazolo[4,3-c]pyridin-7(4H)-one;
6-methyl-4-(pyridin-4-yl)-5-(4-(trifluoromethyl)phenylsulfonyl)-5,6-dihydro-1H-pyrazolo[4,3-c]pyridin-7(4H)-one;
5-(4-chlorophenylsulfonyl)-4,6-diethyl-5,6-dihydro-1H-pyrazolo[4,3-c]pyridin-7(4H)-one O-methyl oxime;
6-methyl-4-(thiazol-2-yl)-5-(4-(trifluoromethyl)phenylsulfonyl)-5,6-dihydro-1H-pyrazolo[4,3-c]pyridin-7(4H)-one;
4-(1H-imidazol-5-yl)-6-methyl-5-(4-(trifluoromethyl)phenylsulfonyl)-5,6-dihydro-1H-pyrazolo[4,3-c]pyridin-7(4H)-one;
4-(1H-imidazol-2-yl)-6-methyl-5-(4-(trifluoromethyl)phenylsulfonyl)-5,6-dihydro-1H-pyrazolo[4,3-c]pyridin-7(4H)-one;
5-(4-chlorophenylsulfonyl)-4-isopropyl-5,6-dihydro-1H-pyrazolo[4,3-c]pyridin-7(4H)-one;
5-(4-chlorophenylsulfonyl)-4,6-diethyl-5,6-dihydro-1H-pyrazolo[4,3-c]pyridin-7(4H)-one;
5-(4-chlorophenylsulfonyl)-4,6-diethyl-5,6-dihydro-1H-pyrazolo[4,3-c]pyridin-7(4H)-one oxime;
4,6-dimethyl-5-(4-(trifluoromethyl)phenylsulfonyl)-5,6-dihydro-2H-pyrazolo[4,3-c]pyridin-7(4H)-one;
and stereoisomers, tautomers, mixtures of stereoisomers and/or tautomers or pharmaceutically acceptable salts thereof.

20. A compound that is:
4-(pyrimidin-5-yl)-5-(4-(trifluoromethyl)phenylsulfonyl)-4,5,6,7-tetrahydro-1H-pyrazolo[4,3-c]pyridine;
5'-(4-chlorophenylsulfonyl)-1',5',6',7'-tetrahydrospiro[cyclopropane-1,4'-pyrazolo[4,3-c]pyridine];
5-(4-Chloro-benzenesulfonyl)-4-pyrimidin-5-yl-4,5,6,7-tetrahydro-1H-pyrazolo[4,3-c]pyridine;
ethyl 5-(4-chlorophenylsulfonyl)-4,5,6,7-tetrahydro-1H-pyrazolo[4,3-c]pyridine-4-carboxylate;
(5-(4-chlorophenylsulfonyl)-4,5,6,7-tetrahydro-1H-pyrazolo[4,3-c]pyridin-4-yl)methyl dimethylcarbamate;
(5-(4-chlorophenylsulfonyl)-1-(dimethylcarbamoyl)-4,5,6,7-tetrahydro-1H-pyrazolo[4,3-c]pyridin-4-yl)methyl dimethylcarbamate;
4-(1H-benzoimidazol-2-yl)-5-(4-chloro-benzenesulfonyl)-4,5,6,7-tetrahydro-1H-pyrazolo[4,3-c]pyridine;
2-(5-(4-chlorophenylsulfonyl)-4,5,6,7-tetrahydro-2H-pyrazolo[4,3-c]pyridin-4-yl)thiazole;
and stereoisomers, tautomers, mixtures of stereoisomers and/or tautomers or pharmaceutically acceptable salts thereof.

* * * * *

UNITED STATES PATENT AND TRADEMARK OFFICE
CERTIFICATE OF CORRECTION

PATENT NO.         : 7,732,609 B2                                             Page 1 of 1
APPLICATION NO.    : 11/566070
DATED              : June 8, 2010
INVENTOR(S)        : Ye et al.

It is certified that error appears in the above-identified patent and that said Letters Patent is hereby corrected as shown below:

On the Title Page, item [75], line 4, delete "Jagodinski" and replace with --Jagodzinski--.

Signed and Sealed this

Fourteenth Day of September, 2010

David J. Kappos
*Director of the United States Patent and Trademark Office*